United States Patent [19]

Atsumi et al.

[11] Patent Number: 4,988,686
[45] Date of Patent: Jan. 29, 1991

[54] CEPHEM COMPOUNDS AND ANTI-BACTERIAL AGENT

[75] Inventors: Kunio Atsumi; Katsuyoshi Iwamatsu; Kenji Sakagami; Hiroko Ogino; Takashi Yoshida, all of Yokohama, Japan

[73] Assignee: Meiji Seika Kabushiki Kaisha, Tokyo, Japan

[21] Appl. No.: 373,176

[22] Filed: Jun. 28, 1989

[30] Foreign Application Priority Data

Jul. 1, 1988 [JP] Japan .................................. 63-164165

[51] Int. Cl.$^5$ .................. C07D 501/24; A61K 31/545
[52] U.S. Cl. ..................................... 514/203; 540/222; 540/225; 514/202
[58] Field of Search ................ 540/222, 225; 214/202, 214/203

[56] References Cited

U.S. PATENT DOCUMENTS

| 4,822,786 | 4/1989 | Zama et al. | 540/222 |
| 4,839,350 | 6/1989 | Atsumi et al. | 540/222 |

FOREIGN PATENT DOCUMENTS

| 54-321081 | 3/1979 | Japan . |
| 55-24763 | 2/1980 | Japan . |
| 58-163102 | 9/1983 | Japan . |
| 59-184464 | 9/1984 | Japan . |
| 60-140989 | 6/1985 | Japan . |
| 60-157005 | 7/1985 | Japan . |
| 61-44203 | 3/1986 | Japan . |
| 61-77893 | 4/1986 | Japan . |
| 61-77894 | 4/1986 | Japan . |
| 62-284634 | 11/1987 | Japan . |
| 63-107262 | 4/1988 | Japan . |

Primary Examiner—Nicholas S. Rizzo
Attorney, Agent, or Firm—Ladas & Parry

[57] ABSTRACT

Disclosed is a novel cephem compound which is either one of a cis- or trans-isomer or a mixture of the cis-and trans-isomers, represented by the following general formula (I) and a pharmacologically acceptable salt thereof:

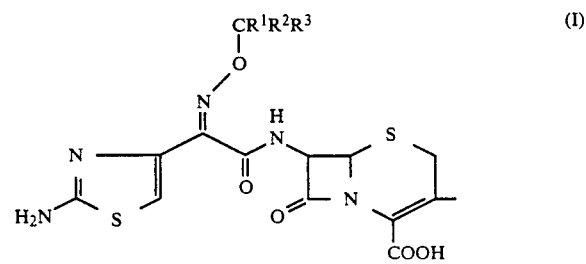

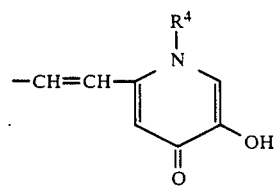

wherein all of the substituents are as defined hereinbefore.

Also disclosed are a process for producing the above compound and its use as an anti-bacterial agent comprising the same.

2 Claims, No Drawings

CEPHEM COMPOUNDS AND ANTI-BACTERIAL AGENT

BACKGROUND OF THE INVENTION

1. Technical Field

The present invention relates to a novel β-lactam type anti-bacterial agent and a pharmaceutically acceptable salt thereof. More particularly, it relates to a novel cephem compound and a pharmaceutically acceptable salt thereof, a process for producing them and an anti-bacterial agent containing them as effective ingredients. The present compound has an excellent therapeutic effect against diseases caused by human or animal pathogens and is useful as a remedy for human and veterinary use.

2. Background Art

Cephem type compounds structurally relevant to the compound according to the present invention include the ones which are disclosed in Japanese Patent Laid-Open Publication Nos. 124790/1980, 122388/1981 and 76083/1984. Also, the compounds which have been discovered by the present inventors and are disclosed in Japanese Patent Laid-Open Publication Nos. 178991/1986, 19593/1987 and 205088/1987 are structurally relevant cephem type compounds, which have a β-substituted vinyl side chain as in the compound of the present invention. However, the compound of the present invention is a novel cephem compound which is different from these known relevant compounds with regard to the substituents of the side chain.

Cephalosporin type antibiotics exhibit wide antibacterial activities against Gram-positive and Gram-negative bacteria. A variety of semi-synthetic cephalosporin type compounds are now commercially available and have clinical uses as remedies against infectious diseases. However, among those compounds, very few exhibits anti-bacterial activity against Pseudomonas aeruginosa or Myxomycetes, and many of these compounds are unstable to β-lactamase which is produced by a resistant bacterium and thus have drawbacks in a low anti-bacterial activity against resistant bacterium which is a serious problem on clinical therapies (W. E. Wick, Chapter 11 in "Cephalosporins and Penicillins, Chemistry and Biology", edited by E. H. Flynn, Academic Press, New York, N.Y., 1972).

DISCLOSURE OF THE INVENTION

The present inventors have previously found as disclosed in Japanese Patent Laid-Open Publication Nos. 174083/1987 and 238290/1987 and Japanese Patent Application Nos. 108227/1987 and 284634/1987 that a novel cephalosporin derivative having a 1-substituted-5-hydroxy-4-pyridon-2-yl group at the part of the amide side chain at the 7-position of the cephem ring exhibits strong activities against wide range of pathogens. On the other hand, a novel cephem compound having a vinyl group of which the β-position is substituted with a heterocycle at the 3-position of the cephem ring is also disclosed in Japanese Patent Laid-Open Publication Nos. 178991/1986, 19593/1987 and 205088/1987. They have further developed their researches from the viewpoint of the 5-hydroxy-4-pyridone structure of the former compound and applied thereto the structural features of the latter. As a result, they have found that the novel cephem compound represented by the formula (I) possesses very strong anti-bacterial activities over a wide range of bacteria including both Gram-positive and Gram-negative, particularly exhibits extremely strong anti-bacterial activity against Pseudomonas aeruginosa, and it also exhibits strong anti-bacterial activities against a variety of β-lactamase producing bacteria, and that it can be readily ingested with toxicity sustained at a low level. The present invention has thus accomplished.

SUMMARY

The present invention first of all relates to a novel compound. The compound according to the present invention is the novel cephem compound which is either one of a cis- or trans-isomer or a mixture of the cis- and trans-isomers, represented by the following general formula (I) and a pharmacologically acceptable salt thereof. The present invention also relates to the use of the cephem compound and the pharmacologically acceptable salt thereof, and the use according to the present invention, i.e. an anti-bacterial agent contains the novel cephem compound represented by the following formula (I) or a pharmacologically acceptable salt thereof as an effective ingredient:

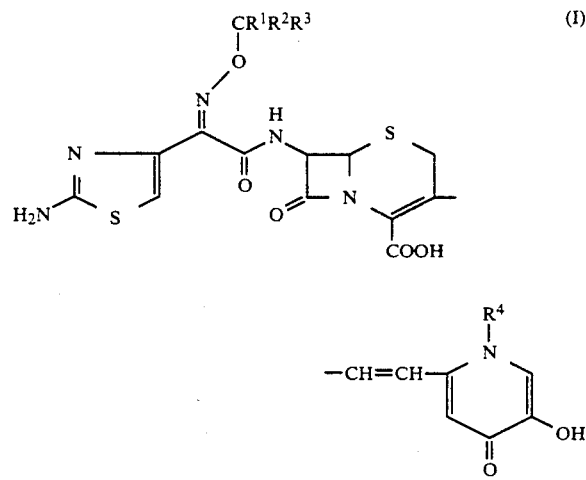

wherein $R^1$ represents a hydrogen atom, a carboxy group or an N-lower alkylcarbamoyl group, $R^2$ and $R^3$ may be the same or different and independently represent a hydrogen atom or a $C_1$–$C_3$ lower alkyl group, $R^4$ represents a hydrogen atom, a hydroxy group, a straight chain or branched $C_1$–$C_4$ lower alkoxy group, a substituted or unsubstituted straight chain or branched $C_1$–$C_4$ lower alkyl group, a $C_3$–$C_6$ cycloalkyl group, a $C_2$–$C_4$ alkenyl or alkynyl group, a substituted or unsubstituted phenylmethyl or heterocyclic methyl group.

Furthermore, the present invention relates to the production of the novel compound represented by the general formula (I). In other words, the present invention is characterized in that a compound represented by the following general formula (II):

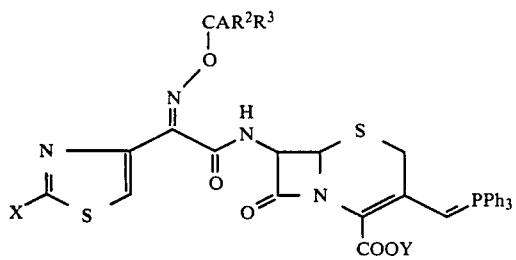

wherein A represents a hydrogen atom, an N-lower alkylcarbamoyl group or a carboxy group which may be protected, $R^2$ and $R^3$ may be the same or different and independently represent a hydrogen atom or a $C_1$-$C_3$ lower alkyl group, X represents an amino group which may be protected, and Y represents a protecting group of a carboxy group, is reacted with a compound represented by the following general formula (III):

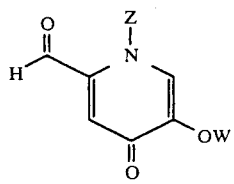

wherein Z represents a hydrogen atom, a hydroxy group which may be protected, a straight chain or branched $C_1$-$C_4$ lower alkoxy group, a substituted or unsubstituted straight chain or branched $C_1$-$C_4$ lower alkyl group which may be protected, a $C_3$-$C_6$ cycloalkyl group, a $C_2$-$C_4$ alkenyl or alkynyl group, a substituted or unsubstituted phenylmethyl or heterocyclic methyl group which may be protected, and W represents a protecting group of an enolic hydroxy group, and if necessary, the protecting groups are eliminated from the resulting product.

The present invention is a process for producing a novel cephem compound wherein $R^4$ represents a hydrogen atom or a hydroxy group represented by the general formula (I), characterized in that a compound represented by the general formula (II):

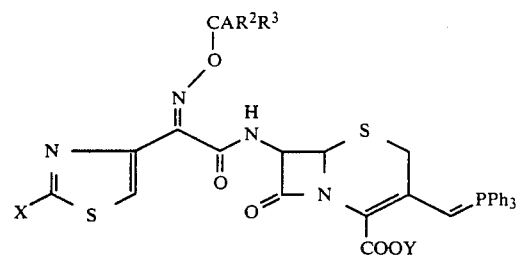

wherein A represents a hydrogen atom, an N-lower alkylcarbamoyl group or a carboxy group which may be protected, $R^2$ and $R^3$ may be the same or different and independently represent a hydrogen atom or a $C_1$-$C_3$ lower alkyl group, X represents an amino group which may be protected, and Y represents a protecting group of a carboxy group, is reacted with a compound represented by the following general formula (III)':

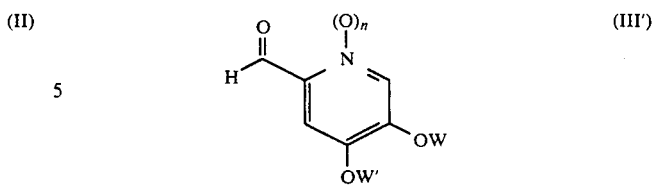

wherein n denotes 0 or 1, W and W' may be the same or different and independently represent a protecting group of an enolic hydroxy group, and if necessary, the protecting groups are eliminated from the resulting product.

Moreover, the present invention is characterized in that a compound represented by the following general formula (VII):

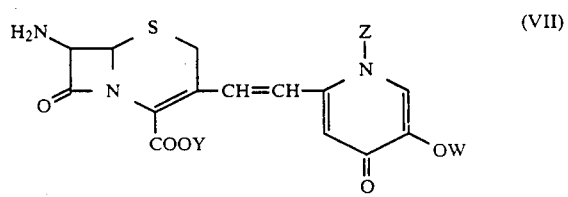

wherein Y represents a hydrogen atom or a protecting group of a carboxy group, Z represents a hydrogen atom, a hydroxy group which may be protected, a straight chain or branched $C_1$-$C_4$ lower alkoxy group, a substituted or unsubstituted straight chain or branched $C_1$-$C_4$ lower alkyl group which may be protected, a $C_3$-$C_6$ cycloalkyl group, a $C_2$-$C_4$ alkenyl or alkynyl group or a substituted or unsubstituted phenylmethyl or heterocyclic methyl group which may be protected, and W represents a protecting group of an enolic hydroxy group, a reactive derivative of the amino group thereof or a salt thereof is reacted with a compound represented by the following general formula (VIII):

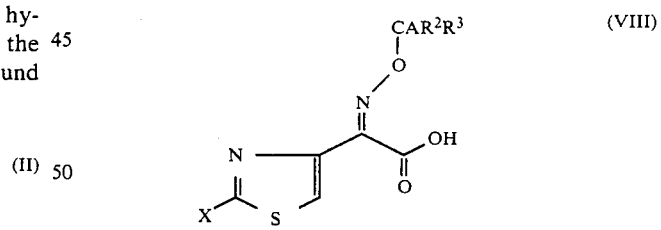

wherein A represents a hydrogen atom, an N-lower alkylcarbamoyl group, a carboxy group which may be protected or a carbamoyl group, $R^2$ and $R^3$ may be the same or different and independently represent a hydrogen atom or a $C_1$-$C_3$ lower alkyl group, and X represents an amino group which may be protected, a reactive derivative of the carboxy group thereof or a salt thereof, and if necessary, the protecting groups are eliminated from the reaction product.

The present invention is a process for producing a novel cephem compound represented by the general formula (I) wherein $R^4$ represents a hydrogen atom or a hydroxy group, characterized in that a compound represented by the general formula (VII'):

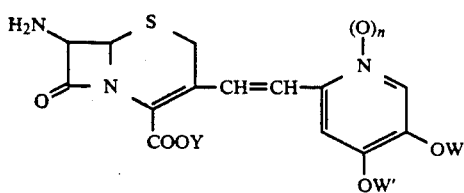

(VII')

wherein Y represents a hydrogen atom or a protecting group of a carboxy group, n denotes 0 or 1, W and W' may be the same or different and independently represent a protecting group of an enolic hydroxy group, a reactive derivative of the amino group thereof or a salt thereof is reacted with a compound represented by the following general formula (VIII):

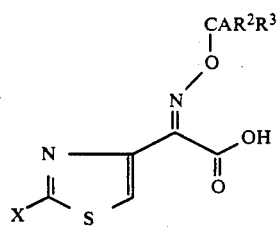

(VIII)

wherein A represents a hydrogen atom, an N-lower alkyl carbamoyl group, a carboxy group which may be protected or a carbamoyl group, $R^2$ and $R^3$ may be the same or different and independently represent a hydrogen atom or $C_1$–$C_3$ lower alkyl group, and X represents an amino group which may be protected, a reactive derivative of the carboxy group thereof or a salt thereof, and if necessary, the protecting groups are eliminated from the resulting product.

EFFECT

The novel cephem compound of the present invention has a wide range of strong anti-bacterial activities and is easily ingested with toxicity sustained at lower levels, so that it becomes possible to provide an excellent anti-bacterial agent.

The anti-bacterial activities of the compound according to the present invention will be described in detail in experimental examples hereinafter.

DETAILED DESCRIPTION OF THE INVENTION

Compound

The compound according to the present invention is represented by the general formula (I) described above.

The compound of the general formula (I) has cis- and trans-isomers depending on the configurations of a substituent at the substituted vinyl group which is a side chain at 3-position of the cephem ring. The present invention includes the cis- and trans-isomers and a mixture thereof. Stereochemistry of the oxime on the side chain at 7-position is a syn-isomer.

Moreover, the 1-substituted-5-hydroxy-4-pyridone portion of the 3-substituent is possible to have tautomers represented by the formulae (i), (ii) and (iii) depending on the types of $R^4$. The present invention includes all of these tautomers, although a pyridone type will be employed for the nomenclature and the description of a structural formula.

(i) in case that $R^4$ is a hydroxy group:

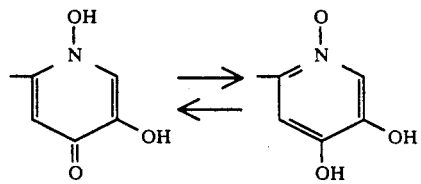

(ii) in case that $R^4$ is a hydrogen atom:

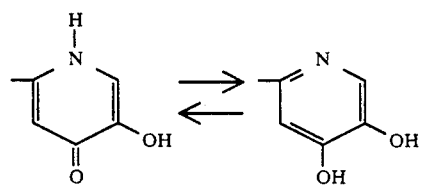

(iii) in case that $R^4$ is a group other than in (i) or (ii):

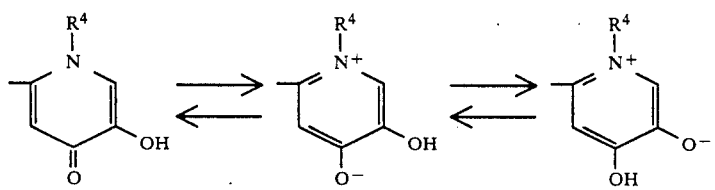

The substituent $R^1$ of the compound represented by the general formula (I) includes, for example (a) hydrogen; (b) a carboxy group; and (c) N-($C_1$–$C_3$) lower alkyl carbamoyl groups such as an N-methylcarbamoyl group, an N-ethylcarbamoyl group, an N-propylcarbamoyl group and the like.

The substituents $R^2$ and $R^3$ of the general formula (I), which may be the same or different, independently include, for example, (a) hydrogen, (b) $C_1$–$C_3$ lower alkyl groups such as methyl, ethyl, propyl, isopropyl or the like.

The substituent $R^4$ of the general formula (I) includes, for example (a) hydrogen, (b) a hydroxy group, (c) a straight chain or branched $C_1$–$C_4$ lower alkoxy group, (d) a substituted or unsubstituted straight chain or branched $C_1$–$C_6$ lower alkyl group, (e) a $C_3$–$C_6$ cycloalkyl group, (f) a $C_2$–$C_4$ alkenyl or alkynyl group, (g) a substituted or unsubstituted phenylmethyl or heterocyclic methyl group, or the like. By the term "substituted" of "substituted or unsubstituted" is included the case of a plurality of substituents.

As the examples of substituents of substituted or unsubstituted $C_1$–$C_4$ lower alkyl groups represented by $R^4$ of the compound having the general formula (I), there are mentioned (a) a hydroxy group, (b) lower alkoxy, preferably $C_1$–$C_3$ alkoxy groups such as a methoxy group, an ethoxy group and the like, (c) mono- and di-lower alkyl, preferably $C_1-C_3$ alkyl substituted groups such as an amino group, a methylamino group, a dimethylamino group and the like, (d) acyl groups such as a formyl group, an acetyl group and the like, (e) lower alkoxycarbonyl groups, (f) a carboxy group, (g) N-substituted (for example, lower alkyl substituted) or unsubstituted carbamoyl groups, (h) a cyano group, (i) halogen atoms such as a fluorine atom, a chlorine atom and the like, (j) a nitro group, (k) a sulfonic acid group, (l) a sulfonamide group, (m) a thiol group, (n) an alkylthio group, (o) an alkylsulfonyl group, (p) an alkylsulfinyl group, or the like.

Examples of substituents of substituted or unsubstituted phenylmethyl include (a) hydroxy group (b) methoxy group or (c) hydroxy group protected with p-methyoxybenzyl group or the like.

As the special examples of the heterocyclic group of the heterocyclic methyl group as an embodiment of $R^4$, there are mentioned a 2-furyl group, a 4-pyridyl group, a 1-methyl-4-pyridinio group, a 2-thienyl group, a 1H-tetrazol-5-yl group, a 1H-1-methyl-tetrazol-5-yl group, a 4-methylthiazol-5-yl group, a triazolyl group, a thiadiazolyl group, an imidazolyl group, an oxazolyl group and the like.

Accordingly, as an embodiment of $R^4$ of the compound having the formula (I) of the present invention, there are mentioned the following groups without limitation thereto: a methoxy group, a methyl group, an ethyl group, a propyl group, an isopropyl group, an n-butyl group, an isobutyl group, a sec-butyl group, a 2-hydroxyethyl group, a formylmethyl group, a 2,2-dimethoxyethyl group, an acetonyl group, a carboxymethyl group, a methoxycarbonylmethyl group, a 2-aminoethyl group, a 2-methylaminoethyl group, a dimethylaminoethyl group, a cyanomethyl group, a carbamoylmethyl group, a 2-nitroethyl group, 2,2,2-trifluoroethyl group, a methylthioethyl group, a cyclopropyl group, a cyclopropylmethyl group, a cyclobutyl group, an allyl group, a methallyl group, a crotyl group, a propargyl group, a benzyl group, a hydroxybenzyl group, a p-methoxybenzyl group, a 3,4-dimethoxybenzyl group, a 3,4-[di(P-methoxybenzyloxy)benzyl] group, a 2-furylmethyl group, a 4-pyridylmethyl group, a 1-methyl-4-pyridiniomethyl group, and the like.

Preferred embodiments of the compound represented by the formula (I) of the present invention, which embrace, as described above, the cis- or trans-isomers and a mixture of these isomers, include the following compounds without limitation thereto:

(a) (6R,7R)-7-[(Z)-2-(2-aminothiazol-4-yl)-2-methoxyiminoacetamido]-3-[2-(1,5-dihydroxy-4-pyridon-2-yl)-vinyl]ceph-3-em-4-carboxylic acid, (b) (6R,7R)-7-[(Z)-2-(2-aminothiazol-4-yl)-2-methoxyiminoacetamido]-3-[2-(5-hydroxy-1-methyl-4-pyridon-2-yl)vinyl]ceph-3-em-4-carboxylic acid, (c) (6R,7R)-7-[(Z)-2-(2-aminothiazol-4-yl)-2-methoxyiminoacetamido]-3-[2-(5-hydroxy-1-methoxy-4-pyridon-2yl)vinyl]ceph-3-em-4-carboxylic acid, (d) (6R,7R)-7-[(Z)-2-(2-aminothiazol-4-yl)-2-carboxymethoxyiminoacetamido]-3-[2-(1,5-dihydroxy-4-pyridon-2-yl)vinyl]ceph-3-em-4-carboxylic acid, (e) (6R,7R)-7-[(Z)-2-(2-aminothiazol-4-yl)-2-carboxymethoxyiminoacetamido]-3-[2-(5-hydroxy-1-methyl-4-pyridon-2-yl)vinyl]ceph-3-em-4-carboxylic acid, (f) (6R,7R)-7-[(Z)-2-(2-aminothiazol-4-yl)-2-(1-methyl-1-carboxy)ethoxyiminoacetamido]-3-[2-(1,5-dihydroxy-4-pyridon-2-yl)vinyl]ceph-3-em-4-carboxylic acid, (g) (6R,7R)-7-[(Z)-2-(2-aminothiazol-4-yl)-2-(1-methyl-1-carboxy)ethoxyiminoacetamido]-3-[2-(5-hydroxy-1-methyl-4-pyridon-2-yl)vinyl]ceph-3-em-4-carboxylic acid, (h) (6R,7R)-7-[(Z)-2-(2-aminothiazol-4-yl)-2-(1-methyl-1-carboxy)ethoxyiminoacetamido]-3-[2-(5-hydroxy-4-pyridon2-yl)vinyl]ceph-3-em-4-carboxylic acid, (i) (6R,7R)-7-[(Z)-2-(2-aminothiazol-4-yl)-2-(1-methyl-1-carboxy)ethoxyiminoacetamido]-3-[2-(5-hydroxy-1-(2-N,N-dimethylamino)ethyl)-4-pyridon-2-yl)vinyl]ceph-3-em-4carboxylic acid, (j) (6R,7R)-7-[(Z)-2-(2-aminothiazol-4-yl)-2-(1-methyl-1-carboxy)ethoxyiminoacetamido]-3-[2-(1-allyl-5-hydroxy-4-pyridon-2-yl)vinyl]ceph-3-em-4-carboxylic acid, (k) (6R,7R)-7-[(Z)-2-(2-aminothiazol-4-yl)-2-(1-methyl-1-carboxy)ethoxyiminoacetamido]-3-[2-(5-hydroxy-1-(2,2-dimethoxy)ethyl-4-pyridon-2-yl)vinyl]ceph-3-em-4carboxylic acid, (l) (6R,7R)-7-[(Z)-2-(2-aminothiazol-4-yl)-2-(1-methyl--1-carboxy)ethoxyiminoacetamido]-3-[2-(1-formylmethyl-5-hydroxy-4-pyridon-2-yl)vinyl]ceph-3-em-4-carboxylic acid, (m) (6R,7R)-7-[(Z)-2-(2-aminothiazol-4-yl)-2-(1-methyl-1-carboxy)ethoxyiminoacetamido]-3-[2-(5-hydroxy-1-isopropyl-4-pyridon-2-yl)vinyl]ceph-3-em-4-carboxylic acid, (n) (6R,7R)-7-[(Z)-2-(2-aminothiazol-4-yl)-2-(1-methyl-1-carboxy)ethoxyiminoacetamido]-3-[2-(5-hydroxy-1-methoxycarbonylmethyl-4-pyridon-2-yl)vinyl]-ceph-3-em-4carboxylic acid, (o) (6R,7R)-7-[(Z)-2-(2-aminothiazol-4-yl)-2-(1-methyl-1-carboxy)ethoxyiminoacetamido]-3-[2-(5-hydroxy-1-carbonylmethyl-4-pyridon-2-yl)vinyl]ceph-3-em-4carboxylic acid, (p) (6R,7R)-7-[(Z)-2-(2-aminothiazol-4-yl)-2-(1-methyl-1-carboxy)ethoxyiminoacetamido]-3-[2-(1-(2-furyl)-methyl-5-hydroxy-4-pyridon-2-yl)vinyl]ceph-3-em-4-carboxylic acid, (q) (6R,7R)-7-[(Z)-2-(2-aminothiazol-4-yl)-2-(1-methyl-1-carboxy)ethoxyiminoacetamido]-3-[2-(5-hydroxy-1-(4-pyridyl)-methyl-4-pyridon-2-yl)vinyl]ceph-3-em-4carboxylic acid, (r) (6R,7R)-7-[(Z)-2-(2-aminothiazol-4-yl)-2-(1-methyl-1-carboxy)ethoxyiminoacetamido]-3-[2-(5-hydroxy-1-(1-methyl-4-pyridinio)methyl-4-pyridon-2-yl)vinyl]ceph-3-em4-carboxylic acid, (s) (6R,7R)-7-[(Z)-2-(2-aminothiazol-4-yl)-2-(N-methylcarbamoyl)methoxyiminoacetamido]-3-[2-(1,5-dihydroxy-4-pyridon-2-yl)vinyl]ceph-3-em-4-carboxylic acid, (t) (6R,7R)-7-[(Z)-2-(2-aminothiazol-4-yl)-2-methoxyiminoacetamido]-3-[2-(5-hydroxy-1-(p-methoxybenzyl)-4-pyridon-2-yl)vinyl]ceph-3-em-4-carboxylic acid, (u) (6R,7R)-7-[(Z)-2-(2-aminothiazol-4-yl)-2-(1-methyl-1-carboxy)ethoxyiminoacetamido]-3-[2-(5-hydroxy-1-carboxy-4-pyridon-2-yl)vinyl]ceph-3-em-4-carboxylic acid, (v) (6R,7R)-7-[(Z)-2-(2-aminothiazol-4-yl)-2-(1-methyl-1-carboxy)ethoxyiminoacetamido]-3-[2-(5-hydroxy-1-(2-carboxyethyl)-4-pyridon-2-yl)vinyl]ceph-3-em-4-carboxylic acid, (w) (6R,7R)-7-[(Z)-2-(2-aminothiazol-4-yl)-2-(1-methyl-1-carboxy)ethoxyiminoacetamido]-3-[2-(5-hydroxy-1-(3-carboxypropyl) -4-pyridon-2-yl)vinyl]ceph-3-em4carboxylic acid, (x) (6R,7R)-7-[(Z)-2-(2-aminothiazol-4-yl)-2-(1-methyl-1-carboxy)ethoxyiminoacetamido]-3-[2-(5-hydroxy-1-(5-carboxypentyl)-4-pyridon-2-yl)vinyl]ceph-3-em-4carboxylic acid, (y) (6R,7R)-7-[(Z)-2-(2-aminothiazol-4-yl)-2-(1-methyl-1-carboxy)ethoxyiminoacetamido]-3-[2-(5-hydroxy-1-((1S)-carboxyethyl)-4-pyridon-2-yl)vinyl]ceph-3-em-4-carboxylic acid (trans-isomer) and (6R,7R)-7-[(Z)-2-(2-aminothiazol4-yl)-2-(1-methyl-1-carboxy)ethoxyiminoacetamido]-3-[2(5-hydroxy-1-((1R)-1-carboxyethyl)-4-pyridon-2yl)vinyl]ceph-3-em-4-carboxylic acid, (z) (6R,7R)-7-[(Z)-2-(2-aminothiazol-4-carboxy)ethoxyiminoacetamido]-3-[2-(5-hydroxy-1-(α-carboxybenzyl)-4-pyridon-2-yl)vinyl]ceph-3-em-4carboxylic acid, (a') (6R,7R)-7-[(Z)-2-(2-aminothiazol-4-yl)-2-(1-methyl-1-carboxy)ethoxyiminoacetamido]-3-[2-(5-hydroxy-1-(N,N)-dimethylaminocarbonylmethyl)-4-pyridon-2-yl)vinyl]ceph-3-em-4-carboxylic acid, (b') 2-{3-{2-{(6R,7R)-7-[(Z)-2-(2-aminothiazol-4-yl)-2-(1-methyl-1-carboxy)ethoxyiminoacetamido]-4-carboxyceph-3-em-3-yl]vinyl]-5-hydroxy-4-pyridon-1-yl]ethanesulfonic acid, and (c') (6R,7R)-7-[(Z)-2-(2-aminothiazol-4-yl)-2-(1-methyl-1-carboxy)ethoxyiminoacetamido]-3-{2-(5-hydroxy-1-(3,4-dihydroxybenzyl)-4-pyridon-2-yl]vinyl}ceph-3-em-4-carboxylic acid.

As the pharmacologically acceptable salts of the compounds represented by the formula (I) of the present invention, there are mentioned medically acceptable salts, in particular commonly used non-toxic salts, for example, alkali metal salts such as a sodium salt, a potassium salt and the like; alkaline earth metal salts such as a calcium salt, a magnesium salt and the like; an ammonium salt; salts with organic bases such as organic amine salts, for example a triethylamine salt, a pyridine salt, an ethanolamine salt, a triethanolamine salt, a dicyclohexylamine salt and the like; and basic amino acid salts such as a lysine salt and an arginine salt.

Preparation of the Compounds (Part 1)

The compound (I) according to the present invention can be synthesized by any appropriate methods suitable for the desired purposes.

A specific example of the appropriate synthesis method can be illustrated as follows:

The compound (I) can be prepared by reacting the compound (II)

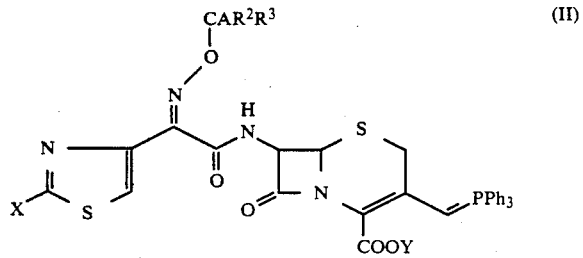

wherein A has the same meanings as $R^1$ or represents a protected carboxy group, $R^2$ and $R^3$ have the same meanings as defined above, X represents an amino group or a protected amino group, and Y represents a protecting group of a carboxyl group, with the compound (III)

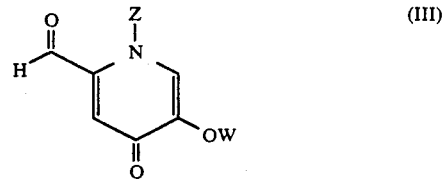

wherein Z has the same meanings as $R^4$ or represents a group which can be optionally converted into the aforementioned group $R^4$ by eliminating the protecting group, and W represents an enolic hydroxy-protecting group, and if necessary, eliminating the protecting groups by a conventional method.

The term "protecting group" of the amino group of the phosphorane (II) means a conventional amino protecting group which can readily be eliminated by acid hydrolysis or other procedures, for example an alkoxycarbonyl group such as a tert-butoxycarbonyl group; acyl groups such as a formyl group and a chloroacetyl group; a trityl group and the like.

As the carboxy-protecting group Y, there are mentioned protecting groups usually employed for cephalosporins such as a p-methoxybenzyl group, a diphenylmethyl group, a p-nitrobenzyl group, an aryl group, a lower alkyl group, a lower alkoxymethyl group, a lower alkylthiomethyl group, a lower alkanoyloxymethyl group and the like. It also includes metabolically unstable protecting groups, which can be hydrolyzed in an organism and eliminated therefrom, such as a lower alkoxycarbonyloxyalkyl group and a (2-oxo-1,3-dioxoren-4yl)methyl group which may be substituted.

An example of protecting groups which are used for the protected carboxy group as an embodiment of A includes the same groups as Y.

In the aldehyde (III), the group Z which optionally can be converted into the aforementioned $R^4$ by eliminating the protecting group represents, for example in case that the group represented by the aforementioned group $R^4$ has an amino group or a carboxy group a side chain of which the amino group or carboxy group is protected by a required protecting group usually used in cephalosporins. These protecting groups include as the amino-protecting group an alkoxycarbonyl group such as a tert-butoxycarbonyl group; an acyl group such as a formyl group or a chloroacetyl group; or conventional amino-protecting groups which can be readily eliminated for example by acid hydrolysis such as a trityl group. As the protecting group of the carboxy group, there are mentioned protecting groups usually used for cephalosporins such as a p-methoxybenzyl group, a diphenylmethyl group, a p-nitrobenzyl group, an aryl group, a lower alkyl group, a lower alkoxymethyl group, a lower alkylthiomethyl group, a lower alkanoyloxymethyl group or the like. As the enolic hydroxy-protecting group W, there can be used the protecting groups which are usually used as a carboxyprotecting group in cephalosporins such as a p-methoxybenzyl group, a diphenylmethyl group, a p-nitrobenzyl group, an aryl group, a lower alkyl group, a lower alkoxymethyl group, a lower alkylthiomethyl group, a lower alkanoyloxymethyl group or the like as well as an acyl group such as an acetyl group, a pivaloyl group, a benzoyl group or the like.

The compound of the formula (I) wherein $R^4$ is a hydrogen atom or a hydroxy group according to the present invention can be prepared by reacting the phosphorane (II) with a compound represented by the formula (III)'

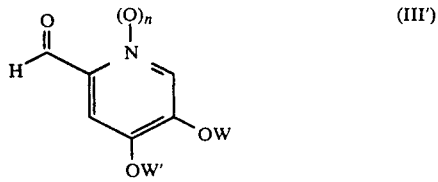

wherein n denotes 0 or 1, W and W' may be the same or different and independently an enolic hydroxy-protecting group, instead of the aldehyde (III) under the same conditions, and if necessary eliminating the protecting groups as usual.

As the enolic hydroxy-protecting groups W and W', there can be used those which are usually used as a carboxy-protecting group in cephalosporins, such as a p-methoxybenzyl group, a diphenylmethyl group, a p-nitrobenzyl group, an aryl group, a lower alkyl group, a lower alkoxymethyl group, a lower alkylthiomethyl group, a lower alkanoyloxymethyl group or the like as well as an acyl group such as an acetyl group, a pivaloyl group, a benzoyl group or the like.

The phosphorane represented by the formula (II) can be prepared by reacting a compound represented by the formula (IV):

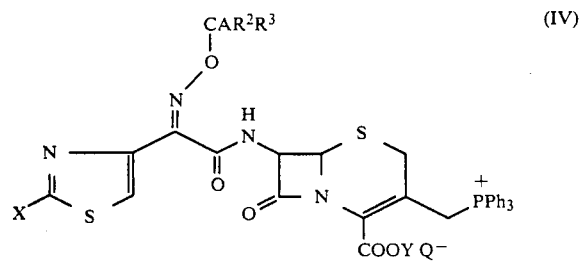

wherein A, $R^2$, $R^3$, X and Y have the same meanings as defined above, and Q represents a salt-forming anion, with an inorganic or organic base.

The salt-forming anion Q includes inorganic anions such as a chloride ion, a bromide ion, an iodide ion, a ½ sulfate ion, a hydrogen sulfate ion, a nitrate ion, a phosphate ion or the like; and organic sulfonate or carboxylate anions such as a p-toluenesulfonate ion, a methanesulfonate ion, an oxalate ion, an acetate ion, a trifluoroacetate ion, a formate ion or the like.

The inorganic or organic bases include alkali metal hydroxides such as sodium hydroxide, potassium hydroxide or the like; alkaline earth metal hydroxides such as calcium hydroxide or the like; alkali metal hydrogen carbonates such as sodium hydrogen carbonate, potassium hydrogen carbonate or the like; alkali metal carbonates such as sodium carbonate, potassium carbonate or the like; alkaline earth metal carbonates such as calcium carbonate or the like; tri-(lower) alkylamines such as triethylamine, trimethylamine or the like; pyridine; N-(lower) alkylmorpholines; N,N-di(lower) alkylbenzylamines or the like.

The reaction is generally carried out in a usually used solvent such as water, acetone, ethanol, propanol, methanol, dioxane, acetonitrile, chloroform, methylene chloride, tetrahydrofuran, ethyl acetate, N,N-dimethylformamide or pyridine, or a mixed solvent thereof. The reaction can be also carried out in the other organic solvent which will not affect detrimentally it. These solvents may be used as an admixture with water or as a dual phase type solvent. Reaction temperature is not particularly limited, and the reaction is usually carried out under a cooling or warming condition. The phosphorane (II) thus obtained is isolated or not isolated and is subjected to the reaction with the aldehyde (III) or (III').

The aldehyde (III) can be synthesized, for example, according to the following process:

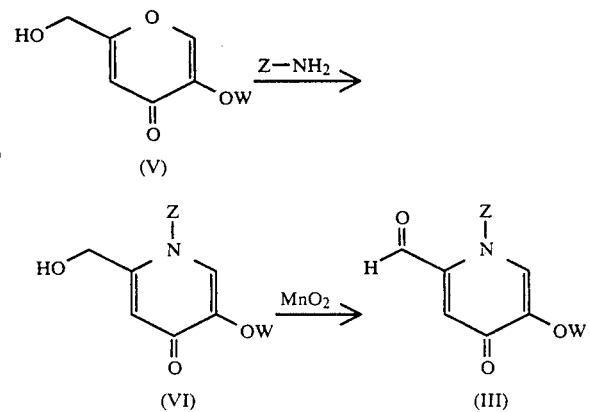

wherein W and Z have the same meanings as defined above. In other words, the kojic acid derivative (V) is reacted with $Z-NH_2$ such as ammonia, a primary amine or a hydroxylamine to form the pyridone derivative (IV), which is then reacted with manganese dioxide to oxidize the hydroxymethyl group on the side chain and thus to give the aldehyde (III). This method is not intended to limit the synthetic methods of the aldehyde (III).

The reaction of the phosphorane (II) and the aldehyde (III) or (III') is generally carried out in a usually used solvent such as water, acetone, ethanol, propanol, methanol, dioxane, acetonitrile, chloroform, methylene chloride, tetrahydrofuran, ethyl acetate, N,N-dimethylformamide or pyridine, or a mixed solvent thereof. The reaction can be also carried out in the other organic solvent which will not affect detrimentally it. These solvents may be used as an admixture with water or as a dual phase type solvent. Reaction temperature is not particularly limited, and the reaction is usually carried out under a cooling or warming condition.

The product thus obtained is usually the one in which the amino group and the carboxy group as well as the hydroxy groups on the pyridone or pyridine ring of the objective compound (I) of the present invention are protected, and thus the protecting groups of the product are independently eliminated by the conventional methods. The methods for eliminating the carboxy-protecting group and the amino-protecting group are selected appropriately depending on the kinds of the protecting groups to be eliminated. In order to eliminate the amino-protecting group, hydrolysis or reduction is employed. As for the compound protected with an acyl group, the compound is reacted with an iminohalogenating agent followed by an iminoetherizing agent, and if necessary, any conventional method can be used such as hydrolysis or the like. Acid hydrolysis is one of the usual methods and can be applied for eliminating such groups as an alkoxycarbonyl group, a formyl group, a trityl group or the like. As the acid used for the hydrolysis, formic acid, trifluoracetic acid, hydrochloric acid or the like is appropriately selected depending on the types of the amino-protecting groups. The reaction can be carried out either in the absence of solvent or in the presence of water, a hydrophilic organic solvent or a mixed solvent thereof. If trifluoroacetic acid is used, the reaction may be performed in the presence of anisole. In order to eliminate the carboxy-protecting group, any conventional method such as hydrolysis or reduction can be employed. Acid hydrolysis is one of the usual methods and can be used for eliminating a protecting group such as a silyl group, a p-methoxybenzyl group or a diphenylmethyl group or the like. Also, to the elimination reaction of the hydroxy-protecting groups on the pyridone or pyridine ring can be applied any conventional methods such as hydrolysis, reduction or the like. Acid or base hydrolysis is one of the usual methods. For example, an acid is applied to the elimination of a p-methoxybenzyl group, a diphenylmethyl group or the like, and a base is applied to the elimination of acyl groups such as an acetyl group, a benzoyl group or the like.

Preparation of the Compounds (Part 2)

Another example of the preferred method for synthesizing the compound (I) according to the present invention can be illustrated as follows:

It can be prepared by reacting the compound represented by the formula (VII):

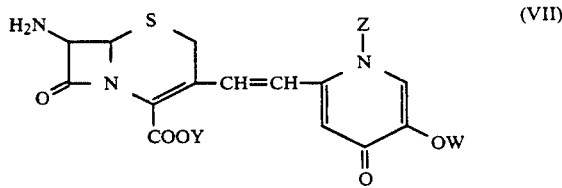

(VII)

wherein W and Z have the same meanings as defined above, Y has the same meanings as defined above or represents a hydrogen atom, or in order to prepare the compound (I) of the present invention wherein $R^4$ represents a hydrogen atom or a hydroxy group the compound represented by the formula (VII) or the following formula (VII'):

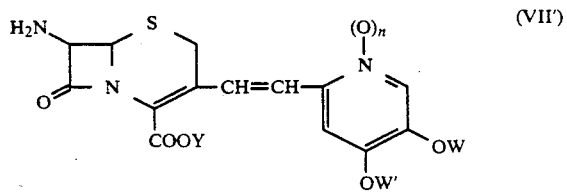

(VII')

wherein W and W' have the same meanings as defined above, and Y has the same meanings as defined above or represents a hydrogen atom, a reactive derivative at the amino group thereof or a salt thereof with the compound represented by the formula (VIII):

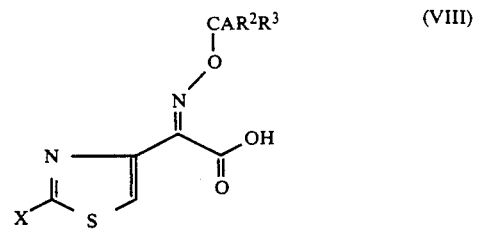

(VIII)

wherein A, $R^2$, $R^3$ and X are the same meanings as defined above, reactive derivative at the carboxy group thereof or a salt thereof. As the appropriate examples of the reactive derivative at the amino group of the compound (VII) or (VII'), there are mentioned an imino type isomer which is a Schiff's base type resulting from the reaction of the compound (VII) or (VII') with a carbonyl compound such as aldehyde or ketone or a tautomeric enamine type isomer thereof, or a derivative produced by the reaction of the compound (VII) or (VII') with a silyl derivative such as bis(trimethylsilyl)acetamide or the like or by the reaction of the compound (VII) or (VII') with phosphor trichloride or phosgene.

As the appropriate salts of the compounds of (VII) or (VII') and (VIII), there are mentioned acid addition salts, for example salts with organic acids such as an acetic acid salt, a maleic acid salt, a tartaric acid salt, a benzenesulfonic acid salt, a toluenesulfonic acid salt and the like, or salts with inorganic acids such as a hydrochloride salt, a hydrobromic acid salt, a sulfuric acid salt, a phosphoric acid salt and the like; metal salts, for example alkali metal salts or alkaline earth metal salts such as a sodium salt, a potassium salt, a calcium salt, a magnesium salt and the like; ammonium salts; and organic amine salts such as a triethylamine salt, a dicyclohexylamine salt and the like.

As the appropriate examples of the reactive derivatives at the carboxy group of the compound (VIII), there are mentioned acid halides, acid azides, acid anhydrides, active amides, active esters and the like, more particularly acid chloride; acid bromides; mixed acid anhydrides with an acid such as substituted phosphoric acids such as dialkylphosphoric acids, dibenzylphosphoric acid, halogenated phosphoric acids and the like, dialkylphosphorous acids, sulfurous acid, thiosulfuric acid or sulfuric acid, alkylcarbonic acids such as methylcarbonic acid, ethylcarbonic acid and the like, aliphatic carboxylic acids such as pivalic acid, valeric acid, isovaleric acid, 2-ethylacetic acid, trichloroacetic acid or the like or with aromatic carboxylic acids such as benzoic acid; active amides with imidazole, dimethylpyrazole, triazole or tetrazole; or active esters such as a cyanomethyl ester, a methoxymethyl ester, a dimethyliminomethyl ester, a vinyl ester, a propargyl ester, a p-nitrophenyl ester, a 2,4-dinitrophenyl ester, a trichlorophenyl ester, a pentachlorophenyl ester, a mesylphenyl ester, a phenylazophenyl ester, a phenylthio ester, a p-nitrophenylthio ester, a p-cresylthio ester, a carboxymethylthio ester, a pyranyl ester, a pyridyl ester, a piperidyl ester, an 8-quinolylthio ester or the like; or esters with N-hydroxy compounds such as N,N-dimethylhydroxyamine, 1-hydroxy-2-(1H)-pyridone, N-hydroxysuccinimide, N-hydroxyphthalimide, 1-hydroxy-6-chloro-1H-benzotriazole or the like. These reactive derivatives are appropriately selected depending on the kinds of the reactant compounds (VIII) to be used.

The reaction of the compound (VII) or (VII') and the compound (VIII) is generally carried out in a usually used solvent such as water, acetone, dioxane, acetonitrile, chloroform, methylene chloride, tetrahydrofuran, ethyl acetate, N,N-dimethylformamide or pyridine, or a mixed solvent thereof. The reaction can be also carried out in the other organic solvent which will not affect detrimentally it. These solvents may be used as an admixture with water.

In the reaction, when the compound (VIII) is used in the form of a free acid or a salt thereof, the condensation agent includes the so-called Willsmeyer reagent which is obtained by the reaction of N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N-carbonylbis(2-methylimidazole), pentamethyleneketen-N-cyclohexylimine, diphenylketen-N-cyclohexylimine, ethoxyacetylene, a 1-alkoxy-1-chloroethylene, a trialkyl phosphite, ethyl polyphosphate, isopropyl polyphosphate, phosphorus oxychloride, phosphorus trichloride, thionyl chloride, oxalyl chloride, triphenylphosphine, a 2-ethyl-7-hydroxy benzisoxazolium salt, 2-ethyl-5-(m-sulfophenyl)isoxazolium hydroxide intramolecular salt, 1-(p-chlorobenzenesulfonyloxy)-6-chloro-1H-benzotriazole or dimethylformamide with thionyl chloride, phosgene, phosphorus oxychloride or the like.

The reaction may be carried out in the presence of an inorganic or organic base. Such a base includes alkali metal hydrogen carbonates such as sodium hydrogen carbonate, potassium hydrogen carbonate or the like; alkaline earth metal carbonates such as calcium carbonate or the like; tri-(lower) alkylamines such as triethylamine, trimethylamine or the like; pyridine; N-(lower) alkylmorpholines; N,N-di-(lower) alkylbenzylamines or the like.

Reaction temperature is not limited and is usually carried out under a cooling or warming condition.

The product obtained by the second process is the objective compound (I) of the present invention or the one in which the amino group and the carboxy group as well as the hydroxy groups on the pyridone or pyridine ring of the objective compound (I) of the present invention are protected. Thus, if necessary, the protecting groups of the product are independently eliminated by the conventional methods. The methods for eliminating the carboxy-protecting group and the amino-protecting group are selected appropriately depending on the kinds of the protecting groups to be eliminated. In order to eliminate the amino-protecting group, hydrolysis or reduction is employed. As for the compound protected with an acyl group, the compound is reacted with an iminohalogenating agent followed by an iminoetherizing agent, and if necessary, any conventional method can be used such as hydrolysis or the like. Acid hydrolysis is one of the usual methods and can be applied for eliminating such groups as an alkoxycarbonyl group, a formyl group, a trityl group or the like. As the acid used for the hydrolysis, formic acid, trifluoroacetic acid, hydrochloric acid or the like is appropriately selected depending on the types of the amino-protecting groups. The reaction can be carried out either in the absence of solvent or in the presence of water, a hydrophilic organic solvent or a mixed solvent thereof. If trifluoroacetic acid is used, the reaction may be performed in the presence of anisole. In order to eliminate the carboxy-protecting group, any conventional method such as hydrolysis or reduction can be employed. Acid hydrolysis is one of the usual methods and can be used for eliminating a protecting group such as a silyl group, a p-methoxybenzyl group or a diphenylmethyl group. Also, to the elimination reaction of the hydroxy-protecting groups on the pyridone or pyridine ring can be applied any conventional methods such as hydrolysis, reduction or the like. Acid or base hydrolysis is one of the usual methods. An acid is applied to the elimination of a p-methoxybenzyl group, a diphenylmethyl group or the like, and a base is applied to the elimination of acyl groups such as an acetyl group, a benzoyl group or the like.

The compound represented by the general formula (I) thus obtained is taken out from the reaction mixture by the usual method.

For instance, the recovery of the compound (I) is accomplished by combining appropriately procedures of purification, precipitation, crystallization and the like using absorptive resins such as Amberlite XAD-2 (manufactured by Rohm & Haas Co.), DIAION HP-20 or SEPABEADS SP207 (manufactured by Mitsubishi Chemical Industries Ltd.).

Usefulness of the Compounds/Anti-bacterial Agents

The anti-bacterial agent comprising as a main component the compound represented by the general formula (I) or a salt thereof is primarily used in various forms of preparations, for example injections such as intravenous injection, intramuscular injection, or the like; oral drugs such as capsule, tablet, powder or the like; or drugs for rectal application, suppositories with oil and fat property, water soluble suppositories or the like. These various preparations can be prepared in a usual method using an excipient, an extender, a binder, a wetting agent, a disintegrating agent, a surfactant, a lubricant, a dispersant, a buffering agent, a preservative, a dissolution adjuvant, an antiseptic, a flavorant, an aponic agent or the like. Embodiments of drug preparation will be described in detail in examples hereinafter.

Dosage is appropriately determined respectively in consideration of factors such as conditions, ages or sex of patients, and is generally in the range of 250–3000 mg/day, which is administered in 1–4 doses.

EXPERIMENTAL EXAMPLE

The present invention will be explained in detail in the following Synthesis Examples and Examples without limitation of the invention.

SYNTHESIS EXAMPLE 1

3-diphenylmethoxy-6-hydroxymethyl-1-methyl-4-pyridone

To a solution of 3.035 g of 3-diphenylmethoxy-6-hydroxymethyl-4-pyrone in 20 ml of methanol is added 50 ml of 40% aqueous methylamine solution, and the mixture is stirred for 4 hours. The reaction mixture is condensed under reduced pressure to a volume of 15 ml, and the resulting crystal is collected by filtration, washed with a small amounts of water and ethyl acetate in this sequence, and dried under reduced pressure to give 2.04 g of the title compound.

NMR ((CD$_3$)$_2$SO) δ: 3.46 (3H,s), 4.27 (2H,d,J=5Hz), 5.44 (1H,t,J=5Hz), 6.19 (1H,s), 6.72 (1H,s), 7.1–7.5 (10H,m), 7.46 (1H,s).

SYNTHESIS EXAMPLE 2

3-diphenylmethoxy-6-formyl-1-methyl-4-pyridone

To 350 ml of a methanol solution of 1.731 g of 3-diphenyl-6-hydroxymethyl-1-methyl-4-pyridone is added 10.4 g of manganese dioxide, and the mixture is stirred for 2 hours. Inorganic materials are filtered off from the reaction mixture and washed with a small amount of methanol. The filtrate was condensed under reduced pressure, and 300 ml of chloroform is added to the condensate. After stirring insolubles are removed by filtration, and the filtrate was washed with saturated aqueous sodium hydrogen carbonate solution, dried over magnesium sulfate, condensed under reduced pressure. The resulting crystal is washed with a mixed solvent of ethyl acetate-isopropyl ether (1:1) and dried under reduced pressure to give 1.42 g of the title compound.

NMR (CDCl$_3$) δ: 3.74 (3H,s), 6.82 (1H,s), 6.90 (1H,s), 6.94 (1H,s), 7.1–7.5 (10H,m), 9.54 (1H,s).

SYNTHESIS EXAMPLE 3

6-hydroxymethyl-3-(p-methoxybenzyl)oxy-1-(p-methoxybenzyl)-4-pyridone and 6-hydroxymethyl-3,4-bis[(p-methoxybenzyl)oxy]-pyridine To a suspension of 2.613 g of 6-hydroxymethyl-3-(p-methoxybenzyl)oxy-4-pyridone in 100 ml of dimethylformamide were added sequentially 2.073 g of potassium carbonate and 2.35 g of p-methoxybenzyl chloride, and the mixture is stirred at room temperature for 40 hours. The reaction mixture is added to 200 ml of water and 400 ml of dichloromethane, and the organic layer is washed with 200 ml of water. The organic layer is dried over anhydrous magnesium sulfate, condensed under reduced pressure and subjected to flash column chromatography on 100 g of Wako-Gel C-300 (manufactured by Wako Pure Chemical Industries, Ltd.) with an eluent of chloroformmethanol (20:1) to perform separation and purification. 6-hydroxymethyl-3-(p-methoxybenzyl)oxy-1-(p-methoxybenzyl)-4-pyridone and 6-hydroxymethyl-3,4-bis[(p-methoxybenzyl)oxy]-pyridine are obtained as colorless crystals in amounts of 1.749 g and 1.527 g, respectively. 6-hydroxymethyl-3-(p-methoxybenzyl)oxy-1-(p-methoxybenzyl)-4-pyridone;

NMR ((CD$_3$)$_2$SO) δ: 3.71 (3H,s), 3.73 (3H,s), 4.24 (2H,d,J=6Hz), 4.92 (2H,s), 5.02 (2H,s), 5.56 (1H,t,J=6Hz), 6.21 (1H,s), 6.7–7.0 (6H,m), 7.2–7.3 (2H,m), 7.47 (1H,s).

6-hydroxymethyl-3,4-bis[(p-methoxybenzyl)oxy]-pyridine;

NMR ((CD$_3$)$_2$SO) δ: 4.71 (3H,s), 3.73 (3H,s), 4.41 (2H,d,J=6Hz), 5.01 (2H,s), 5.08 (2H,s), 6.7–7.0 (4H,m), 7.14 (1H,s), 7.2–7.5 (4H,m), 8.30 (1H,s).

SYNTHESIS EXAMPLE 4

6-formyl-3-(p-methoxybenzyl)oxy-1-(p-methoxybenzyl)-4-pyridone

From 1.340 g of 6-hydroxymethyl-3-(p-methoxybenzyl)-oxy-1-(p-methoxybenzyl)-4-pyridone is obtained 1.044 g of the title compound as colorless crystal in the same manner as in Synthesis Example 2.

NMR (CDCl$_3$) δ: 3.76 (3H,s), 3.77 (3H,s), 5.13 (2H,s), 5.35 (2H,s), 6.7–6.9 (6H,m), 6.95 (1H,s), 7.08 (1H,s), 7.2–7.3 (2H,m), 9.54 (1H,s).

SYNTHESIS EXAMPLE 5

4-acetoxy-6-formyl-3-(p-methoxybenzyl)oxypyridine

To a solution of 0.05 g of 6-formyl-3-(p-methoxybenzyl)oxy-4-pyridone in 5 ml of pyridine is added 0.133 g of acetic anhydride, and the mixture is stirred for 2 hours. The reaction mixture is condensed under reduced pressure, and the residue is dissolved in 20 ml of methylene chloride, washed with water, 5% aqueous potassium hydrogen sulfatge solution and 7% aqueous sodium hydrogen carbonatge solution in this sequence, dried over magnesium sulfate, and condensed to dryness under reduced pressure to give 0.318 g of the title compound as colorless crystal.

NMR (CDCl$_3$) δ: 2.27 j(3H,s), 3.78 (3H,s), 5.18 (2H,s), 6.8–6.9 (2H,m), 7.2–7.3 (2H,m), 7.66 (1H,s), 8.44 (1H,s), 9.88 (1H,s).

SYNTHESIS EXAMPLE 6

3-diphenylmethoxy-1-(2-dimethylaminoethyl)-6-hydroxymethyl-4-pyridone

To a suspension of 1.542 g of 6-hydroxymethyl-3-(p-methoxybenzyl)oxy-4-pyridone in 10 ml of methanol is added 4.408 g of N,N-dimethylethylenediamine, and the mixture is stirred for 14 hours. The reaction mixture is condensed under reduced pressure, and subjected to flash column chromatography on 50 g of Wako-Gel C-300 (manufactured by Wako Pure Chemical Industries, Ltd.) with an eluent of chloroform-methanol (10:1) to perform separation and purification. The title compound is obtained as colorless crystal in a yield of 1.174 g.

NMR (CDCl$_3$) δ: 2.00 (6H,s), 2.2 (1H,broad s), 2.34 (2H,t,J=6Hz), 3.80 (2H,t,J=6Hz), 4.30 (2H,s), 6.28 (1H,s), 6.58 (1H,s), 6.89 (1H,s), 7.1–7.6 (10H,m).

SYNTHESIS EXAMPLE 7

3-diphenylmethoxy-1-(2-dimethylaminoethyl)-6-formyl-4pyridone

To a solution of 1.160 g of 3-diphenylmethoxy-1-[2(dimethylamino)ethyl]-6-hydroxymethyl-4-pyridone is added 6.0 g of manganese dioxide at room temperature, and the mixture is stirred for 3 hours. Insolubles are removed by filtration, and the filtrate was subjected to flash column chromatography on 50 g of Wako-Gel C-300 (manufactured by Wako Pure Chemical Industries, Ltd.) with an eluent of chloroform-methanol (10:1) to perform separation and purification. The title compound is obtained as colorless crystal in a yield of 0.744 g.

NMR (CDCl$_3$) δ: 2.05 (6H,s), 2.31 (2H,t,J=6Hz), 4.14 (2H,t,J=6Hz), 6.73 (1H,s), 6.85 (1H,s), 6.98 (1H,s), 7.1–7.5 (10H,m), 9.43 (1H,s).

SYNTHESIS EXAMPLE 8

3-diphenylmethoxy-1-(2,2-dimethoxyethyl)-6-hydroxymethyl-4-pyridone

To a suspension of 3.33 g of 6-hydroxymethyl-3-(p-methoxybenzyl)oxy-4-pyridone in 20 ml of methanol is added 11.35 g of 2,2-dimethoxyethylamine at room temperature, and the mixture is stirred for 3 days. The reaction mixture is condensed under reduced pressure, and subjected to flash column chromatography on 100 g of Wako-Gel C-300 (manufactured by Wako Pure Chemical Industries, Ltd.) with an eluent of chloroform-methanol (20:1) to perform separation and purification. The title compound is obtained as colorless foam in a yield of 2.062 g.

NMR (CDCl$_3$) δ: 3.13 (6H,s), 3.3 (1H,broad s), 3.85 (2H,d,J=5Hz), 4.25 (1H,t,J=5Hz), 4.35 (2H,s), 6.15 (1H,s), 6.50 (1H,s), 7.01 (1H,s), 7.1–7.5 (10H,m).

SYNTHESIS EXAMPLE 9

3-diphenylmethoxy-1-(2,2-dimethoxyethyl)-6-formyl-4pyridone

Starting from 2.052 g of 3-diphenylmethoxy-1-(2,2-dimethoxyethyl)-6-hydroxymethyl-4-pyridone and 12.0 g of manganese dioxide, the title compound is obtained in the same manner as in Synthesis Example 2 as colorless crystal in a yield of 1.582 g.

NMR (CDCl$_3$) δ: 3.23 (6H,s), 4.17 (3H,s), 6.73 (1H,s), 6.89 (1H,s), 7.06 (1H,s), 7.1–7.5 (10H,m), 9.51 (1H,s).

SYNTHESIS EXAMPLE 10

1-allyl 3-diphenylmethoxy-6-hydroxymethyl-4-pyridone

To a suspension of 1.542 g of 6-hydroxymethyl-3-(p-methoxybenzyl)oxy-4-pyridone in methanol is 5.710 g of allylamine at room temperature, and the mixture is stirred for 14 hours. After condensing at reduced pressure, 20 ml of ethyl acetate is added to the residue to perform crystallization. After the mixture is left standing at 4° C. for 4 hours, the crystal is collected by filtration, washed with a small amount of ethyl acetate and dried under reduced pressure to give 1.050 g of the title compound.

NMR (CDCl$_3$) δ: 1.7 (1H,broad), 4.30 (2H,s), 4.4–4.5 (2H,m), 4.55 (1H,d,J=16Hz), 4.98 (1H,d,J=13 Hz), 5.5–5.9 (1H,m), 6.22 (1H,s), 6.57 (1H,s), 6.85 (1H,s), 7.1–7.5 (10H,m).

SYNTHESIS EXAMPLE 11

1-allyl-3-diphenylmethoxy-6-formyl-4-pyridone

Starting from 1.000 g of 1-allyl-3-diphenylmethoxy-6-hydroxymethyl-4-pyridone and 6.00 g of manganese dioxide, the title compound is obtained in the same manner as in Synthesis Example 2 as colorless crystal in a yield of 0.710 g.

NMR (CDCl$_3$) δ: 4.6–4.9 (2H,m) , 4.80 (1H,d,J=13Hz), 6.77 (1H,s), 6.93 (1H,s), 6.96 (1H,s), 7.1–7.5 (10H,m), 9.51 (1H,s).

SYNTHESIS EXAMPLE 12

Sodium (3-diphenylmethoxy-6-hydroxymethyl-4-pyridon-1-yl)acetate

To a suspension of 3.083 g of 3-diphenylmethoxy-6-hydroxymethyl-4-pyrone in 100 ml of methanol is added 30 ml of an aqueous solution of a sodium salt of glycine prepared from 7.507 g of glycine and 4.00 g of sodium hydroxide at room temperature, and the mixture is stirred for 5 days. The reaction mixture is condensed under reduced pressure, and the resulting crystal is collected by filtration, washed with a small amount of water, and dried under reduced pressure to give 3.102 g of the title compound.

NMR ((CD$_3$)$_2$SO) δ: 4.30 (2H,s), 4.27 (2H,s), 5.73 (1H,broad s), 6.16 (1H,s), 6.71 (1H,s), 7.1–7.5 (1H,m).

SYNTHESIS EXAMPLE 13

Methyl (3-diphenylmethoxy-6-formyl-4-pyridon-1-yl)acetate

To a suspension of 3.100 g of sodium (3-diphenylmethoxy-6-hydroxymethyl-4-pyridon-1-yl)acetate in dichloromethane (60 ml)-water (60 ml) is added 3.02 g of diphenyldiazomethane, and the mixture is adjusted to a pH of 3 with 3N HCl under ice-cooling. The reaction mixture is further stirred at room temperature for 1 hour, and the organic layer is separated, dried over anhydrous magnesium sulfate and condensed to dryness under reduced pressure. The residue is dissolved in 80 ml of methanol, and 15.0 g of manganese dioxide is added. The mixture is stirred for 2 hours. Insolubles are removed by filtration, and the filtrate is condensed under reduced pressure. The residue is subjected to flash column chromatography on 150 g of Wako-Gel C-300 (manufactured by Wako Pure Chemical Industries, Ltd.) with an eluent of chloroform-methanol (20:1) to perform separation and purification. The title compound (1.504 g) is obtained as colorless crystal.

NMR (CDCl$_3$) δ: 3.67 (3H,s), 4.75 (2H,s), 6.71 (1H,s), 6.84 (1H,s), 6.90 (1H,s), 7.1–7.5 (10H,m), 9.43 (1H,s).

SYNTHESIS EXAMPLE 14

Diphenylmethyl (3-diphenylmethoxy-6-formyl-4-pyridon-1-yl)acetate

To a solution of 2.000 g of sodium (3-diphenylmethoxy-6-hydroxymethyl-4-pyridon-1-yl)acetate in 250 ml of methanol is added 12 g of active manganese dioxide at room temperature, and the mixture is stirred for 2 hours. After insolubles are removed by filtration, the filtrate is condensed under reduced pressure to a volume of 50 ml. Insolubles are again removed by filtration, and the filtrate is condensed to dryness. The residue is suspended in dichloromethane (200 ml)-water (50 ml), and 1.21 g of diphenyldiazomethane is added to the suspension. The mixture is adjusted to pH 3 with a saturated aqueous potassium hydrogen sulfate solution under ice-cooling. The reaction mixture is further stirred at room temperature for 2 hours, and the organic layer is separated, dried over anhydrous magnesium sulfate and condensed to dryness under reduced pressure. The residue is subjected to flash column chromatography on 120 g of Wako-Gel C-300 (manufactured by Wako Pure Chemical Industries, Ltd.) with an eluent of benzene-ethyl acetate (1:2) to perform separation and purification. The title compound (1.855 g) is obtained as colorless crystal.

NMR (CDCl$_3$) δ: 4.82 (1H,s), 6.68 (1H,s), 6.82 (2H,s), 6.86 (1H,s), 7.1–7.5 (20H,m), 9.33 (1H,s).

SYNTHESIS EXAMPLE 15

6-formyl-1-methoxy-3-(p-methoxybenzyl)oxy-4-pyridone

Starting from 2.913 g of 6-formyl-1-methoxy-3-(methoxybenzyl)oxy-4-pyridone and 15 g of active manganese dioxide, the title compound is obtained in the same manner as in Synthesis Example 2 as colorless crystal in a yield of 2.087 g.

NMR (CDCl$_3$) δ: 3.75 (3H,s), 3.97 (3H,s), 5.10 (2H,s), 6.78 (1H,s), 6.75–6.85 (2H,m), 7.23 (1H,s), 7.2–7.3 (2H,m), 9.83 (1H,s).

SYNTHESIS EXAMPLE 16

3-diphenylmethoxy-6-hydroxymethyl-1-isopropyl-4-pyridone

To a solution of 3.083 g of 3-diphenylmethoxy-6-hydroxymethyl-4-pyridone in 120 ml of methanol is added 11.082 g of isopropylamine at room temperature, and the mixture is stirred for 6 days. The reaction mixture is condensed to dryness under reduced pressure, and the resulting residue is subjected to flash column chromatography on 120 g of Wako-Gel C-300 (manufactured by Wako Pure Chemical Industries, Ltd.) with an eluent of chloroform-methanol (20:1) to perform separation and purification. The title compound (1.608 g) is obtained as colorless crystal.

NMR (CDCl$_3$) δ: 1.13 (6H,d,J=7Hz), 4.36 (2H,s), 4.68 (1H,hept,J=7Hz), 6.14 (1H,s), 6.46 (1H,s), 6.90 (1H,s), 7.1–7.5 (10H,m).

SYNTHESIS EXAMPLE 17

3-diphenylmethoxy-6-formyl-1-isopropyl-4-pyridone

To a methanol solution (120 ml) of 1.600 g of 3-diphenylmethoxy-6-hydroxymethyl-1-isopropyl-4-pyridone is added 10.00 g of active manganese dioxide at room temperature, and the mixture is stirred for 5 hours, then at 50° C. for 1 hour. After insolubles are removed by filtration, the filtrate is condensed under reduced pressure and the residue is subjected to flash column chromatography on 100 g of Wako-Gel C-300 (manufactured by Wako Pure Chemical Industries, Ltd.) with an eluent of benzene-ethyl acetate (1:2) to perform separation and purification. The title compound (0.862 g) is obtained as colorless foam.

NMR (CDCl$_3$) δ: 1.16 (6H,d,J=7Hz), 5.49 (1H,hept,J=7Hz), 6.66 (1H,s), 6.87 (1H,s), 7.12 (1H,s) 7.1–7.5 (10H,m), 49 (1H,s).

SYNTHESIS EXAMPLE 18

3-diphenylmethoxy-1-(2-furyl)methyl-6-hydroxymethyl-4pyridone

To a solution of 3.083 g of 3-diphenylmethoxy-6-hydroxymethyl-4-pyrone in 50 ml of methanol is added 7.645 g of 2-furfurylamine at room temperature, and the mixture is stirred for 4 days. The reaction mixture is condensed under reduced pressure, and the resulting residue is dissolved in 600 ml of chloroform. The organic solution is washed with water, a saturated aqueous potassium hydrogen sulfate solution in this sequence, dried over anhydrous magnesium sulfate and condensed under reduced pressure. The resulting crystal is collected by filtration, washed with a small amount of chloroform and dried under reduced pressure to give the title compound (2.72 g).

NMR ((CD$_3$)$_2$SO) δ: 4.54 (2H,s), 5.23 (2H,s), 6.25–6.4 (2H,m), 6.63 (1H,s), 6.75 (1H,s), 7.1–7.55 (11H,m), 7.95 (1H,s).

SYNTHESIS EXAMPLE 19

3-diphenylmethoxy-6-formyl-1-(2-furyl)methyl-4-pyridone

To a solution of 2.700 g of 3-diphenylmethoxy-1-(2-furyl)methyl-6-hydroxymethyl-4-pyridone in 200 ml of methanol is added 15.00 g of active manganese dioxide at room temperature, and the mixture is stirred for 4 hours. After insolubles are removed by filtration, the filtrate is subjected to flash column chromatography on 120 g of Wako-Gel C-300 (manufactured by Wako Pure Chemical Industries, Ltd.) with an eluent of chloroform-methanol (20:1) to perform separation and purification. The title compound (2.163 g) is obtained as colorless foam.

NMR (CDCl$_3$) δ: 5.30 (2H,s), 6.1–6.3 (2H,m), 6.68 (1H,s), 6.87 (1H,s), 7.10 (1H,s), 7.1–7.5 (10H,m), 0.48 (1H,s).

SYNTHESIS EXAMPLE 20

3-diphenylmethyl-6-hydroxymethyl-1-(4-pyridyl)methyl-4-pyridone

To a suspension of 3.083 g of 3-diphenylmethoxy-6-hydroxymethyl-4-pyrone in 20 ml of methanol is added 10.814 g of 4-aminopyridine at room temperature, and the mixture is stirred for 5 days. The reaction mixture is condensed under reduced pressure, and the resulting residue is dissolved in 100 ml of dichloromethane. The organic solution is washed with water (100 ml×3), dried over anhydrous magnesium sulfate and condensed to dryness under reduced pressure. A 50 ml portion of ethyl acetate is added to the residue to crystallize it. After left standing at 4° C. for 6 hours, the resulting crystal is collected by filtration, washed with a small amount of ethyl acetate and dried under reduced pressure to give the title compound (2.401 g).

NMR (CD$_3$)$_2$SO) δ: 4.12 (2H,d,J=6Hz), 5.09 (2H,s), 5.51 (1H,t,J=6Hz), 6.24 (1H,s), 6.6–6.7 (3H,m), 7.1–7.5 (10H,m), 7.51 (1H,s), 8.3–8.4 (2H,m).

SYNTHESIS EXAMPLE 21

3-diphenylmethyl-6-formyl-1-(4-pyridyl)methyl-4-pyridone

To a solution of 2.391 g of 3-diphenylmethyl-6-hydroxymethyl-1-(4-pyridyl)methyl-4-pyridone in 150 ml of methanol is added 14.0 g of active manganese dioxide at room temperature, and the mixture is stirred for 30 minutes. After insolubles are removed by filtration, the filtrate is subjected to flash column chromatography on 100 g of Wako-Gel C-300 (manufactured by Wako Pure Chemical Industries, Ltd.) with an eluent of chloroform-methanol (20:1) to perform separation and purification. The title compound (2.043 g) is obtained as colorless foam.

NMR (CDCl$_3$) δ: 5.32 (2H,s), 6.55–6.65 (2H,m), 6.76 (1H,s), 6.96 (1H,s), 7.00 (1H,s), 7.1–7.5 (10H,m), 8.4–8.5 (2H,m), 9.45 (1H,s).

SYNTHESIS EXAMPLE 22

2-formyl-1,5-di-p-methoxybenzyloxy-4-pyridone

In 50 ml of acetonitrile is dissolved 2 g of 1,5-di-p-methoxybenzyl-2-hydroxymethyl-4-pyridone, and 10 g of active manganese dioxide is added to the solution. The reaction is continued at 50° C. for 3.5 hours. After reaction has completed, the manganese dioxide is removed by filtration, and acetonitrile washing is conducted. The filtrate is condensed under reduced pressure. The residue is dissolved in 100 ml of dichloromethane, washed with water, dried over anhydrous magnesium sulfate, and condensed under reduced pressure. The residue is subjected to silica gel column chromatography with an eluent of chloroform-methanol (50:1) to perform purification. The title compound (1.15 g) is obtained.

NMR (CDCl$_3$) δ: 3.81 (3H,s), 3.82 (3H,s), 5.00 (2H,s), 5.08 (2H,s), 6.72 (1H,s), 6.84 (1H,d), 6.89 (1H,d), 7.05 (2H,d), 7.10 (1H,s), 7.31 (2H,d), 9.60 (1H,s).

SYNTHESIS EXAMPLE 23

2-formyl-1-diphenylmethyloxy-5-p-methoxybenzyloxy-4-pyridone

In 300 ml of anhydrous methanol is suspended 6 g of 2-hydroxymethyl-5-p-methoxybenzyloxy-4-pyridone, and 15 g of active manganese dioxide is added thereto. The reaction is performed under heating at a refluxing temperature for 30 minutes. At the end of the reaction, the manganese dioxide is removed by filtration, and the filtrate is condensed under reduced pressure. The residue is dissolved in 150 ml of ethyl acetate, washed with water, dried over anhydrous magnesium sulfate, and condensed under reduced pressure to give the title compound (5.63 g).

NMR (CDCl$_3$) δ: 3.80 (3H,s), 4.91 (2H,s), 5.96 (1H,s), 6.71 (1H,s), 6.89 (2H,d), 6.96 (1H,s), 7.23 (2H,d), 7.2–7.5 (10H,m), 9.65 (1H,s).

SYNTHESIS EXAMPLE 24

2-formyl--4-diphenylmethyloxy-5-p-methoxybenzyloxypyridine-N-oxide

In 200 ml of acetonitrile is suspended 6 g of 2-hydroxymethyl-5-p-methoxybenzyloxy-N-oxide, and the suspension is dissolved at 50° C. To the solution is added 17 g of active manganese dioxide, and the reaction is performed under the same temperature for 1.5 hours. At the end of the reaction, the manganese dioxide is removed by filtration, and the filtrate is condensed. The residue is dissolved in 150 ml of ethyl acetate, washed with water, dried over anhydrous magnesium sulfate, and condensed under reduced pressure. The residue is dissolved in 30 ml of dichloromethane, and 50 ml of ether is added. The resulting crystal is collected by filtration to give the title compound (2.54 g).

NMR (CDCl$_3$) δ: 3.83 (3H,s), 5.14 (2H,s), 6.31 (1H,s), 6.93 (2H,d), 7.22 (1H,s), 7.2–7.5 (12H,m), 7.87 (1H,s), 10.41 (1H,s).

SYNTHESIS EXAMPLE 25

Sodium 3-(3-diphenylmethoxy-6-hydroxymethyl-4-pyridon-1-yl)propionate

To a suspension of 3.083 g of 3-diphenylmethoxy-6-hydroxymethyl-4-pyrone in 100 ml of methanol is added 30 ml of aqueous sodium β-alanine prepared from 8.910 g of δ-alanine and 4.00 g of sodium hydroxide and the mixture is stired at room temperature for 3 days. The reaction mixture is condensed to a volume of 30 ml under reduced pressure, and the resulting crystal is collected by filtration and washed with a small amount of cold water. The crystal thus obtained is dried under reduced pressure to give the title compound (2.260 g).

NMR (CDCl$_3$) δ: 2.17 (2H,t,J=7Hz), 3.0–3.6 (1H,broad), 3.88 (2H,t,J=7Hz), 4.31 (2H,s), 6.14 (1H,s), 6.66 (1H,s), 7.1–7.6 (11H,m).

SYNTHESIS EXAMPLE 26

Diphenylmethyl 3-(3-diphenylmethoxy-6-formyl-4-pyridon-1-yl)propionate

To a solution of 1.560 g of sodium 2-(3-diphenylmethoxy-6-hydroxymethyl-4-pyridon-1-yl) propionate in 250 ml of methanol is added 9.0 g of active manganese dioxide, and the mixture is stirred for 2 hours. After insolubles are removed by filtration, the filtrate is condensed to a volume of 40 ml under reduced pressure, and insolubles are again removed by filtration. The filtrate is condensed to dryness. The residue is suspended in dichloromethane (150 ml)-water (30 ml), 0.831 g of diphenyldiazomethane is added thereto, and the mixture is adjusted to pH 3 by dropwise addition of saturated aqueous potassium hydrogen sulfate solution with stirring. The reaction mixture is further stirred at room temperature for 2 hours, the organic layer is separated, dried over anydrous magnesium sulfate, and condensed to dryness under reduced pressure. The residue is subjected to flash column chromatography on 80 g of Wasko-Gel C-300 (manufactured by Wako Pure Chemical Industries Ltd.) with an eluent of benzene-ethyl acetate (1:2) to perform sepration and purification. The title compound (1.442 g) is obtained.

NMR (CDCl$_3$) δ: 3.73 (2H,t,J=7Hz), 3.36 (2H,t,J=7Hz), 6.59 (1H,s), 6.77 (1H,s), 6.84 (1H,s), 7.10 (1H,s), 7.1–7.5 (20H,m), 9.43 (1H,s).

SYNTHESIS EXAMPLE 27

Sodium 4-(3-diphenylmethoxy-6-hydroxymethyl-4-pyridon-1-yl)butanoate

Starting from 3.083 g of 3-diphenylmethoxy-6-hydroxymethyl-4-pyrone and 10.312 g of 4-aminobutane, the title compound (2.130 g) is obtained as colorless crystal in the same manner as in Synthesis Example 25.

NMR ((CD$_3$)$_2$SO) δ: 1.4–2.0 (4H,m), 3.6–3.9 (3H,m), 4.3 (2H,s), 6.14 (1H,s), 6.68 (1H,s), 7.1–7.5 (11H,m).

SYNTHESIS EXAMPLE 28

Diphenylmethyl 4-(3-diphenylmethoxy-6-formyl-4-pyridon-1-yl)butanoate

Starting from 2.100 g of sodium 4-3-diphenylmethoxy-6-hydroxymethyl-4-pyridon-1-butanoate, the title compound (2.319 g) is obtained in the same manner as in Synthesis Example 26.

NMR CDCl$_3$) δ: 1.38 (2H,quint,J=7 Hz), 2.24 (2H,t,J=7 Hz), 4.13 (2H,t,J=7 Hz), 6.74 (1H,s), 6.86 (2H,s), 6.94 (1H,s), 7.1–7.5 (20H,m), 9.43 (1H,s).

SYNTHESIS EXAMPLE 29

Diphenylmethyl 6-(3-diphenylmethoxy-6-hydroxymethyl-4pyridon-1-yl)hexanoate

To a suspension of 3.083 g of 3-diphenylmethoxy-6-hydroxmethyl-4-pyrone in 100 ml of methanol is added at room temperature 30 ml of an aqueous sodium 6-aminohexanoate prepared from 13.118 g of 6-aminohexanoic acid and 4.00 g of sodium hydroxide, and the mixture is stirred for 3 days. After the reaction mixture is condensed to a volume of 30 ml under reduced pressure, a 50 ml portion of water is added, and the mixture is again condensed. A 100 mg portion of dichloromethane and 2.914 g of diphenyldiazomethane are added in this sequence, and the mixture is adjusted to pH 3 by dropwise addition of a saturated aqueous potassium hydrogen sulfate solution. The reaction mixture is further stirred at room temperature for 2 hours, and the organic layer is separated, dried over anhydrous magnesium sulfate, and condensed to dryness under reduced pressure. The residue is subjected to flash column chromatography on 80 g of Wako-Gel C-300 (manufactured by Wako Pure Chemical Industries, Ltd.) with an eluent of chloroform-methanol (20:1) to perform separation and purification. The title compound (4.316 g) is obtained.

NMR CDCl$_3$) δ: 0.9–1.9 (6H,m), 2.31 (2H,t,J=7 Hz), 3.70 (2H,t,J=7 Hz), 2.29 (2H,s), 5.4–5.9 (1H,broad), 6.21 (1H,s), 6.50 (1H,s), 6.78 (1H,s), 6.86 (1H,s), 7.1–7.5 (10H,m).

SYNTHESIS EXAMPLE 30

Diphenylmethyl 6-(3-diphenylmethoxy-6-formyl-4-pyridon-1-yl)hexanoate

To a solution of 3.510 g of diphenylmethyl 6-(3-diphenylmethoxy-6-hydroxymethyl-4-pyridon-1-yl)hexanoate in 210 ml of dichloromethane is added 21.9 g of active manganese dioxide, and the mixture is stirred at room temperature for 20 minutes. After insolubles are removed by filtration, the filtrate is condensed under reduced pressure to give crystal. It is washed with a mixed solvent of isopropyl ether-ethyl acetate (5:1), and condensed under reduced pressure to give the title compound (2.103 g).

NMR CDCl$_3$) δ: 0.95–1.8 (6H,m), 2.36 (2H,t,J=7 Hz), 4.03 (2H,t,J=7 Hz), 6.74 (1H,s), 6.85 (1H,s), 6.88 (2H,s), 7.1–7.6 (20H,m), 9.45 (1H,s).

SYNTHESIS EXAMPLE 31

Sodium DL-2-(3-diphenylmethoxy-6-hydroxymethyl-4-pyridon-1-yl)propionate

To a suspension of 3.083 g of 3-diphenylmethoxy-6-hydroxymethyl-4-pyrone in 100 ml of methanol is added 50 ml of aqueous sodium DL-alanine prepared from 17.82 g of DL-alanine and 8.00 g of sodium hydroxide. The reaction mixture is stirred at room temperature for 9 days and condensed to a volume of 60 ml, and the condensed mixture is treated on 200 ml of DIAION HP-20 resin (Mitsubishi Chemical Industries Ltd.) with an eluent of water and 40% methanol-water in sequence to perform separation and purification. The fractions containing the objective product are condensed under reduced pressure, and then lyophilized. The title compound (2.674 g) is thus obtained.

NMR ((CD$_3$)$_2$SO) δ: 1.17 (3H,d,J=7 Hz), 4.27 (2H,s), 4.49 (1H,q,J=7 Hz), 5.7–6.2 (1H,broad), 6.15 (1H,s), 6.55 (1H,s), 7.1–7.5 (11H,m).

SYNTHESIS EXAMPLE 32

Diphenylmethyl DL-2-(3-diphenylmethoxy-6-formyl-4-pyridon-1-yl)propionate

Starting from 2.660 g of sodium DL-2-(3-diphenylmethoxy-6-hydroxymethyl-4-pyridon-1-yl)propionate, the title compound (2.384 g) is obtained in the same manner as in Synthesis Example 26.

NMR CDCl$_3$) δ: 1.42 (2H,d,J=7 Hz), 6.03 (2H,q,J=7 Hz), 6.40 (1H,s), 6.76 (1H,s), 6.86 (1H,s), 6.93 (1H,s), 7.0–7.5 (20H,m), 9.36 (1H,s).

SYNTHESIS EXAMPLE 33

Sodium (2S)-2-phenyl-2-(3-diphenylmethoxy-6-hydroxymethyl-4-pyridon-1-yl)acetate To 30 ml of an aqueous solution of 4.00 g of sodium hydroxide are added 15.12 g of phenylglycine and 170 ml of methanol in this sequence. To this solution is added 3.083 g of 3-diphenylmethoxy-6-hydroxymethyl-4-pyrone, and the mixture is stirred at room temperature for 18 days. After the reaction mixture is condensed under reduced pressure, to the residue are 150 ml of water and 200 ml of ether and the mixture is thoroughly stirred to form a dual phase solution. After the aqueous layer is separated and condensed to a volume of 60 ml, it is treated on 200 ml of DIAION HP-20 resin (Mitsubishi Chemical Industries Ltd.) with an eluent of water and 40% methanol-water in sequence to perform separation and purification. The fractions containing the objective product are condensed under reduced pressure, and then lyophilized. The title compound (2.842 g) is thus obtained.

NMR (D$_2$O) δ: 4.69 (2H,s), 5.94 (1H,s), 6.12 (1H,s), 6.8–7.4 (16H,m).

SYNTHESIS EXAMPLE 34

Diphenylmethyl (2S)-2-phenyl-2-(3-diphenylmethoxy-6-formyl-4-pyridon-1-yl)acetate Starting from 2.710 g of sodium (2S)-2-phenyl-2-(3-diphenylmethoxy-6-hydroxymethyl-4-pyridon-1-yl)acetate, the title compound (2.384 g) is obtained in the same manner as in Synthesis Example 26.

NMR (CDCl$_3$) δ: 6.23 (1H,s), 6.75–6.85 (2H,m), 6.89 (1H,s), 6.92 (1H,s), 7.0–7.5 (25H,m), 9.46 (1H,m).

SYNTHESIS EXAMPLE 35

Sodium 2-(3-diphenylmethoxy-6-formyl-4-pyridon-1-yl)acetate

To a methanol solution (300 ml) of sodium 2-(3-diphenylmethoxy-6-hydroxymethyl-4-pyridon-1-yl)acetate (3.024 g) is added 18.0 g of active manganese dioxide, and the mixture is stirred at room temperature for 4 hours. The reaction mixture is filtered, and the filtrate is condensed to dryness under reduced pressure. The residue is treated with 200 ml of DIAION HP-20 resin (Mitsubishi Chemical Industries Ltd.) with an eluent of water, 30% methanol-water and 50% methanol-water in sequence to perform separation and purification. The fractions containing the objective product are condensed to dryness under reduced pressure. The title compound (2.322 g) is thus obtained.

NMR ((CD$_3$)$_2$SO) δ: 4.49 (2H,s), 6.60 (1H,s), 6.79 (1H,s), 7.1–7.5 (10H,m), 7.59 (1H,s), 9.55 (1H,s).

SYNTHESIS EXAMPLE 36

N,N-dimethyl-2-(3-diphenylmethoxy-6-formyl-4-pyridon-1-yl)acetamide

To a dimethylformamide solution (20 ml) of 0.771 g of sodium 2-(3-diphenylmethoxy-6-formyl-4-pyridon-1yl)acetate are added under ice-cooling 0.231 g of pyridinium chloride, 0.242 g of N-hydroxysuccinimide and 0.433 g of N,N'-dicyclohexylcarbodiimide in sequence, and the mixture is stirred for 1 hour. To the reaction mixture under ice-cooling is added 1 ml of 10% dimethylformamide solution of dimethylamine which is prepared under ice-cooling, and stirring is continued at the same temperature for 2 hours. The reaction mixture is filtered, and the filtrate is poured into 100 ml of ice-water and extracted with 50 ml of dichloromethane. The organic layer is washed twice with water, dried over anhydrous magnesium sulfate and condensed under reduced pressure. The residue is subjected to flash column chromatography on 50 g of Wako-Gel C-300 (manufactured by Wako Pure Chemical Industries, Ltd.) with an eluent of chloroform-methanol (20:1) to perform separation and purification. The title compound (0.283 g) is thus obtained.

NMR CDCl$_3$) δ: 2.91 (3H,s), 2.98 (3H,s), 4.84 (2H,s), 6.70 (1H,s), 6.84 (1H,s), 6.89 (1H,s), 7.1–7.5 (10H,m), 9.41 (1H,s).

SYNTHESIS EXAMPLE 37

Sodium 2-(3-diphenylmethoxy-6-hydroxymethyl-4-pyridon-1yl)ethanesulfonate

To a suspension of 3.083 g of 3-diphenylmethoxy-6-hydroxymethyl-4-pyrone in 100 ml of methanol is added 30 ml of aqueous solution of sodium taurine which is prepared from 12.51 g of taurine (2-aminoethanesulfonic acid) and 4.00 g of sodium hydroxide, and the mixture is stirred for 3 days. The reaction mixture is condensed to a volume of 40 ml and treated with 200 ml of DIAION HP-20 resin (Mitsubishi Chemical Industries Ltd.) with an eluent of water and 40% methanol-water in sequence to perform separation and purification. The fractions containing the objective product are condensed under reduced pressure and lyophilized. The title compound (3.250 g) is thus obtained.

NMR (D$_2$O) δ: 3.10 (2H,t,J=7 Hz), 4.34 (2H,t,J=7 Hz), 4.68 (2H,s), 6.47 (1H,s), 6.72 (1H,s), 7.4–7.8 (11H,m).

SYNTHESIS EXAMPLE 38

Sodium 2-(3-diphenylmethoxy-6-formyl-4-pyridon-1yl)ethanesulfonate

To a methanol solution (300 ml) of sodium 2-(3-diphenylmethoxy-6-hydroxymethyl-4-pyridon-1yl)ethanesulfonate (3.200 g) is added 19.2 g of active manganese dioxide, and the mixture is stirred at room temperature for 2 hours. The reaction mixture is filtered, and the filtrate is condensed to dryness under reduced pressure. The residue is treated with 200 ml of DIAION HP-20 resin (Mitsubishi Chemical Industries Ltd.) with an eluent of water, 30% methanol-water and 40% methanol-water in sequence to perform separation and purification. The fractions containing the objective product are condensed under reduced pressure and then lyophilized. The title compound (2.322 g) is thus obtained.

NMR ((CD$_3$)$_2$SO) δ: 2.73 (2H,t,J=7 Hz), 4.41 (2H,t,J=7 Hz), 6.72 (1H,s), 6.77 (1H,s), 7.1–7.5 (10H,m), 7.67 (1H,s), 9.73 (1H,s).

SYNTHESIS EXAMPLE 39

1-[3,4-bis(p-methoxybenzyloxy)benzyl]-3-diphenylmethoxy-6-hydroxymethyl-4-pyridone To 10 ml of a dimethylformamide solution in 3-diphenylmethoxy-6-hydroxymethyl-4-pyrone (0.480 g) are added 0.621 g of 3,4-bis(p-methoxybenzyloxy)benzyl chloride and 0.215 g of potassium carbonate, and the mixture is stirred at room temperature for 14 hours. The reaction mixture is poured into 50 ml of ice-water and extracted with 50 ml of dichloroethane. The organic layer is washed with water (30ml ×2), dried over anhydrous magnesium sulfate and subjected to flash column chromatography on 50 g of Wako-Gel C-300 (manufactured by Wako Pure Chemical Industries, Ltd.) with an eluent of chloroform-methanol (20:1) to perform separation and purification. The title compound (0.473 g) is thus obtained.

NMR CDCl$_3$) δ: 1.5–1.8 (1H,broad), 3.75 (3H,s), 3.78 (3H,s), 4.19 (2H,broad s), 4.86 (4H,broad s), 5.03 (2H,s), 6.13 (1H,dd,J=8 Hz,2 Hz), 6.24 (1H,s), 6.39 (1H,d,J=2 Hz), 6.54 (1H,s), 6.72 (1H,d,J=8 Hz), 6.7–7.0 (6H,m), 7.1–7.5 (14H,m).

In this process, 0.432 g of 4-O-alkyl product is obtained as a by-product.

SYNTHESES EXAMPLE 40

1-[3,4-bis(p-methoxybenzyloxy)benzyl]-3-diphenylmethoxy6-formyl-4-pyridone

To a dichloromethane solution (210 ml) of 1-[3,4-bis(p-methoxybenzyloxy)benzyl]-3-diphenylmethoxy-6-hydroxymethyl-4-pyridone (0.462 g) is added active manganese dioxide (2.40 g), and the mixture is stirred at room temperature for 20 minutes. Insolubles are removed by filtration, the filtrate is subjected to flash column chromatography on 50 g of Wako-Gel C-300 (manufactured by Wako Pure Chemical Industries, Ltd.) with an eluent of chloroform-methanol (20:1) to perform separation and purification. The title compound (0.264 g) is thus obtained as colorless crystal.

NMR CDCl$_3$) δ: 3.78 (6H,s), 4.91 (2H,s), 5.03 (2H,s), 5.18 (2H,s), 6.27 (1H,dd,J=8Hz), 2Hz), 5.69 (1H,s), 6.7–7.0 (8H,m), 7.1–7.5 (14H,m), 9.40 (1H,s).

EXAMPLE 1

(6 R ,7R) -7 - [( Z) - 2- (2 -aminothiazol 4-yl)-2-methoxyiminoacetamido]-3-[2(1,5-dihydroxy-4-pyridon-2-yl)vinyl]-ceph-3-em-4-carboxylic acid, cis-isomer (a) In 20 ml of acetone is dissolved 1.59 g of p-methoxybenzyl (6R,7R)-7-[(Z)-2-(2-tritylaminothiazol-4-yl)-2-methoxyiminoacetamido]-3-chloromethyl-ceph-3-em-4-carboxylate. To this solution are added 580 mg of triphenylphosphine and 330 mg of sodium iodide, and the reaction is conducted at room temperature for 1 hour. After the reaction is completed, the reaction mixture is condensed to dryness under reduced pressure. The residue is dissolved in 10 ml of dichloromethane, and 1.06 g of 2-formyl-1,5-di-p-methoxybenzyloxy-4-pyridone is added to the solution. Then, 10 ml of an aqueous solution containing 500 mg of sodium hydrogen carbonate is added, and the reaction is performed for 4 hours. To the reaction mixture is added 50 ml of dichloromethane. The aqueous layer is separated, and the organic layer is washed with water, dried over anhydrous magnesium sulfate and condensed to dryness. The residue is purified by silica gel column chromatography (chloroform-methanol (100:1)) to give 1.43 g of p-methoxybenzyl (6R,7R)-7-[(Z)-2-(2-tritylaminothiazol-4-yl)-2-methoxyiminoacetamido]-3-[2-(1,5-dihydroxy-4-pyridon-2-yl)vinyl]-ceph- 3-em-4-carboxylate, cis-isomer and 320 mg of the trans-isomer.

mnr (CDCl$_3$) δ: cis-isomer:2.90 (1H,d), 3.26 (1H,d), 3.87 (3H,s), 3.88 (6H,s), 4.07 (3H,s), 4.84 (2H,s), 4.99 (1H,d), 5.03 (2H,ABq), 5.17 (2H,s), 5.96 (1H,q), 6.20 (1H,s), 6.24 (1H,d), 6.71 (1H,s), 6.78 (1H,d), 6.87 (6H,m), 6.98 (1H,s), 7.00 (1H,s), 7.06 (2H,s), 7.20–7.40 (20H,m);

trans-isomer: 3.45 (2H,ABq), 3.73 (3H,s), 3.79 (3H,s), 3.80 (3H,s), 4.86 (2H,ABq), 5.00 (1H,d), 5.03 (2H,ABq), 5.90 (1H,q), 6.37 (1H,d), 6.48 (1H,s), 6.7–6.95 (8H,m), 6.98 (1H,s), 7.00 (1H,s), 7.02 (2H,d), 7.20–7.40 (20H,m).

(b) In 2.17 g of anisole is dissolved 1.14 g of the cis-isomer, and 616 ml of trifluoroacetic acid is added to the solution dropwisely. After the reaction is conducted at the same temperature for 1 hour, the mixture is dropwisely added to 50 ml of isopropyl ether, and the resulting precipitate is collected by filtration. The precipitate is suspended in 10 ml of water, and a saturated aqueous sodium hydrogen carbonate solution is added to adjust pH 7.5 and to dissolve the precipitate therein and purified by HP-20 column chromatography (eluted with water) to give 315 mg of the title compound as a sodium salt. NMR (D$_2$O) δ: 3.16 (1H,d), 3.53 (1H,d), 4.00 (3H,s), 5.31 (1H,d), 5.85 (1H,d), 6.53 (1H,d), 6.61 (1H,s), 6.74 (1H,d), 7.05 (1H,s), 7.61 (1H,s).

EXAMPLE 2

(6R, 7R)-7-[(Z)- 2- ( 2-aminothiazol-4-yl)-2-methoxyiminoacetamido]-3-[2-(1,5-dihydroxy-4-pyridon-2-yl)vinyl]-ceph-3-em-4-carboxylic A 285 mg portion of the trans-isomer obtained in Example 1 (a) is dissolved in 0.54 ml of anisole, 1.54 ml of trifluoroacetic acid is added to the solution under ice-cooling, and the reaction is carried out for 1 hour. To the reaction mixture is added 10 ml of isopropyl ether, and the resulting precipitate is collected by filtration and purified by HP-20 column chromatography (eluent: H$_2$O) to give 95 mg of the title compound as a sodium salt.

NMR (D$_2$O) δ: 3.86 (2H,ABq), 4.04 (3H,s), 5.35 (1H,d), 5.89 (1H,d), 6.94 (1H,s), 7.08 (1H,d), 7.08 (1H,s), 7.28 (1H,d), 7.57 (1H,s).

EXAMPLE 3

(6R ,7R )-7-[(Z)-2 -(2-aminothiazol-4-yl)-2-carboxymethoxyiminoacetamido]-3-[2-(1,5-dihydroxy-4-pyridon-2-yl)vinyl]-ceph-3-em-4-carboxylic acid, cis-isomer (a) In 12 ml of acetone is dissolved 1 g of p-methoxybenzyl (6R,7R)-7-[(Z)-2-(2-tritylaminothiazol-4-yl)-2-butoxycarbonyloxymethoxyiminoacetamido]-3-chloromethyl-ceph-3-em-4-carboxylate, and 350 mg of triphenylphosphine and 200 mg of sodium iodide are added to the solution. After reaction at room temperature for 1 hour, the reaction mixture is condensed to dryness. The residue is dissolved in 6 ml of dichloromethane, and 790 mg of 2-formyl-1-diphenylmethyloxy-5-di-p-methoxybenzyloxy-4-pyridone is added to the solution. To this mixture is added 6 ml of an aqueous solution containing 300 mg of sodium hydrogen carbonate, and the reaction is conducted at room temperature for 4 hours. After the reaction is completed, 30 ml of dichloromethane is added, the organic layer, after separating the aqueous layer, is washed with water, dried over anhydrous magnesium sulfate and condensed to dryness. The residue is purified by silica gel column chromatography [eluent: chloroformethyl acetate (1:1)]to give 500 mg of p-methoxybenzyl (6R,7R)-7-[(Z) -2-(2-tritylaminothiazol-4-yl)-2-t-butoxycarbonyloxymethoxyiminoacetamido]-3-[2-(1-diphenylmethyloxy-5-p-methoxybenzyloxy-4-pyridon-2-yl)vinyl]-ceph-3-em-4-carboxylate, cis-isomer.

NMR (CDCl$_3$) δ: 1.42 (9H,s), 2.90 (1H,d), 3.30 (1H,d), 3.79 (6H,s), 4.73 (2H,s), 4.78 (2H,ABq), 5.06 (1H,d), 5.12 (2H,ABq), 5.86 (1H,s), 5.88 (1H,q), 6.17 (1H,s), 6.19 (1H,d), 6.75–6.90 (7H,m), 7.00 (1H,s), 7.15–7.45 (29H,m), 8.87 (1H,d).

(b) A 500 mg portion of the cis-isomer obtained in (a) is dissolved in 0.85 ml of anisole, 2.4 ml of trifluoroacetic acid is added thereto under ice-cooling, and the reaction is conducted at the same temperature for 3 hours. To the reaction mixture is added 15 ml of isopropyl ether, and the resulting precipitate is collected by filtration and purified by HP-20 column chromatography to give 100 mg of the title compound as a sodium salt.

NMR (D$_2$O) δ: 3.15 (1H,d), 3.50 (1H,d), 4.55 (2H,s), 5.29 (1H,d), 5.83 (1H,d), 6.49 (1H,d), 6.52 (1H,s), 6.69 (1H,d), 7.03 (1H,s), 7.51 (1H,s).

EXAMPLE 4

(6R,7R)-7-[(Z)-2-(2-aminothiazol-4-yl)-2-(1-methyl-1carboxy)ethoxyiminoacetamido]-3-[2-(1,5-dihydroxy-4-pyridon-2-yl)vinyl]-ceph-3-em-4-carboxylic acid, cis-isomer (a) In 10 ml of acetone is dissolved 920 mg of p-methoxybenzyl (6R,7R)-7-[(Z)-2-(2-tritylaminothiazol-4-yl)-2-(1-methyl-1-t-butoxycarbonyl)ethoxyiminoacetamido]3-chloromethyl-ceph-3-em-4-carboxylate. To this solution are added 290 mg of triphenylphosphine and 165 mg of sodium iodide, and the reaction is conducted at room temperature for 1 hour. The reaction mixture is condensed to dryness. To the residue is added 10 ml of dichloromethane, and 2.2 g of 2-formyl-4-diphenyl-methyloxy-5-p-methoxybenzyloxy-4-pyridine-N-oxide and 10 ml of an aqueous solution containing 250 mg of sodium hydrogen carbonate are further added, and the reaction is performed at room temperature for 2 hours.

To the reaction mixture are added 50 ml of dichloromethane and 20 ml of water. The aqueous layer is separated, and the organic layer is washed with water, dried over anhydrous magnesium sulfate and condensed to dryness. The residue is dissolved in 10 ml of dichloromethane, 15 ml of ether is added to the solution, the resulting crystal is removed by filtration, and the filtrate thus obtained is condensed to dryness. The residue is purified by silica gel column chromatography [chloroform-methanol (1:1)]and LH-20 column chromatography [chloroform-methanol (1:1)]to give 530 mg of p-methoxybenzyl (6R,7R)-7-[(Z)-2-(2-tritylaminothiazol-4yl)-2-(1-methyl-1-t-butoxycarbonyl)ethoxyiminoacetamido]-3-[2-(4-diphenylmethyloxy-5-p-methoxybenzyloxypyridine-N-oxide-2-yl)vinyl]-ceph-3-em-4-carboxylate, cis-isomer.

NMR CDCl$_3$) δ: 1.03 (9H,s), 1.51 (3H,d), 1.63 3.25 (2H,ABq), 3.79 (3H,s), 3.82 (3H,s), 4.99 (1H,d), 5.07 (2H,s), 5.20 (2H,ABq), 5.87 (1H,q), 6.17 (1H,s), 6.58 (1H,d), 6.60 (1H,s), 6.78 (1H,s), 6.80 (1H,d), 6.86 (1H,d), 6.88 (1H,s), 6.91 (2H,d), 7.1–7.5 (29H,m), 7.93 (1H,s), 8.68 (1H,d).

(b) In 0.76 ml of anisole is dissolved 460 mg of the cis-isomer obtained in (a), and 2.7 ml of trifluoroacetic acid is added to the solution dropwisely under ice-cooling. The reaction is conducted at the same temperature for 4 hours. To the reaction mixture is dropwisely added 12 ml of isopropyl ether, and the resulting precipitate is collected by filtration. The precipitate is purified by HP-20 column chromatography to give 105 mg of the title compound as a sodium salt.

NMR ($D_2O$) δ: 1.49 (3H,s), 1.51 (3H,s), 3.16 (1H,d), 3.52 (1H,d), 5.32 (1H,d), 5.86 (1H,d), 6.53 (1H,d), 6.64 (1H,s), 6.74 (1H,d), 7.03 (1H,s), 7.62 (1H,s).

EXAMPLE 5

(6R,7R)-7-[(Z)-2-(2-aminothiazol-4-yl)-2-(1-methyl-1carboxy)ethoxyiminoacetamido]-3-[2-(1,5-dihydroxy-4-pyridon-2-yl)vinyl]-ceph-3-em-4-carboxylic acid, trans-isomer (a) In 15 ml of acetone is dissolved 730 mg of p-methoxybenzyl (6R,7R)-7-phenylacetamido-3-chloromethylceph-3-em-4-carboxylate. To this solution are added 435 mg of triphenylphosphine and 250 mg of sodium iodide, and the reaction is conducted at room temperature for 1 hour. After the reaction has finished, the reaction mixture is condensed to remove acetone. The residue is dissolved in 15 ml of dichloromethane, and 2.66 g of 2-formyl-4-diphenylmethyloxy-5-p-methoxybenzyloxy-4-pyridine-N-oxide and 10 ml of an aqueous solution containing 250 mg of sodium hydrogen carbonate are further added, and the reaction is performed at room temperature for 2 hours.

After the reaction has finished, to the reaction mixture are added 50 ml of dichloromethane and 20 ml of water are added to the reaction mixture. The organic layer is washed with water, dried over anhydrous magnesium sulfate and condensed to dryness. To the residue is added 15 ml of dichloromethane and 22 ml of ether, and the resulting crystal is removed by filtration, and the filtrate thus obtained is condensed to dryness. The residue is purified by silica gel column chromatography [chloroform-methanol (100:1)]and LH-20 column chromatography [chloroform-methanol (1:1)]to give 935 mg of p-methoxybenzyl (6R,7R)-7-phenylacetamido-3-[2(4-diphenylmethyloxy-5-p-methoxybenzyloxypyridine-N-oxide-2-yl)vinyl]-ceph-3-em-4-carboxylate as a mixture of the cis- and trans-isomers.

(b) The product is dissolved in 15 ml of dichloromethane, and 0.39 ml of pyridine and 450 mg of phosphorus pentachloride are added to the solution at a temperature from −10° C. to −15° C. The reaction is conducted at the same temperature for 30 minutes and then further continued for 1.5 hours under ice-cooling.

The reaction mixture is added to 15 ml of anhydrous methanol at a temperature from −10° C. to −15° C., and the reaction is continued at room temperature for 1 hour. Then, the reaction mixture is added to the mixture of 50 ml of dichloromethane and 50 ml of saturated saline under ice-cooling, and the organic layer is washed with 25 ml of a saturated aqueous sodium hydrogen carbonate solution and 25 ml of saturated saline in sequence, dried over anhydrous magnesium sulfate and condensed to dryness. The residue is purified by silica gel column chromatography [chloroform-methanol (50:1)]to give 390 mg of the cis-isomer and 160 mg of the trans-isomer of p-methoxybenzyl (6R,7R)-7-[amino-3-[2-(4-diphenylmethyloxy5-p-methoxybenzyloxypyridine-N-oxide-2-yl)vinyl]-ceph-3-em-4-carboxylate.

NMR CDCl$_3$) δ:

trans-isomer:

3.63 (1H,d), 3.78 (1H,d), 3.77 (3H,s), 3.82 (3H,s), 4.75 (1H,bs), 4.96 (1H,d), 5.07 (2H,s), 5.31 (2H,ABq), 6.29 (1H,s), 6.91 (4H,m), 7.00 (1H,s), 7.2–7.5 (15H,m), 7.56 (1H,d), 7.90 (1H,s).

cis-isomer:

3.12 (1H,d), 3.36 (1H,d), 3.81 (3H,s), 3.83 (3H,s), 4.86 (1H,bs), 4.89 (1H,d), 5.08 (2H,s), 5.24 (2H,ABq), 6.26 (1H,s), 6.59 (1H,d), 6.74 (1H,s), 6.78 (1H,d), 6.87 (2H,d), 6.91 (2H,d), 7.15–7.5 (14H,m), 7.94 (1H,s).

(c) The trans-isomer obtained in (b) is dissolved in 5 ml of dichloromethane, and 115 mg of (Z)-2-(2-tritylaminothiazol-4-yl)-2-(1-methyl-1-t-butoxycarbonyl)ethoxyiminoacetic acid is added to the solution. At a temperature from −10° C. to −15° C., 80 μl of pyridine and 20.5 μl of phosphorus oxychloride are added to the solution, and the reaction is conducted for 30 minutes. After the reaction has finished, 25 ml of ethyl acetate is added to the reaction mixture, and the resulting mixture is washed with 15 ml of saturated saline, dried over anhydrous magnesium sulfate and condensed to dryness. The residue is purified by silica gel column chromatography [chloroform-ethyl acetate (1:1)]to give 166 mg of the trans-isomer of p-methoxybenzyl (6R,7R)-7[(Z)-2-(2-tritylaminothiazol-4-yl)-2-(1-methyl-1-t-butoxycarbonyl)ethoxyliminoacetamido]-3-[2-(4-diphenylmethyloxy-5-p-methoxybenzyloxypyridine-N-oxide-2yl) vinyl]-ceph-3-em-4-carboxylate.

NMR CDCl$_3$) δ: 1.40 (9H,s), 1.60 (3H,s), 1.63 (3H,s), 3.61 (1H,d), 3.78 (3H,s), 3.81 (1H,d), 3.82 (3H,s), 5.05 (1H,d), 5.07 (2H,s), 5.31 (2H,ABq), 6.02 (1H,q), 6.28 (1H,s), 6.73 (1H,s), 6.91 (4H,d), 7.00 (1H,s), 7.2–7.7 (31H,m), 7.91 (1H,s), 8.19 (1H,d).

(d) A 130 mg prompt of the product is dissolved in 0.22 ml of anisole, and 1.16 ml of trifluoroacetic acid is added under ice-cooling to conduct reaction for 3.5 hours. Isopropyl ether (6 ml) is added to the reaction mixture, and the resulting precipitate is collected by filtration and suspended in 2 ml of water. A saturated aqueous sodium hydrogen carbonate solution is added to dissolve the precipitate and to adjust the pH to 7.5. Purification by HP-20 column chromatography gives 40 mg of the title compound as a sodium salt.

NMR ($D_2O$) δ: 1.52 (3H,s), 1.54 (3H,s), 3.84 (2H,ABq), 5.33 (1H,d), 5.88 (1H,d), 6.92 (1H,s), 7.03 (1H,s), 7.06 (1H,d), 7.28 (1H,d), 7.55 (1H,s).

EXAMPLE 6

(6R, 7R)-7-[(Z)-2-(2-aminothiazol-4-yl)-2-(N-methylcarbamoyl) methoxyiminoacetamido]3-[(E)-2-(1, 5-dihydroxy-4-pyridon-2-yl)vinyl]-ceph-3-em-4-carboxylic acid (a) In 12 ml of dimethylformamide is dissolved 520 mg of (Z)-2-(2-aminothiazol-4-yl)-2-(N-methylcarbamoyl)methoxyiminoacetic acid, and 280 mg of 1-hydroxybenztriazole and 430 mg of 1,3-dicyclohexylcarbodiimide are added to the solution at room temperature. The mixture is stirred at the same temperature for about 1 hour. Then, 1.5 g of p-methoxybenzyl (6R,7R)-7amino-3[(E)-2-(4-diphenyloxy-5-p-methoxybenzyloxypyridine-N-oxide-2-yl)vinyl]-ceph-3-em-4-carboxylate is added to the solution under cooling, and the reaction is carried out at room temperature for 5–6 hours. After the reaction has finished, insolubles are removed, and extraction is conducted with ethyl acetate. The ethyl acetate layer is washed with water and saturated saline, dried over anhydrous magnesium sulfate and condensed to dryness under reduced pressure. The residue thus obtained is purified by silica gel column chromatography [chloroform-methanol (25–10:1)] to give 1 g of p-methoxybenzyl (6R,7R)-7amino-7-[(Z)-2-(2-aminothiazol-4-yl)-2-(N-methylcarbamoyl)methoxyiminoacetamido]-3-[(E)-2-(4-diphenyloxy-5-p-methoxybenzyloxypyridine-N-oxide-2yl) vinyl]-ceph-3-em-4-carboxylate.

NMR (CDCl$_3$) δ: 2.68 (3H,s), 3.62 (2H,ABq), 3.75 (3H,s), 3.80 (3H,s), 4.65 (2H,s), 5.05–5.20 (5H,m), 5.86 (1H,bs), 6.04 (2H,bs), 6.49 (1H,s), 6.75 (1H,s), 6.85 (2H,d), 6.90 (2H,d), 7.09 (1H,s), 7.20–7.58 (16H,m), 7.79 (1H,d), 7.83 (1H,s), 10.18 (1H,bs).

(b) In 1 ml of anisole is suspended 900 mg of the product obtained in (a), 3 ml of trifluoroacetic acid is added to the suspension under ice-cooling, and the reaction is carried out at the same temperature for 1.5 hours. After the reaction has finished, the reaction mixture is added dropwise to 100 ml of diisopropyl ether, and the resulting precipitate is collected by filtration and dried. The precipitate is suspended in 20 ml of water, and a clear solution is formed at pH 8.0 by adding a saturated aqueous sodium hydrogen carbonate and purified by column chromatography with DIAION HP-20 (H$_2$O) and Sephadex LH-20 (50% methanol-water) to give 280 mg of the title compound.

NMR (D$_2$O) δ: 2.82 (3H,s), 3.83 (2H,ABq), 4.75 (2H,s), 5.34 (1H,d), 5.89 (1H,d), 6.92 (1H,s), 7.04 (1H,d,J=16.4Hz), 7.12 (1H,s), 7.28 (1H,d,J=16.4Hz), 7.56 (1H,s).

EXAMPLE 7

(6R ,7R)-7 - [( Z )- 2- ( 2-aminothiazol-4-yl)-2-methoxyiminoacetamido]-3-[2-(5-hydroxy-1-methyl-4-pyridon-2-yl)vinyl]-ceph-3-em-4-carboxylic acid, trans-isomer (a) In 5 ml of dichloromethane is dissolved 0.7944 g of p-methoxybenzyl (6R,7R)-7-](Z)-2-tritylaminothiazol-4-yl)-2-methoxyimino]acetamido-3-chloromethylceph-3-em-4-carboxylate. To this solution are added 0.275 g of triphenylphosphine, 0.157 g of sodium iodide and 5 ml of water, and the reaction is conducted at room temperature for 6 hours. To the reaction mixture are added 0.350 g of 3-diphenylmethoxy-6-formyl-1-methyl-4-pyridone and 0.294 g of sodium hydrogen carbonate, and the stirring is conducted at room temperature for 14 hours. The dichloromethane layer is separated, condensed under reduced pressure and subjected to separation and purification procedures by flash column chromatography on 60 g of Wako-Gel C-300 (manufactured by Wako Pure Chemical Industries, Ltd.) with an eluent of ethyl acetate to give 0.570 g of p-methoxybenzyl-(6R,7R)-7[(Z)-2-(2-tritylaminothiazol-4-yl)-2-methoxyiminoacetamido]-3-[2-(5-diphenylmethoxy-1-methyl-4-pyridon-2-yl)vinyl]-ceph-3-em-4-carboxylate, trans-isomer and 0.118 g of the cis-isomer.

NMR CDCl$_3$) δ:
trans-isomer: 3.35 (3H,s), 3.45 (1H,d), 3.65 (1H,d), 3.71 (3H,s), 3.98 (3H,s), 4.92 (1H,d), 5.10 (2H,ABq), 5.88 (1H,dd), 6.35 (1H,d), 6.46 (1H,s), 6.63 (1H,s), 6.65 (1H,s), 6.74 (1H,s), 6.8–7.0 (3H,m), 7.1–7.6 (28H,m).
cis-isomer: 2.96 (1H,d), 3.25 (1H,d), 3.26 (3H,s), 3.74 (3H,s), 4.01 (3H,s), 4.97 (1H,d), 5.10 (2H,s), 5.87 (1H,dd), 6.10 (1H,d), 6.24 (1H,s), 6.65 (1H,s), 6.70 (1H,s), 6.75–7.0 (5H,m), 7.1–7.6 (28H,m).

(b) A 0.562 g portion of the trans-isomer of p-methoxybenzyl (6R,7R)-7-[(Z)-2-(2-tritylaminothiazol-4-yl)-2-methoxyiminoacetamido]-3-[2-(5-diphenylmethoxy-1- methyl-4-pyridon-2-yl)vinyl]-ceph-3-em-4-carboxylate is dissolved in 1.21 g of anisole, and 6.0 ml of an ice-cooled trifluoroacetic acid is added dropwise. After stirring at the same temperature for 1 hour, 60 ml of ice-cooled isopropyl ether is added, and the resulting precipitate is collected by filtration and condensed under reduced pressure. The crystal is suspended in 5 ml of water and adjusted to pH 7.5 by adding an aqueous sodium hydrogen carbonate under ice-cooling to make a solution. Purification by 40 ml of DIAION HP-20 resin column chromatography (eluent: water, 20% methanol-water) gave the title compound (0.221 g) as a sodium salt.

NMR (D$_2$O) δ: 3.85 (5H,s), 4.10 (3H,s), 5.38 (1H,d,J=5 Hz), 5.93 (1H,d,J=5 Hz), 5.73 (1H,d,J=16 Hz), 6.83 (1H,s), 7.10 (1H,s), 7.31 (1H,d,J=16 Hz), 7.63 (1H,s).

EXAMPLE 8

(6R ,7R) -7-[(Z)- 2-(2-aminothiazol-4-yl)- 2 methoxyiminoacetamido]-3-[2-(5-hydroxy-1-methyl-4-pyridon-2-yl)vinyl]-ceph-3-em-4-carboxylic acid, cis-isomer (a) The sodium salt of the title compound (0.044 g) is obtained from 0.109 g of the cis-isomer of p-methoxybenzyl (6R,7R)-7-[(Z)-2-(2-tritylaminothiazol-4-yl)-2methoxyiminoacetamido]-3-[2-(5-diphenylmethoxy-1-methyl-4-pyridon-2-yl)vinyl]-ceph-3-em-4-carboxylate in the same manner as in Example 7 (b).

NMR (D$_2$O) δ: 3.30 (1H,d,J=17Hz), 3.63 (1H,d,J=17Hz), 3.80 (3H,s), 4.06 (3H,s), 5.33 (1H,d,J=5Hz), 5.86 (1H,d,J=5Hz), 6.52 (1H,d,J=12Hz), 6.54 (1H,s), 6.76 (1H,d,J=12Hz), 7.07 (1H,s), 7.69 (1H,s).

EXAMPLE 9

(6R,7 R)-7-[(Z)-2-(2-aminothiazol-4 -yl)-2-methoxyiminoacetamido]-3-[2-(5-hydroxy-1-p-methoxybenzyl4-pyridon-2-yl)vinyl]-ceph-3-em-4-carboxylic acid, trans-isomer (a) In 3 ml of dichloromethane is dissolved 0.1271 g of p-methoxybenzyl (6R,7R)-7-[(Z)-2-(2-tritylaminothiazol-4-yl)-2-methoxyimino]acetamido-3-chloromethyl-ceph-3-em-4-carboxylate. To this solution are added 0.0441 g of triphenylphosphine, 0.0252 g of sodium iodide and 3 ml of water, and the reaction is conducted at room temperature for 6 hours. To the reaction mixture are added 0.120 g of 6-formyl-1-(p-methoxybenzyl)-3-p-methoxybenzyl)oxy-4-pyridone and 0.0471 g of sodium hydrogen carbonate, and the stirring is conducted at room temperature for 14 hours. The dichloromethane layer is separated, condensed under reduced pressure and subjected to separation and purification procedures by flash column chromatography on 30 g of Wako-Gel C-300 (manufactured by Wako Pure Chemical Industries, Ltd.) with an eluent of ethyl acetate to give 0.119 g of the trans-isomer of p-methoxybenzyl (6R,7R)-7-[(Z)-2-tritylaminothiazol-4-yl)2-methoxyiminoacetamido]-3-[2-(5-(p-methoxybenzyl)oxy-1-(p-methoxybenzyl)-4-pyridon-2-yl)vinyl]-ceph-3-em-4carboxylate.

NMR (CDCl₃) δ: 3.41 (1H,d), 3.68 (3H,s), 3.72 (3H,s), 3.73 (3H,s), 3.75 (1H,d), 3.95 (3H,s), 4.81 (1H,d), 4.9–5.3 (6H,m), 5.71 (1H,dd), 6.42 (1H,d), 6.5–7.0 (11H,m), 7.0–7.4 (21H,m), 7.63 (1H,d).

(b) A 0.102 g portion of the trans-isomer of p-methoxybenzyl (6R,7R)-7-[(Z)-2-tritylaminothiazol-4-yl)2-methoxyiminoacetamido]-3-[2-(5-(p-methoxybenzyl)oxy-1-(p-methoxybenzyl)-4-pyridon-2-yl)vinyl]-ceph-3-em-4carboxylate is dissolved in 0.25 g of anisole, and 2.0 ml of an ice-cooled trifluoroacetic acid is added dropwise. After stirring at the same temperature for 1 hour, 60 ml of ice-cooled isopropyl ether is added, and the resulting precipitate is collected by filtration and condensed under reduced pressure. The crystal is suspended in 3 ml of water and adjusted to pH 7.5 by adding an aqueous sodium hydrogen carbonate under ice-cooling to make a solution. Purification by 10 ml of DIAION HP-20 resin column chromatography (eluent: water, 30% methanol-water) gave the title compound (0.045 g) as a sodium salt.

NMR ((CD₃)₂SO) δ: 3.53 (1H,d,J=17 Hz), 3.69 (3H,s), 3.82 (3H,s), 3.86 (1H,d,J=17H), 4.0 (3H,broad), 4.9–5.3 (3H,m), 5.70 (1H,dd,J=5 Hz,8 Hz), 6.71 (1H,s), 6.78 (1H,d,J=16 Hz), 6.75–7.0 (3H,m), 7.0–7.2 (3H,m), 7.23 (1H,d,J=16 Hz), 7.51 (1H,s), 9.52 (1H,d,J=8 Hz).

EXAMPLE 10

(6R,7R)-7-[(Z)-2-(2-aminothiazol-4-yl)-2-methoxyiminoacetamido]-3-[2-(5-hydroxy-1-methoxybenzyl-4-pyridon-2-yl)vinyl]-ceph-3-em-4-carboxylic acid, cis-isomer (a) In 10 ml of dichloromethane is dissolved 1.5887 g of p-methoxybenzyl (6R,7R)-7-[(Z)-2-(2-tritylaminothiazol-4-yl)-2-methoxyimino]acetamido-3-chloromethylceph-3-em-4-carboxylate. To this solution are added 0.551 g of triphenylphosphine, 0.315 g of sodium iodide and 10 ml of water, and the mixture is stirred at room temperature for 6 hours. To the reaction mixture are added 0.868 g of 6-formyl-3-(p-methoxybenzyl)oxy-1-methoxy-4-pyridone and 0.588 g of sodium hydrogen carbonate, and the stirring is conducted at room temperature for 14 hours. The dichloromethane layer is separated, condensed under reduced pressure and subjected to separation and purification procedures by flash column chromatography on 130 g of Wako-Gel C-300 (manufactured by Wako Pure Chemical Industries, Ltd.) with an eluent of ethyl acetate to give 1.249 g of the cis-isomer of p-methoxybenzyl (6R,7R)-7-[(Z)-2-tritylaminothiazol-4-yl)2-methoxyiminoacetamido]-3-[2-(5-(p-methoxybenzyl)oxy-1-methoxy-4-pyridon-2-yl)vinyl]ceph-3-em-4-carboxylate.

NMR (CDCl₃) δ: 3.15 (1H,d), 3.40 (1H,d), 3.74 (3H,s), 3.75 (3H,s), 3.77 (3H,s), 4.03 (3H,s), 5.02 (1H,d), 5.05 (2H,s), 5.13 (2H,s), 5.90 (1H,dd), 6.22 (1H,s), 6.30 (1H,d), 6.66 (1H,s), 6.7–7.0 (6H,m), 7.09 (1H,s), 7.1–7.5 (19H,m).

(b) A 0.344 g portion of the cis-isomer of p-methoxybenzyl (6R,7R)-7-[(Z)-2-tritylaminothiazol-4-yl)2-methoxyiminoacetamido]-3-[2-(5-(p-methoxybenzyl)oxy-1-methoxy-4-pyridon-2-yl)vinyl]-ceph-3-em-4-carboxylate is dissolved in 0.72 g of anisole, and 4.0 ml of an ice-cooled trifluoroacetic acid is added dropwise. After stirring at the same temperature for 1 hour, 60 ml of ice-cooled isopropyl ether is added, and the resulting precipitate is collected by filtration and condensed under reduced pressure. The crystal is suspended in 5 ml of water and adjusted to pH 7.5 by adding a 7% aqueous sodium hydrogen carbonate solution under ice-cooling to make a solution. Purification by 30 ml of DIAION HP-20 resin column chromatography (eluent: water, 20% methanol water) gave the title compound (0.189 g) as a sodium salt.

NMR (D₂O) δ: 3.31 (1H,d,J=17 Hz), 3.66 (1H,d,J=17 Hz), 4.02 (3H,s), 4.10 (3H,s), 5.37 (1H,d,J=5Hz), 5.88 (1H,d,J=5Hz), 6.53 (1H,s), 6.54 (1H,d,J=12Hz), 6.81 (1H,d,J=12Hz), 7.04 (1H,s), 7.92 (1H,s).

EXAMPLE 11

(6R,7R)-7-[(Z)-2-(2-aminothiazol-4-yl)-2-carboxymethoxyiminoacetamido]-3-[2-(5-hydroxy-1-methyl-4-pyridon-2-yl)vinyl]-ceph-3-em-4-carboxylic acid, trans-isomer (a) In 5 ml of dichloromethane is dissolved 0.925 g of p-methoxybenzyl (6R,7R)-7-[(Z)-2-(2-tritylamino-thiazol-4-yl)-2-(butoxycarbonyl)methoxyimino]acetamido-3-chloromethylceph-3-em-4-carboxylate. To this solution are added 0.284 g of triphenylphosphine, 0.162 g of sodium iodide and 5 ml of water, and the mixture is stirred at room temperature for 6 hours. To the reaction mixture are added 0.482 g of 3-diphenylmethoxy-6-formyl1-methyl-4-pyridone and 0.303 g of sodium hydrogen carbonate, and the stirring is conducted at room temperature for 14 hours. The dichloromethane layer is separated, condensed under reduced pressure and subjected to separation and purification procedures by flash column chromatography on 60 g of Wako-Gel C-300 (manufactured by Wako Pure Chemical Industries, Ltd.) with an eluent of ethyl acetate-benzene (1:1) to give 0.690 g of the transisomer of p-methoxybenzyl (6R,7R)-7-[(Z)-2-tritylamino-thiazol-4-yl)-2-(t-butoxycarbonyl)methoxyiminoacetamido]-3-[2-(5-diphenylmethoxy-1-methyl-4-pyridon-2-yl)vinyl]-ceph-3-em-4-carboxylate.

NMR CDCl₃ δ: 1.38 (9H,s), 3.36 (3H,s), 3.5 (2H,broad s), 3.76 (3H,s), 4.70 (2H,s), 4.98 (1H,d,J=5Hz), 5.19 (2H,s), 5.81 (1H,dd,J=5Hz,8Hz), 6.32 (1H,d,J=16Hz), 6.49 (1H,s), 6.70 (1H,s), 6.78 (1H,s), 6.8–7.0 (6H,m), 7.0–7.5 (26H,m), 8.60 (1H,d,J=8Hz).

(b) A 0.670 g portion of the trans-isomer of p-methoxybenzyl (6R,7R)-7-[(Z)-2-tritylaminothiazol-4-yl)-2-(t-butoxycarbonyl)methoxyiminoacetamido]-3-[2-(5-diphenylmethoxy-1-methyl-4-pyridon-2-yl)vinyl]-ceph-3-em-4-carboxylate is dissolved in 1.42 g of anisole, and 7.0 ml of an ice-cooled trifluoroacetic acid is added dropwise. After stirring at the same temperature for 1 hour, 60 ml of ice-cooled isopropyl ether is added, and the resulting precipitate is collected by filtration and condensed under reduced pressure. The crystal is suspended in 5 ml of water and adjusted to pH 7.5 by adding a 7% aqueous sodium hydrogen carbonate solution under ice-cooling to make a solution. Purification by 80 ml of DIAION HP-20 resin column chromatography (eluent: water, 20% methanol-water) gave the title compound (0.273 g) as a sodium salt.

NMR (D₂O) δ: 3.84 (5H,s), 4.68 (2H,s), 5.38 (1H,d,J=5 Hz), 5.92 (1H,d,J=5 Hz), 6.73 (1H,d,J=16 Hz), 6.82 (1H,s), 7.13 (1H,s), 7.30 (1H,d,J=16 Hz), 7.61 (1H,s).

EXAMPLE 12

(6R,7R)-7-[(Z)-2-(2-aminothiazol-4-y1)-2-(1-methyl-1carboxy)ethoxyiminoacetamido]-3-[2-(5-hydroxy-1-methyl-4-pyridon-2-yl)vinyl]-ceph-3-em-4-carboxylic acid, trans-isomer (a) In 5 ml of dichloromethane is dissolved 0.922 g of p-methoxybenzyl (6R,7R)-7-[(Z)-2-(2-tritylaminothiazol-4-yl)-2-(1-methyl-1-t-butoxycarbonyl)ethoxyimino]acetamido-3-chloromethyl-ceph-3-em-4carboxylate. To this solution are added 0.275 g of triphenylphosphine, 0.157 g of sodium iodide and 5 ml of water, and the mixture is stirred at room temperature for 6 hours. To the reaction mixture are added 0.860 g of 3-diphenylmethoxy- 6-formyl-1-methyl-4-pyridone and 0.294 g of sodium hydrogen carbonate, and the stirring is conducted at room temperature for 14 hours. The dichloromethane layer is separated, condensed under reduced pressure and subjected to separation and purification procedures by flash column chromatography on 60 g of Wako-Gel C-300 (manufactured by Wako Pure Chemical Industries, Ltd.) with an eluent of ethyl acetate-benzene (1:1) to give 0.721 g of the trans-isomer of p-methoxybenzyl (6R,7R)-7-[(Z)-2-tritylaminothiazol-4-yl)-2-(1-methyl-1-t-butoxycarbonyl)ethoxyiminoacetamido]-3-[2-(5-diphenylmethoxy-1-methyl-4-pyridon-2-yl)vinyl]-ceph-3-em-4-carboxylate.

NMR (CDCl$_3$) δ: 1.38 (9H,s), 1.56 (3H,s), 1.61 (3H,s), 3.37 (3H,s), 3.52 (2H,broad s), 3.77 (3H,s), 4.99 (1H,d,J=5 Hz), 5.17 (1H,d,J=12 Hz), 5.24 (1H,d,J=12Hz), 5.92 (1H,dd,J=5Hz,8Hz), 6.35 (1H,d,J=16Hz), 6.49 (1H,s), 6.68 (1H,s), 6.72 (1H,s), 6.75–7.05 (4H,m), 7.1–7.5 (28H,m), 8.10 (1H,d,J=8Hz).

(b) A 0.710 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3-[2-(5-diphenylmethoxy-1-methyl-4-pyridon-2-yl)vinyl]ceph3-em-4-carboxylate is dissolved in 1.42 g of anisole, and 7.0 ml of an ice-cooled trifluoroacetic acid is added dropwise. After stirring at the same temperature for 1 hour, 60 ml of ice-cooled isopropyl ether is added, and the resulting precipitate is collected by filtration and dried under reduced pressure. The crystal is suspended in 5 ml of water and adjusted to pH 7.5 by adding a 7% aqueous sodium hydrogen carbonate solution under ice-cooling to make a solution. Purification by 180 ml of DIAION HP-20 resin column chromatography (eluent: water, 20% methanol-water) gave the title compound (0.293 g) as a sodium salt.

NMR (D$_2$O) δ: 1.62 (3H,s), 1.64 (3H,s), 3.87 (5H,s), 5.43 (1H,d,J=5 Hz), 5.94 (1H,d,J=5 Hz), 6.77 (1H,d,J=16 Hz), 6.83 (1H,s), 7.09 (1H,s), 7.32 (1H,d,J=16 Hz), 7.65 (1H,s).

EXAMPLE 13

(6R,7R)-7-[(Z)-2-aminothiazol-4-yl)-2-(1-methyl-1carboxy)ethoxyiminoacetamido]-3-[2-(5-hydroxy-4-pyridon-2-yl)vinyl]-ceph-3-em-4-carboxylic acid, trans-isomer (a) In 10 ml of dichloromethane is dissolved 1.384 g of p-methoxybenzyl (6R,7R)-7-[(Z)-2-(2-tritylaminothiazol-- 4-yl)-2-(1-methyl-1-t-butoxycarbonyl)ethoxyimino]acetamido-3-chloromethyl-ceph-3-em-4carboxylate. To this solution are added 0.413 g of triphenylphosphine, 0.237 g of sodium iodide and 10 ml of water, and the mixture is stirred at room temperature for 6 hours. To the reaction mixture are added 1.793 g of 4-acetoxy-3-(p-methoxybenzyl)oxy-6-formylpyridine and 0.441 g of sodium hydrogen carbonate, and the stirring is conducted at room temperature for 14 hours. The dichloromethane layer is separated, condensed under reduced pressure and subjected to separation and purification procedures by flash column chromatography on 60 g of Wako-Gel C-300 (manufactured by Wako Pure Chemical Industries, Ltd.) with an eluent of ethyl acetate-benzene (1:4) to give 0.227 g of the trans-isomer of p-methoxybenzyl (6R,7R)-7-[(Z)-2-tritylaminothiazol-4-yl)-2-(1-methyl-1-t-butoxycarbonyl)ethoxyiminoacetamido]-3-[2-(4-acetoxy-5-(p-methoxybenzyl)oxypyridin-2yl)vinyl]-ceph-3-em-4-carboxylate.

NMR CDCl$_3$) δ: 1.39 (9H,s), 1.58 (3H,s), 1.62 (3H,s), 3.58 (1H,d,J=17 Hz), 2.27 (3H,s), 3.72 (1H,d,J=17 Hz), 3.76 (3H,s), 3.79 (3H,s), 5.0–5.3 (5H,m), 5.93 (1H,dd,J=5Hz,8Hz), 6.57 (1H,d,J=16Hz), 6.70 (1H,s), 6.7–7.0 (6H,m), 7.08 (1H,s), 7.1–7.5 (19H,m), 7.79 (1H,d,J=16Hz), 8.60 (1H,d,J=8Hz), 8.28 (1H,s).

(b) A 0.200 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]- 3-]2-(acetoxy-5-(p-methoxybenzyl)oxypyridin-2yl)vinyl]ceph-3-em-4-carboxylate is dissolved in 0.50 g of anisole, and 3.0 ml of an ice-cooled trifluoroacetic acid is added dropwise. After stirring at the same temperature for 1 hour, 30 ml of ice-cooled isopropyl ether is added, and the resulting precipitate is collected by filtration and dried under reduced pressure. The crystal is dissolved in 6 ml of a 5% aqueous sodium hydrogen carbonate, and stirring is conducted at room temperature for 2 hours. Purification by 100 ml of DIAION HP-20 resin column chromatography (eluent: water, 20% methanol-water) gave the title compound (0.079 g) as a disodium salt.

NMR (D$_2$O) δ: 1.52 (3H,s), 1.53 (3H,s), 3.73 (1H,d,J=17 Hz), 3.82 (1H,J=1 Hz), 5.35 (1H,d,J=5 Hz), 5.89 (1H,J=5Hz), 6.56 (1H,d,J=16Hz), 7.72 (1H,s), 7.03 (1H,s), 7.33 (1H,d,J=16Hz), 7.59 (1H,s).

EXAMPLE 14

(6R,7R)-7-[(Z)-2-aminothiazol-4-y1)-2-(1-methyl-1carboxy)ethoxyiminoacetamido]-3-[2-(5-hydroxy-1-(2-(N,N-dimethylamino)ethyl)-4-pyridon-2-yl)vinyl]-ceph-3-em-4carboxylic acid, trans-isomer (a) In 5 ml of dichloromethane is dissolved 1.0326 g of p-methoxybenzyl (6R,7R)-7-[(Z)-2-(2-tritylamino- thiazol-4-yl)-2-(1-methyl-1-diphenylmethoxycarbonyl)ethoxyimino]acetamido-3-chloromethyl-ceph-3-em-4carboxylate. To this solution are added 0.275 g of triphenylphosphine, 0.157 g of sodium iodide and 5 ml of water, and the mixture is stirred at room temperature for 6 hours. To the reaction mixture are added 0.730 g of 3- diphenylmethoxy-6-formyl-1-(2-(N,N-dimethylamino)ethyl)4-pyridone and 0.294 g of sodium hydrogen carbonate, and the stirring is conducted at room temperature for 14 hours. The dichloromethane layer is separated, condensed under reduced pressure and subjected to separation and purification procedures by flash column chromatography on 100 g of Wako-Gel C-300 (manufactured by Wako Pure Chemical Industries, Ltd.) with an eluent of chloroform-methanol (10:1) to give 0.838 g of the trans-isomer of p-methoxybenzyl (6R, 7R)-7-[(Z)-2-tritylaminothiazol-4-yl)-2-(1- methyl-1-diphenylmethoxycarbonyl)ethoxyiminoacetamido]-3-[2-(5-(diphenylmethoxy-1-(2-(N,N-dimethylamino) ethyl)-4-pyridon-2-yl)vinyl]ceph-3-em-4carboxylate.

NMR CDCl₃) δ: 1.67 (3H,s), 1.69 (3H,s), 2.06 (6H,s), 2.32 (2H,t,J=6Hz), 3.43 (2H,broad s), 3.66 (2H,t,J=6Hz), 3.77 (3H,s), 4.94 (1H,d,J=5Hz), 5.23 (2H,broad s), 5.91 (1H,dd,J=5Hz,8Hz), 6.46 (1H,d,J=16Hz), 6.52 (1H,s), 6.59 (1H,s), 6.67 (1H,s), 6.75–6.95 (4H,m), 7.1–7.6 (38H,m).

(b) A 0.827 g portion of the trans-isomer of p-methoxybenzyl (6R,7R)-7-[(Z)-2-tritylaminothiazol-4-yl)2-(1-methyl-1-diphenylmethoxycarbonyl)ethoxyiminoacetamido]-3-[2-(5-(diphenylmethoxy-1-(2-(N,N-dimethylamino) ethyl)-4-pyridon-2-yl)vinyl]ceph-3-em-4carboxylate is dissolved in 1.70 g of anisole, and 9.0 ml of an ice-cooled trifluoroacetic acid is added dropwise. After stirring at the same temperature for 1 hour, 60 ml of ice-cooled isopropyl ether is added, and the resulting precipitate is collected by filtration and dried under reduced pressure. The crystal is suspended in 5 ml of water and adjusted to pH 7.5 by adding a 7% aqueous sodium hydrogen carbonate solution under ice-cooling to make a solution. Purification by 180 ml of DIAION HP-20 resin column chromatography (eluent: water, 20% methanol-water) gave the title compound (0.362 g) as a disodium salt.

NMR (D₂O) δ: 1.63 (3H,s), 1.64 (3H,s), 2.82 (6H,s), 3.34 (2H,t,J=6Hz), 3.89 (2H,s), 4.51 (2H,t,J=6Hz), 5.41 (1H,d,J=5Hz), 5.92 (1H,d,J=5Hz), 6.72 (1H,d,J=16Hz), 5.79 (1H,s), 7.08 (1H,s), 7.32 (1H,d,J=16Hz), 7.70 (1H,s).

EXAMPLE 15

(6R,7R)-7-[(Z)-2-aminothiazol-4-yl)-2-(1-methyl-1-carboxy) ethoxyiminoacetamido]-3-[2-(5-hydroxy-1-(2,2-dimethoxyethyl)-4-pyridon-2-yl)vinyl]-ceph-3-em-4carboxylic acid, trans-isomer (a) In 10 ml of acetone is dissolved 1.0326 g of p-methoxybenzyl (6R, 7R)-7-[(z)-2-tritylaminothiazol-4-yl)-2-methyl-1-diphenylmethoxycarbonyl)ethoxyimino]-acetamido-3-chloromethyl-ceph-3-em-4-carboxylate. To this solution are added 0.275 g of triphenylphosphine and 0.157 g of sodium iodide, and the mixture is stirred at room temperature for 2 hours. The reaction mixture is condensed to dryness under reduced pressure, and the residue is dissolved in 10 ml of dichloromethane. To the solution are added 0.787 g of 3-diphenylmethoxy-6-formyl1-(2,2-dimethoxyethyl)-4-pyridone, 0.294 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 100 g of Wako-Gel C-300 (manufactured by Wako Pure Chemical Industries, Ltd.) with an eluent of ethyl acetate-benzene (1:1) to give 0.776 g of the trans-isomer of p-methoxybenzyl (6R,7R)-7-[(Z)-2-tritylaminothiazol-4-yl)-2-(1-methyl-1-diphenylmethoxycarbonyl)- ethoxyiminoacetamido-3-[2-(5-(diphenylmethoxy-1-(2,2-dimethoxyethyl)-4-pyridon-2-yl)vinyl]ceph-3-em-4carboxylate.

NMR (CDCl₃) δ: 1.66 (3H,s), 1.68 (3H,s), 3.17 (3H,s), 3.18 (3H,s), 3.41 (2H,broad s), 3.67 (2H,d,J=5Hz), 3.77 (3H,s), 3.95–4.25 (1H,m), 4.91 (1H,d,J=5Hz), 5.22 (2H,s), 5.91 (1H,dd,J=5Hz,8Hz), 6.50 (1H,s), 6.51 (1H,d,J=16Hz), 6.59 (1H,s), 6.69 (1H,s), 6.7–7.0 (4H,m), 7.0–7.5 (38H,m).

(b) A 0.770 g portion of the trans-isomer of p-methoxybenzyl (6R,7R)-7-[(Z)-2-tritylaminothiazol-4-yl)2-(1-methyl-1-diphenylmethoxycarbonyl)ethoxyiminoacetamido]-3-[2-(5-(diphenylmethoxy-1-(2,2-dimethoxyethyl)-4-pyridon-2-yl)vinyl]ceph-3-em- 4-carboxylate is dissolved in 1.60 g of anisole, and 8.0 ml of an ice-cooled trifluoroacetic acid is added dropwise. After stirring at the same temperature for 1 hour, 60 ml of ice-cooled isopropyl ether is added, and the resulting precipitate is collected by filtration and dried under reduced pressure. The crystal is suspended in 5 ml of water and adjusted to pH 7.5 by adding a 7% aqueous sodium hydrogen carbonate solution under ice-cooling to make a solution. Purification by 80 ml of DIAION HP-20 resin column chromatography (eluent: water, 30% methanol-water) gave the title compound (0.270 g) as a disodium salt.

NMR (D₂O) δ: 1.66 (3H,s), 1.67 (3H,s), 3.53 (6H,s), 3.91 (2H,s), 4.37 (2H,d,J=5Hz), 4.7–5.0 (1H,m), 5.43 (1H,d,J=5Hz), 5.96 (1H,d,J=5Hz), 6.83 (1H,s), 6.85 (1H,d,J=16Hz), 7.12 (1H,s), 7.69 (1H,s).

EXAMPLE 16

(6R,7R)-7-[(Z)-2-aminothiazol-4-yl)-2-(1-methyl-1carboxy)ethoxyiminoacetamido]-3-[2-(5-hydroxy-1-formylmethyl-4-pyridon-2-yl)vinyl]-ceph-3-em-4-carboxylic acid, trans-isomer (b) A 0.120 g portion of the trans-isomer of (6R,7R)-7-[(Z)-2-aminothiazol-4-yl)-2-(1-methyl-1carboxy)ethoxyiminoacetamido]-3-[2-(5-hydroxy-1-(2,2-dimethoxyethyl)-4-pyridon-2-yl)vinyl]ceph-3-em-4carboxylic acid is dissolved in ice-cooled 2N hydrochloric acid, and stirring is conducted for 1 hour. The reaction mixture is condensed under reduced pressure. An ice-cooled 7% aqueous sodium hydrogen carbonate solution is added in order to adjust pH to 7.5 and to make a solution. Purification by 40 ml of DIAION HP-20 resin column chromatography (eluent: water, 20% methanol water) gave the title compound (0.70 g) as a disodium hydrate.

NMR (D₂O) δ: 1.63 (3H,s), 1.64 (3H,s), 3.91 (2H,s), 5.41 (1H,s), 5.44 (1H,d,J=5Hz), 5.96 (1H,d,J=5Hz), 6.84 (1H,s), 6.87 (1H,d,J=16Hz), 7.11 (1H,s), 7.25 (1H,d,J=16Hz), 7.65 (1H,s).

EXAMPLE 17

(6R,7R)-7-[(Z)-2-aminothiazol-4-yl)-2-(1-methyl-1(1-carboxy)ethoxyiminoacetamido]-3-[2-(5-hydroxy-1-allyl-4-pyridon-2-yl)vinyl]-ceph-3-em-4-carboxylic acid, trans-isomer (a) In 5 ml of acetone is dissolved 0.5158 g of p-methoxybenzyl (6R,7R)-7-[(Z)-2-(2-tritylaminothiazol-4-yl)-2-(1-methyl-1-diphenylmethoxycarbonyl)ethoxyimino]acetamido-3-acetamido-3-chloromethyl-ceph-3-em-4-carboxylate. To this solution are added 0.138 g of triphenylphosphine and 0.079 g of sodium iodide at room temperature, and the mixture is stirred for 2 hours. The reaction mixture is condensed to dryness under reduced pressure, and the residue is dissolved in 5 ml of dichloromethane. To the solution are added 0.345 g of 3-diphenylmethoxy-1-allyl6-formyl-4-pyridone, 0.147 g of sodium hydrogen carbonate and 5 ml of water, and the stirring is conducted at room temperature for 14 hours. The dichloromethane layer is separated, condensed under reduced pressure and subjected to separation and purification procedures by flash column chromatography on 50 g of Wako-Gel C-300 (manufactured by Wako Pure Chemical Industries, Ltd.) with an eluent of ethyl acetate-benzene (1:1) to give 0.438 g of the transisomer of p-methoxybenzyl (6R,7R)-7-[(Z)-2-tritylamino- thiazol-4-yl)-2-(1-methyl-1-diphenylmethoxycarbonyl)ethoxyiminoacetamido]-3-[2-(5-(diphenylmethoxy-1-allyl-4-pyridon-2-yl)vinyl]ceph-3-em-4-carboxylate.

NMR CDCl$_3$) δ: 1.65 (3H,s), 1.67 (3H,s), 3.37 (2H,s), 3.89 (3H,s), 4.1–4.3 (2H,m), 4.70 (1H,dm,J=17Hz), 4.91 (1H,d,J=5Hz), 5.0–5.3 (3H,m), 5.5–5.9 (1H,m), 5.91 (1H,dd,J=5Hz,8Hz), 6.27 (1H,d,J=16Hz), 6.54 (1H,s), 6.59 1,H,s), 6.6–7.0 (5H,m), 7.0–7.5 (38H,m).

(b) A 0.430 g portion of the trans-isomer of p-methoxybenzyl (6R,7R)-7-[(Z)-2-tritylaminothiazol-4-yl)2-(1-methyl-1-diphenylmethoxycarbonyl)ethoxyiminoacetamido]- 3-[2-(5-(diphenylmethoxy-1-allyl-4-pyridon-2yl)vinyl]ceph-3-em-4-carboxylate is dissolved in 0.80 g of anisole, and 4.0 ml of an ice-cooled trifluoroacetic acid is added dropwise. After stirring at the same temperature for 1 hour, 30 ml of ice-cooled isopropyl ether is added, and the resulting precipitate is collected by filtration and dried under reduced pressure. The crystal is suspended in 3 ml of water and adjusted to pH 7.5 by adding a 7% aqueous sodium hydrogen carbonate solution under ice-cooling to make a solution. Purification by 40 ml of DIAION HP-20 resin column chromatography (eluent: water, 30% methanol-water) gave the title compound (0.171 g) as a disodium salt.

NMR (D$_2$)) δ: 1.65 (6H,s), 3.86 (2H,s), 4.7–4.85 (2H,m), 5.11 (1H,d,J=17Hz), 5.3–5.6 (2H,m), 5.85–6.25 (1H,m), 5.96 (1H,d,J=5Hz), 6.72 (1H,d,J=16Hz), 5.87 (1H,s), 7.33 (1H,d,J=16Hz), 7.69 (1H,s).

EXAMPLE 18

(6R,7R)-7-[(Z)-2-aminothiazol-4-yl)-2-(1-methyl-1carboxy)ethoxyiminoacetamido]-3-[2-(5-hydroxy-1-isopropyl-4-pyridon-2-yl)vinyl]-ceph-3-em-4-carboxylic acid, trans-isomer (a) In 10 ml of acetone is dissolved 1.0326 g of p-methoxybenzyl (6R,7R)-7-[(Z)-2-(2-tritylaminothiazol-4-yl)-2-(1-methyl-1-diphenylmethoxycarbonyl)ethoxyimino]- acetamido-3-chloromethyl-ceph-3-em-4-carboxylate. To this solution are added 0.2754 g of triphenylphosphine and 0.157 g of sodium iodide at room temperature, and the mixture is stirred for 2 hours. The reaction mixture is condensed to dryness under reduced pressure, and the residue is dissolved in 10 ml of dichloromethane. To the solution are added 1.3897 g of 3-diphenylmethoxy-1-isopropyl-6-formyl-4-pyridone, 0.294 g of sodium hydrogen carbonate and 5 ml of water, and the stirring is conducted at room temperature for 14 hours. The dichloromethane layer is separated, condensed under reduced pressure and subjected to separation and purification procedures by flash column chromatography on 50 g of Wako-Gel C-300 (manufactured by Wako Pure Chemical Industries, Ltd.) with an eluent of ethyl acetate-benzene (1:1) to give 0.974 g of the trans-isomer of p-methoxybenzyl (6R,7R)-7-[(Z)-2-tritylaminothiazol-4-yl)-2-(1-methyl-1-diphenylmethoxycarbonyl)-ethoxyiminoacetamido]-3-[2-(5-(diphenylmethoxy-1-isopropyl-4-pyridon-2-yl)vinyl]ceph-3-em-4-carboxylate.

NMR CDCl$_3$) δ: 1.14 (6H,d,J=7Hz), 1.66 (3H,s), 1.68 (3H,s), 3.43 (2H,s), 3.77 (3H,s), 4.0–4.45 (1H,m), 4.94 (1H,d,J=5Hz), 5.23 (2H,s), 5.91 (1H,dd,J=5Hz,8Hz), 6.41 (1H,d,J=16Hz), 6.43 (1H,s), 6.58 (1H,s), 6.61 (1H,s), 6.7–7.0 (5H,m), 7.0–7.6 (38H,m).

(b) A 0.969 g portion of the trans-isomer of p-methoxybenzyl (6R,7R)-7-[(Z)-2-tritylaminothiazol-4-yl)2-(1-methyl-1-diphenylmethoxycarbonyl)ethoxyiminoacetamido]-3-[2-(5-(diphenylmethoxy-1-isopropyl-4-pyridon-2-yl)vinyl]ceph-3-em-4-carboxylate is dissolved in 2.0 g of anisole, and 10.0 ml of an ice-cooled trifluoroacetic acid is added dropwise. After stirring at the same temperature for 1 hour, 70 ml of ice-cooled isopropyl ether is added, and the resulting precipitate is collected by filtration and dried under reduced pressure. The crystal is suspended in 6 ml of water and adjusted to pH 7.5 by adding a 7% aqueous sodium hydrogen carbonate solution under ice-cooling to make a solution. Purification by 40 ml of DIAION HP-20 resin column chromatography (eluent: water, 30% methanol-water) gave the title compound (0.483 g) as a disodium salt.

NMR (D$_2$O) δ: 1.56 (6H,d,J=7Hz), 1.64 (6H,s), 3.90 (2H,s), 5.42 (1H,d,J=5Hz), 5.4–5.8 (1H,m), 5.96 (1H,d,J=5Hz), 6.75 (1H,s), 6.89 (1H,d,J=16Hz), 7.11 (1H,s), 7.24 (1H,d,J=16Hz), 7.79 (1H,s).

EXAMPLE 19

(6R,7R)-7-[(Z)-2-aminothiazol-4-yl)-2-(1-methyl-1carboxy)ethoxyiminoacetamido]-3-[2-(5-hydroxy-1-(2-furyl)methyl-4-pyridon-2-yl)vinyl]-ceph-3-em-4-carboxylic acid, trans-isomer (a) In 20 ml of acetone is dissolved 1.845 g of p-methoxybenzyl (6R,7R)-7-[(Z)-2-(2-tritylaminothiazol-4-yl)-2-(1-methyl-1-t-butoxycarbonyl)ethoxyimino]acetamido3-chloromethyl-ceph-3-em-4-carboxylate. To this solution are added 0.551 g of triphenylphosphine and 0.315 g of sodium iodide at room temperature, and the mixture is stirred for 2 hours. The reaction mixture is condensed to dryness under reduced pressure, and the residue is dissolved in 20 ml of dichloromethane. To the solution are added 1.542 g of 3-diphenylmethoxy-1-(2-furyl)methyl-6-formyl-4-pyridone, 0.588 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 150 g of Wako-Gel C-300 (manufactured by Wako Pure Chemical Industries, Ltd.) with an eluent of ethyl acetate-benzene (1:1) to give 0.940 g of the transisomer of p-methoxybenzyl (6R,7R)-7-[(Z)-2-tritylamino- thiazol-4-yl)-2-(1-methyl-1-t-butoxycarbonyl)ethoxyiminoacetamido]-3-[2-(5-(diphenylmethoxy-1-(2-furyl)methyl-4-pyridon-2-yl)vinyl]ceph-3-em-4carboxylate.

NMR CDCl$_3$) δ: 1.49 (9H,s), 1.58 (3H,s), 1.62 (3H,s), 3.51 (2H,broad s), 3.78 (3H,s), 4.70 (2H,s), 4.99 (1H,d,J=5Hz), 5.21 (2H,s), 5.93 (1H,d,J=5Hz,8Hz), 5.98 (1H,d,J=5Hz), 6.26 (1H,dd,J=2Hz,5Hz), 6.47 (1H,s), 6.52 (1H,d,J=16Hz), 6.62 (1H,s), 6.69 (1H,s), 6.7–7.1 (4H,m), 7.1–7.5 (28H,s), 8.12 (1H,d,J=8Hz).

(b) A 0.934 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3[2-(5-(diphenylmethoxy-1-(2-furyl)methyl-4-pyridon-2yl)vinyl]ceph-3-m-4-carboxylate is dissolved in 2.0 g of anisole, and 10.0 ml of an ice-cooled trifluoroacetic acid is added dropwise. After stirring at the same temperature for 3 hours, 70 ml of ice-cooled isopropyl ether is added, and the resulting precipitate is collected by filtration and dried under reduced pressure. The crystal is suspended in 6 ml of water and adjusted to pH 7.5 by adding a 7% aqueous sodium hydrogen carbonate solution under ice-cooling to make a solution. Purification by 40 ml of DIAION HP-20 resin column chromatography (eluent: water, 20% methanol-water) gave the title compound (0.430 g) as a disodium salt.

NMR ($D_2O$) δ: 1.64 (6H,s), 3.87 (2H,s), 5.3–5.5 (3H,m), 5.96 (1H,d,J=5Hz), 6.5–7.0 (4H,m), 7.10 (1H,s), 7.17 (1H,d,J=16Hz), 7.60 (1H,s), 7.7–7.8 (1H,m).

EXAMPLE 20

(6R,7R)-7-[(Z)-2-aminothiazol-4-yl)-2-(1-methyl-1carboxy)ethoxyiminoacetamido]-3-[2-(5-hydroxy-1-methoxycarbonylmethyl-4-pyridon-2-yl)vinyl]-ceph-3-em-4carboxylic acid, trans-isomer (a) In 20 ml of acetone is dissolved 1.845 g of p-methoxybenzyl (6R,7R)-7-[(Z)-2-(2-tritylaminothiazol-4-yl)-2-(1-methyl-1-t-butoxycarbonyl)ethoxyimino]acetamido3-chloromethyl-ceph-3-em-4-carboxylate. To this solution are added 0.551 g of triphenylphosphine and 0.315 g of sodium iodide at room temperature, and the mixture is stirred for 2 hours. The reaction mixture is condensed to dryness under reduced pressure, and the residue is dissolved in 20 ml of dichloromethane. To the solution are added 1.050 g of 3-diphenylmethoxy-1-methoxycarbonylmethyl-6-formyl-4-pyridone, 0.588 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 150 g of Wako-Gel C-300 (manufactured by Wako Pure Chemical Industries, Ltd.) with an eluent of ethyl acetate-benzene (1:1) to give 1.432 g of the trans-isomer of p-methoxybenzyl (6R,7R)-7-[(Z)-2-tritylaminothiazol-4yl)-2-(5-(diphenylmethoxy-1-methoxycarbonylmethyl-4-pyridon-2-yl)vinyl]ceph-3-em-4-carboxylate.

NMR ($CDCl_3$) δ: 1.47 (9H,s), 1.56 (3H,s), 1.61 (3H,s), 3.47 (2H,s), 3.65 (3H,s), 3.78 (3H,s), 4.29 (2H,s), 4.99 (1H,d,J=5Hz), 5.20 (2H,s), 5.93 (1H,dd,J=5Hz,8Hz), 6.23 (1H,d,J=16Hz), 6.46 (1H,s), 6.65 (1H,s), 6.69 (1H,s), 6.7–7.1 (4H,m), 7.1–7.5 (27H,m), 8.09 (1H,d,J=8Hz).

(b) A 1.423 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3-[2-(5-(diphenylmethoxy-1-methoxycarbonylmethyl-4-pyridon2-yl)vinyl]ceph-3-em-4-carboxylate is dissolved in 3.0 g of anisole, and 15.0 ml of an ice-cooled trifluoroacetic acid is added dropwise. After stirring at the same temperature for 3 hours, 100 ml of ice-cooled isopropyl ether is added, and the resulting precipitate is collected by filtration and dried under reduced pressure. The crystal is suspended in 10 ml of water and adjusted to pH 7.5 by adding a 7% aqueous sodium hydrogen carbonate solution under ice-cooling to make a solution. Purification by 100 ml of DIAION HP-20 resin column chromatography (eluent: water, 20% methanol-water) gave the title compound (0.680 g) as a disodium salt.

NMR ($D_2O$) δ: 1.61 (3H,s), 1.62 (3H,s), 3.82 (2H,s), 3.90 (3H,s), 5.13 (2H,s), 5.41 (1H,d,J=5Hz), 5.97 (1H,d,J=5Hz), 6.62 (1H,d,J=16Hz), 6.85 (1H,s), 7.10 (1H,s), 7.32 (1H,d,J=16Hz), 7.68 (1H,s).

EXAMPLE 21

(6R,7R)-7-[(Z)-2-aminothiazol-4-y1)-2-(1-methyl-1-carboxy)ethoxyiminoacetamido]-3-[2-(5-hydroxy-1-(4-pyridyl)methyl-4-pyridon-2-y1)vinyl]-ceph-3-em-4carboxylic acid, trans-isomer (a) In 20 ml of acetone is dissolved 1.845 g of p-methoxybenzyl (6R,7R)-7-[(Z)-2-(2-tritylaminothiazol-4-yl)-2-(1-methyl-1-t-butoxycarbonyl)ethoxyimino]acetamido- 3-chloromethyl-ceph-3-em-4-carboxylate. To this solution are added 0.551 g of triphenylphosphine and 0.315 g of sodium iodide at room temperature, and the mixture is stirred for 2 hours. The reaction mixture is condensed to dryness under reduced pressure, and the residue is dissolved in 20 ml of dichloromethane. To the solution are added 1.189 g of 3-diphenylmethoxy-1-(4pyridyl)methyl-6-formyl-4-pyridone, 0.588 g of sodium hydrogen carbonate and 20 ml of water, and the stirring is conducted at room temperature for 14 hours. The dichloromethane layer is separated, condensed under reduced pressure and subjected to separation and purification procedures by flash column chromatography on 100 g of Wako-Gel C-300 (manufactured by Wako Pure Chemical Industries, Ltd.) with an eluent of ethyl acetate to give 2.340 g of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3-[2-(5-(diphenylmethoxy-1-(4-pyridyl)methyl-4-pyridon-2yl)vinyl]ceph-3-em-4-carboxylate.

NMR $CDCl_3$) δ: 1.46 (9H,s), 1.55 (3H,s), 1.59 (3H,s), 3.30 (2H,s), 3.77 (3H,s), 4.79 (2H,s), 4.92 (1H,d,J=5Hz), 5.19 (2H,s), 5.89 (1H,dd,J=5Hz,8Hz), 6.11 (1H,d,J=16Hz), 6.52 (2H,s), 6.55–7.1 (4H,m), 7.1–7.6 (30H,m), 8.08 (1H,d,J=8Hz), 8.4–8.5 (2H,m).

(b) A 1.160 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3[2-(5-(diphenylmethoxy-1-(4-pyridyl)methyl-4-pyridon-2yl)vinyl]ceph-3-em-4-carboxylate is dissolved in 2.5 g of anisole, and 12.0 ml of an ice-cooled trifluoroacetic acid is added dropwise. After stirring at the same temperature for 3 hours, 70 ml of ice-cooled isopropyl ether is added, and the resulting precipitate is collected by filtration and dried under reduced pressure. The crystal is suspended in 7 ml of water and adjusted to pH 7.5 by adding a 7% aqueous sodium hydrogen carbonate solution under ice-cooling to make a solution. Purification by 100 ml of DIAION HP-20 resin column chromatography (eluent: water, 30% methanol-water) gave the title compound (0.276 g) as a disodium salt.

NMR ($D_2O$) δ: 1.62 (6H,s), 3.61 (2H,s), 6.32 (1H,d,J=5Hz), 5.53 (2H,broad s), 6.92 (1H,d,J=5Hz), 6.54 (1H,d,J=16Hz), 7.69 (1H,s), 7.07 (1H,s), 7.15–7.4 (3H,m), 7.81 (1H,s), 8.5–8.65 (2H,m).

EXAMPLE 22

(6R,7R)-7-[(Z)-2-aminothiazol-4-yl)-2-(1-methyl-1carboxy)ethoxyiminoacetamido]-3-[2-(5-hydroxy-1-(1-methyl-4-pyridyl)methyl-4-pyridon-2-yl)vinyl]-ceph-3-em4-carboxylic acid, trans-isomer A 1.160 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3[2-(5-(diphenylmethoxy-1-(4-pyridyl)methyl-4-pyridon-2yl)vinyl]ceph-3-em-4-carboxylate is dissolved in 10 ml of benzene, and 1 ml of methyl iodide is added to the solution at room temperature. Stirring is continued for 14 hours. The reaction mixture is condensed under reduced pressure, and 20 ml of ethyl acetate is added. The resulting precipitate is collected by filtration and dissolved in 2.5 g of anisole, and 12.0 ml of trifluoroacetic acid is added dropwise under ice-cooling. After stirring at the same temperature for 3 hours, 70 ml of ice-cooled isopropyl ether is added, and the resulting precipitate is collected by filtration and dried under reduced pressure. The crystal is suspended in 7 ml of water and adjusted to pH 7.5 by adding a 7% aqueous sodium hydrogen carbonate solution under ice-cooling to make a solution. Purification by 100 ml of DIAION HP-20 resin column chromatography (eluent: water, 30% methanol-water) gave the title compound (0.317 g) as a monosodium salt.

NMR (D$_2$O) δ: 1.63 (6H,s), 3.65 (2H,broad s), 4.16 (3H,s), 5.35 (1H,d,J=5Hz), 5.80 (1H,d,J=5Hz), 5.87 (2H,broad s), 6.53 (1H,d,J=16Hz), 6.85 (1H,s), 7.02 (1H,s), 7.18 (1H,d,J=16Hz), 7.7–7.9 (3H,m), 8.7–8.9 (2H,m).

EXAMPLE 23

(6R,7R)-7-[(Z)-2-aminothiazol-4-yl)-2-(1-methyl-1carboxy) ethoxyiminoacetamido]-3-[2-(5-hydroxy-1-carboxymethyl-4-pyridon-2-yl)vinyl]-ceph-3-em-4carboxylic acid, trans-isomer (a) In 10 ml of acetone is dissolved 0.9225 g of p-methoxybenzyl (6R,7R)-7-[(Z)-2-(2-tritylaminothiazol-4-yl)-2-(1-methyl-1-t-butoxycarbonyl)ethoxyimino]acetamido3-chloromethyl-ceph-3-em-4-carboxylate. To this solution are added 0.275 g of triphenylphosphine and 0.157 g of sodium iodide at room temperature, and the mixture is stirred for 2 hours. The reaction mixture is condensed to dryness under reduced pressure, and the residue is dissolved in 10 ml of dichloromethane. To the solution are added 0.794 g of 3-diphenylmethoxy-1-diphenylmethoxy- carbonylmethyl-6-formyl-4-pyridone, 0.294 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 50 g of Wako-Gel C-300 (manufactured by Wako Pure Chemical Industries, Ltd.) with an eluent of ethyl acetate-benzene (1:2) to give 0.866 g of the trans-isomer of p-methoxybenzyl (6R,7R)-7-[(Z)-2-tritylaminothiazol-4--yl)-2-(1-methyl-1-t-butoxycarbonyl)ethoxyiminoacetamido]3-[2-(5-(diphenylmethoxy-1-diphenylmethoxycarbonylmethyl-4-pyridon-2-yl)vinyl]ceph-3-em-4-carboxylate.

NMR (CDCl$_3$) δ: 1.48 (9H,s), 1.58 (3H,s), 1.63 (3H,s), 3.02 (2H,s), 3.77 (3H,s), 4.34 (2H,s), 4.90 (1H,d,J=5Hz), 5.18 (2H,s), 5.92 (1H,dd,J=5Hz,8Hz), 5.94 (1H,d,J=16Hz), 6.51(1H,s), 6.64 (1H,s), 6.70 (1H,s), 6.75–7.0 (5H,m), 7.0–7.5 (39H,m), 8.12 (1H,d,J=8Hz)

(b) A 0.860 g portion of the trans-isomer of p-methoxybenzyl (6R,7R)-7-[(Z)-2-tritylaminothiazol-4-yl)- 2-(1-methyl-1-t-butoxycarbonyl)ethoxyiminoacetamido]-3-[2-(5-(diphenylmethoxy-1-diphenylmethoxycarbonylmethyl-4-pyridon-2-yl)vinyl]ceph-3-em-4-carboxylate is dissolved in 2.0 g of anisole, and 10.0 ml of an ice-cooled trifluoroacetic acid is added dropwise. After stirring at the same temperature for 3 hours, 50 ml of ice-cooled isopropyl ether is added, and the resulting precipitate is collected by filtration and dried under reduced pressure. The crystal is suspended in 5 ml of water and adjusted to pH 7.5 by adding a 7% aqueous sodium hydrogen carbonate solution under ice-cooling to make a solution. Purification by 150 ml of DIAION HP-20 resin column chromatography (eluent: water, 10% methanol-water) gave the title compound (0.243 g) as a trisodium salt.

NMR (D$_2$O) δ: 1.65 (6H,s), 3.90 (2H,s), 4.75 (2H,s), 5.42 (1H,d,J=5Hz), 5.97 (1H,d,J=5Hz), 6.58 (1H,d,J=16Hz), 6.67 (1H,s), 7.13 (1H,s), 7.31 (1H,d,J=16Hz), 7.50 (1H,s).

EXAMPLE 24

Injection preparation

It was distributed aseptically into vials in such a way that the compound of Example 5 is contained in a titer of 1,000 mg/vial.

EXAMPLE 25

Capsule

Compound of Example 5: 250 parts (titer)
Lactose: 60 parts (titer)
Magnesium stearate: 5 parts (titer)

These components were blended homogeneously and charged into capsules so that the compound is contained in a titer of 250 mg/capsule.

EXAMPLE 26 soft capsules for rectal use

The compound of Example 5 is homogeneously blended with the following base and charged into a rectal soft capsules so that the titer of each capsule is at 250 mg:

olive oil: 160 parts
polyoxyethylenelaurylether: 10 parts
sodium hexametaphosphate: 5 parts

EXAMPLE 27

(6R,7R)-7-[(Z)-2-aminothiazol-4-yl)-2-(1-methyl-1carboxy)ethoxyiminoacetamido]-3-[2-(5-hydroxy-1-(2-carboxyethyl)-4-pyridon-2-yl)vinyl]-ceph-3-em-4carboxylic acid, trans-isomer (a) In 15 ml of acetone is dissolved 1.384 g of p-methoxybenzyl (6R,7R)-7-[(Z)-2-(2-tritylaminothiazol-4-yl)-2-(1-methyl-1-t-butoxycarbonyl)ethoxyimino]acetamido3-chloromethyl-ceph-3-em-4-carboxylate. To this solution are added 0.413 g of triphenylphosphine and 0.236 g of sodium iodide at room temperature, and the mixture is stirred for 1 hour. The reaction mixture is condensed to dryness under reduced pressure, and the residue is dissolved in 15 ml of dichloromethane. To the solution are added 1.223 g of diphenylmethyl 3-(3-diphenylmethoxy6-formyl-4-pyridone- 1-yl)propionate, 0.441 g of sodium hydrogen carbonate and 12 ml of water, and the stirring is conducted at room temperature for 14 hours. The dichloromethane layer is separated, condensed under reduced pressure and subjected to separation and purification procedures by flash column chromatography on 80 g of Wako-Gel C-300 (manufactured by Wako Pure Chemical Industries, Ltd.) with an eluent of ethyl acetate-benzene (1:2) to give 1.617 g of the trans-isomer of p-methoxybenzyl (6R,7R)-7-[(Z)-2-tritylaminothiazol-4-yl)-2-(1-methyl-1-t-butoxycarbonyl)ethoxyiminoacetamido]3-[2-(5-(diphenylmethoxy-1-(2-diphenylmethoxy-carbonyl)ethyl)-4-pyridon-2-yl)vinyl]ceph-3-em-4carboxylate.

NMR CDCl$_3$) δ: 1.38 (9H,s), 1.57 (3H,s), 1.62 (3H,s), 2.59 (2H,t,J=7Hz), 3.40 (2H,broad s), 3.77 (3H,s), 3.91 (2H,t,J=7Hz), 4.96 (1H,J=5Hz), 5.20 (2H,broad s), 5.94 (1H,dd,J=5Hz,8Hz), 6.39 (1H,d,J=16Hz), 6.44 (1H,s), 6.62 (1H,s), 6.72 (1H,s), 6.73–7.5 (43H,m), 8.10 (1H,d,J=8Hz).

(b) A 1.602 g portion of the trans-isomer of p-methoxybenzyl (6R, 7R)-7-[(Z)-2-tritylaminothiazol-4-yl)- 2-(1-methyl-1-t-butoxycarbonyl)ethoxyiminoacetamido]-3-[2-(5-(diphenylmethoxy-1-(2-diphenylmethoxycarbonyl) ethyl)-4-pyridon-2-yl)vinyl]ceph-3-em-4carboxylate is dissolved in 3.2 g of anisole, and 16 ml of an ice-cooled trifluoroacetic acid is added dropwise. After stirring at the same temperature for 4 hours, 80 ml of ice-cooled isopropyl ether is added, and the resulting precipitate is collected by filtration and dried under reduced pressure. The crystal is suspended in 10 ml of water and adjusted to pH 7.5 by adding a 7% aqueous sodium hydrogen carbonate solution under ice-cooling to make a solution. Purification by 200 ml of DIAION HP-20 resin column chromatography (eluent: water, 10% methanol-water) gave the title compound (0.676 g) as a trisodium salt.

NMR (D$_2$O) δ: 1.65 (6H,s), 3.78 (2H,d,J=7Hz), 3.95 (2H,s), 4.47 (2H,t,J=7Hz), 4.46 (1H,d,J=5Hz), 5.99 (1H,d,J=5Hz), 6.85 (1H,s), 6.88 (1H,d,J=16Hz), 7.14 (1H,s), 7.35 (1H,d,J=16Hz), 7.72 (1H,s).

EXAMPLE 28

(6R, 7R)-7-[(Z)-2-aminothiazol-4-yl)-2-(1-methyl-1-carboxy)ethoxyiminoacetamido]-3-[2-(5-hydroxy-1-(3-carboxypropyl-4-pyridon-2-yl)vinyl]-ceph-3-em-4-carboxylic acid, trans-isomer (a) In 10 ml of acetone is dissolved 0.923 g of p-methoxybenzyl (6R,7R)-7-[(Z)-2-(2-tritylaminothiazol-4-yl)-2-(1-methyl-1-t-butoxycarbonyl)ethoxyimino]acetamido3-chloromethyl-ceph-3-em-4-carboxylate. To this solution are added 0.275 g of triphenylphosphine and 0.157 g of sodium iodide at room temperature, and the mixture is stirred for 1 hour. The reaction mixture is condensed to dryness under reduced pressure, and the residue is dissolved in 10 ml of dichloromethane. To the solution are added 1.223 g of diphenylmethyl 4-(3-diphenylmethoxy6-formyl-4-pyridone-1-yl)butanoate, 0.294 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 80 g of Wako-Gel C-300 (manufactured by Wako Pure Chemical Industries, Ltd.) with an eluent of ethyl acetate-benzene (1:2) to give 0.942 g of the trans-isomer of p-methoxybenzyl (6R,7R)-7-[(Z)-2-tritylaminothiazol-4-yl)-2-(1-methyl-1-t-butoxycarbonyl)ethoxyiminoacetamido]-3-[2-(5-(diphenylmethoxy-1-(2-diphenylmethoxycarbonyl) propyl)-4-pyridon-2-yl)vinyl]ceph-3-em-4carboxylate.

NMR CDCl$_3$) δ: 1.37 (9H,s), 1.57 (3H,s), 1.63 (3H,s), 1.63–2.1 (2H,m), 2.2–2.4 (2H,m), 3.3–3.8 (4H,m), 3.77 (3H,s), 4.96 (1H,d,J=5Hz), 5.20 (2H,broad s), 5.93 (1H,dd,J=5Hz,8Hz), 6.52 (1H,s), 6.54 (1H,d,J=16Hz), 6.6–7.6 (45H,m), 8.13 (1H,d,J=8Hz).

(b) A 0.928 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3-[2-(5-(diphenylmethoxy-1-(2-diphenylmethoxycarbonyl)propyl) -4-pyridon-2-yl)vinyl]ceph-3-em-4-carboxylate is dissolved in 2.0 g of anisole, and 10 ml of an ice-cooled trifluoroacetic acid is added dropwise. After stirring at the same temperature for 4 hours, 50 ml of ice-cooled isopropyl ether is added, and the resulting precipitate is collected by filtration and dried under reduced pressure. The crystal is suspended in 5 ml of water and adjusted to pH 7.5 by adding a 7% aqueous sodium hydrogen carbonate solution under ice-cooling to make a solution. Purification by 150 ml of DIAION HP-20 resin column chromatography (eluent: water, 10% methanol-water) gave the title compound (0.380 g) as a trisodium salt.

NMR (D$_2$O) δ: 1.64 (6H,s), 2.0–2.5 (4H,m), 3.94 (2H,broad s), 4.23 (2H,t,J=7Hz), 5.44 (1H,d,J=5Hz), 5.98 (1H,d,J=5Hz), 6.82 (1H,d,J=16Hz), 6.87 (1H,s), 7.12 (1H,s), 7.35 (1H,d,J=16Hz), 7.71 (1H,s).

EXAMPLE 29

(6R,7R)-7-[(Z)-2-aminothiazol-4-yl)-2-(1-methyl-1carboxy)ethoxyiminoacetamido]-3-[2-(5-hydroxy-1-(5-carboxypentyl)-4-pyridon-2-yl)vinyl)-ceph-3-em-4carboxylic acid, trans-isomer (a) In 6 ml of acetone is dissolved 0.461 g of p-methoxybenzyl (6R,7R)-7-[(Z)-2-(2-tritylaminothiazol-4-yl)-2-(1-methyl-1-t-butoxycarbonyl)ethoxyimino]acetamido-3-chloromethyl-ceph-3-em-4-carboxylate. To this solution are added 0.138 g of triphenylphosphine and 0.079 g of sodium iodide at room temperature, and the mixture is stirred for 1 hour. The reaction mixture is condensed to dryness under reduced pressure, and the residue is dissolved in 6 ml of dichloromethane. To the solution are added 1.115 g of diphenylmethyl 6-(3-diphenylmethoxy6-formyl-4-pyridon-1-yl)hexanoate, 0.147 g of sodium hydrogen carbonate and 5 ml of water, and the stirring is conducted at room temperature for 14 hours. The dichloromethane layer is separated, condensed under reduced pressure and subjected to separation and purification procedures by flash column chromatography on 30 g of Wako-Gel C-300 (manufactured by Wako Pure Chemical Industries, Ltd.) with an eluent of ethyl acetate-benzene (1:2) to give 0.427 g of the trans-isomer of p-methoxybenzyl (6R,7R)-7-[(Z)-2-tritylaminothiazol-4-yl)-2-(1-methyl-1-t-butoxycarbonyl)ethoxyiminoacetamido]-3-[2-(5-(diphenylmethoxy-1-(5-(diphenylmethoxycarbonyl) pentyl)-4-pyridon-2-yl)vinyl]ceph-3-em-4carboxylate.

NMR CDCl$_3$) δ: 1.2–2.0 (21H,m), 1.33 (2H,t,J=7Hz), 3.3–3.7 (4H,m), 3.77 (3H,s), 4.98 (1H,d,J=5Hz), 5.20 (2H,s), 5.92 (1H,dd,J=5Hz,8Hz), 6.32 (1H,d,J=16Hz), 6.49 (1H,s), 6.6–7.0 (7H,m), 7.0–7.5 (38H, m), 8.14 (1H,d,J=8Hz).

(b) A 0.418 g portion of the trans-isomer of p-methoxybenzyl (6R,7R)-7-[(Z)-2-tritylaminothiazol-4-yl)2-(1-methyl-1-t-butoxycarbonyl)ethoxyiminoacetamido]-3[2-(5-(diphenylmethoxy-1-(5-(diphenylmethoxycarbonyl)pentyl- 4-pyridon-2yl)vinyl]-ceph-3-em-4-carboxylate is dissolved in 1.0 g of anisole, and 5 ml of an ice-cooled trifluoroacetic acid is added dropwise. After stirring at the same temperature for 4 hours, 30 ml of ice-cooled isopropyl ether is added, and the resulting precipitate is collected by filtration and dried under reduced pressure. The crystal is suspended in 5 ml of water and adjusted to pH 7.5 by adding a 7% aqueous sodium hydrogen carbonate solution under ice-cooling to make a solution. Purification by 80 ml of DIAION HP-20 resin column chromatography (eluent: water, 20 % methanol-water) gave the title compound (0.380 g) as a trisodium salt.

NMR (D$_2$O) δ: 1.2–2.0 (12H), 2.30 (2H,t,J=7Hz), 3.92 (2H, broad s), 4.1–4.25 (2H,m), 5.44 (1H,d,J=5Hz), 5.99 (1H,dJ=5Hz), 6.81 (1H,d,J=16 Hz), 6.86 (1H,s), 7.13 (1H,s), 7.33 (1H,d,J=16Hz), 7.69 (1H,s).

EXAMPLE 30

(6R, 7R)-7-](Z)-2-aminothiazol-4-yl)-2-(1-methyl-1-carboxy)ethoxyiminoacetamido]-3-[2-(5-hydroxy-1-((1S)-1-carboxyethyl)-4-pyridon-2-yl)vinyl-ceph-3-em-4-carboxylic acid, trans-isomer and (6R, 7R)-7-[(Z)-2-aminothiazol-4-yl)-2-(1-methyl-1-carboxy)ethoxyiminoacetamido]-3-[2-(5-hydroxy-1-((1R)-1-carboxyethyl)-4-pyridon-2-yl)vinyl]-ceph-3-em-4-carboxylic acid, trans-isomer (a) In 10 ml of acetone is dissolved 0.923 g of p-methoxybenzyl (6R,7R)-7-[(Z)-2-(2-tritylaminothiazol-4-yl)-2-(1-methyl-1-t-butoxycarbonyl)ethoxyimino]acetamido-3-chloromethyl-ceph-3-em-4-carboxylate. To this solution are added 0.275 g of triphenylphosphine and 0.157 g of sodium iodide at room temperature, and the mixture is stirred for 1 hour. The reaction mixture is condensed to dryness under reduced pressure, and the residue is dissolved in 10 ml of dichloromethane. To the solution are added 1.087 g of diphenylmethyl DL-2(3-diphenylmethoxy-6-formyl-4-pyridon-1-yl)propionate, 0.294 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 120 g of Wako-Gel C-300 (manufactured by Wako Pure Chemical Industries, Ltd.) with an eluent of ethyl acetate-benzene (1:2) to give 0.548 g of the trans-isomer (3S-isomer) of p-methoxybenzyl (6R,7R)-7-[(Z)-2-tritylaminothiazol-4-yl)-2-(1-methyl-1-t-butoxycarbonyl)ethoxyiminoacetamido]-3-[2-(5-diphenylmethoxy-1-((1S)-1-(diphenylmethoxycarbonyl)ethyl)-4-pyridon-2-yl)vinyl]- ceph-3-em-4-carboxylate and 0.385 g of the trans-isomer (3R-isomer) of p-methoxybenzyl (6R,7R)-7-[(Z)-2-tritylaminothiazol-4-yl)-2-(1-methyl-1-t-butoxycarbonyl)ethoxyiminoacetamido]-3-[2-(5-diphenylmethoxy-1-((1R)-1-(diphenylmethoxycarbonyl)ethyl)-4-pyridon-2-yl)vinyl]-ceph-3-em-4-carboxylate.

3S-isomer:
NMR CDCl$_3$) δ: 1.37 (3H,d,J=7 Hz), 1.39 (9H,s), 1.58 (3H,s), 1.63 (3H,s), 3.18 (2H,broad s), 3.78 (3H,s), 4.72 (1H,q.J=7 Hz), 4.95 (1H,d,J=5 Hz), 5.20 (2H,ABq), 5.94 (1H,dd,J=5 Hz,8 Hz), 6.20 (1H,d,J=16 Hz), 6.42 (1H,s), 6.44 (1H,s), 6.70 (1H,s), 6.7–7.0 (6H,m), 7.0–7.5 (37H,m), 8.08 (1H,d,J=7 Hz).

3R-isomer:
NMR (CDCl$_3$) δ: 1.37 (3H,d,J=7 Hz), 1.39 (9H,s), 1.59 (3H,s), 1.64 (3H,s), 3.20 (2H,broad s), 3.78 (3H,s), 4.67 (1H,q.J=7 Hz), 4.96 (1H,d,J=5 Hz), 5.19 (2H,broad s), 5.93 (1H,dd,J=5 Hz,8 Hz), 6.17 (1H,d,J=16 Hz), 6.42 (1H,s), 6.51 (1H,s), 6.71 (1H,s), 6.75–7.0 (6H,m), 7.0–7.5 (37H,m), 8.16 (1H,d,J=8 Hz).

(b) The title compounds (3S-isomer and 3R-isomer) corresponding to respective 3-diastereomers obtained in (a) are also obtained as trisodium salts in the same manner as in Example 27(b).

3S-isomer (yield, 68%):
NMR (D$_2$O) δ: 1.65 (6H,s), 1.62 (2H,d,J=7 Hz), 3.90 (2H,s), 5.12 (1H,q,J=7 Hz), 5.44 (1H,d,J=7 Hz), 5.99 (1H,d,J=5 Hz), 6.76 (1H,d,J=16 Hz), 6.81 (1H,s), 7.13 (1H,s), 7.29 (1H,d,J=16 Hz), 7.69 (1H,s).

3R-isomer (yield, 73%):
NMR (D$_2$O) δ: 1.64 (6H,s), 1.81 (2H,d,J=7 Hz), 3.90 (2H,s), 5.09 (1H,q,J=7 Hz), 5.44 (1H,d,J=5 Hz), 5.99 (1H,d,J=5 Hz), 6.72 (1H,d,J=16 Hz), 6.83 (1H,s), 7.13 (1H,s), 7.32 (1H,d,J=16 Hz), 7.72 (1H,s).

EXAMPLE 31

(6R,7R)-7-[(Z)-2-aminothiazol-4-yl)-2-(1-methyl-1-carboxy)ethoxyiminoacetamido]-3-[2-(5-hydroxy-1-((1S)-1-carboxyethyl)-4-pyridon-2-yl)vinyl]-ceph-3-em-4-carboxylic acid, trans-isomer and (6R,7R)-7-[(Z)-2-aminothiazol-4-yl)-2-(1-methyl-1-carboxy)ethoxyiminoacetamido]-3-[2-(5-hydroxy-1-(α-carboxybenzyl)-4-pyridon-2-yl)vinyl]-ceph-3-em-4-carboxylic acid, trans-isomer (a) In 10 ml of acetone is dissolved 0.923 g of p-methoxybenzyl (6R,7R)-7-[(Z)-2-(2-tritylaminothiazol-4-yl)-2-(1-methyl-1-t-butoxycarbonyl)ethoxyimino]acetamido-3-chloromethyl-ceph-3-em-4-carboxylate. To this solution are added 0.275 g of triphenylphosphine and 0.157 g of sodium iodide at room temperature, and the mixture is stirred for 1 hour. The reaction mixture is condensed to dryness under reduced pressure, and the residue is dissolved in 10 ml of dichloromethane. To the solution are added 1.21 g of diphenylmethyl (2S)-2(3-diphenyl- methoxy-6-formyl-4-pyridon-1-yl)-2-phenylacetate, 0.294 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 150 g of Wako-Gel C-300 (manufactured by Wako Pure Chemical Industries, Ltd.) with an eluent of ethyl acetate-benzene (1:1) to give 0.621 g of the isomer A as a diastereomer on the 3-side chain of the trans-isomer [R$_f$: 0.75. benzene-ethyl acetate (1:1)]of p-methoxybenzyl (6R,7R)-7 [(Z) 2-tritylaminothiazol-4-yl)-(1-methyl-1-t-butoxycarbonyl)ethoxyiminoacetamido]-3-2-(5-diphenylmethoxy-1-(α-(diphenylmethoxycarbonyl)benzyl)-4-pyridon-2-yl)vinyl]ceph-3-em-4-carboxylate and 0.476 g of the isomer B [R$_f$: 0.65, benzene-ethyl acetate (1:1)]:

isomer A:
NMR CDCl$_3$) δ: 1.38 (9H,s), 1.58 (3H,s), 1.63 (3H,s), 3.03 (1H,d,J=18 Hz), 3.18 (1H,d,J=18 Hz), 3.81 (3H,s), 4.93 (1H,d,J=5 Hz), 5.20 (1H,d,J=12 Hz), 5.28 (1H,d,J=12 Hz), 5.89 (1H,s), 5.98 (1H,dd,J=5 Hz,8 Hz), 6.18 (1H,d,J=16 Hz), 6.27 (1H,s), 6.53 (1H,s), 6.70 (1H,s), 6.73 (1H,s), 6.8–7.0 (6H,m), 7.0–7.5 (41H,m), 8.12 (1H,d,J=8 Hz).

isomer B:

NMR CDCl₃) δ: 1.40 (9H,s), 1.60 (3H,s), 1.67 (3H,s), 3.07 (1H,d,J=18 Hz), 3.22 (1H,d,J=18 Hz), 3.80 (3H,s), 4.97 (1H,d,J=5 Hz), 5.20 (1H,d,J=12 Hz), 5.25 (1H,d,J=12 Hz), 5.83 (1H,s), 5.97 (1H,dd,J=5 Hz,8 Hz), 6.14 (1H,d,J=16 Hz), 6.27 (1H,s), 6.57 (1H,s), 6.73 (1H,s), 6.74 (1H,s), 6.8–7.0 (6H,m), 7.0–7.5 (41H,m), 8.15 (1H,d,J=8 Hz).

(b) The title compounds corresponding to respective 3-diastereomers obtained in (a) (isomer A' for the isomer A, and isomer B' from the isomer (B) are obtained as trisodium salts in the same manner as in Example 29(b): isomer A' (yield, 75%):

NMR (D₂O) δ: 1.53 (3H,s), 1.55 (3H,s), 3.74 (1H,d,J=18 Hz), 3.84 (1H,d,J=18 Hz), 5.35 (1H,d,J=5 Hz), 5.90 (1H,d,J=5 Hz), 6.20 (1H,s), 6.78 (1H,d,J=16 Hz), 6.79 (1H,s), 7.04 (1H,s), 7.22 (1H,d,J=16 Hz), 7.23 (1H,s), 7.3–7.6 (5H,m).

isomer B' (yield, 71%):

NMR (D₂O) δ: 1.55 (3H,s), 1.57 (3H,s), 3.81 (2H,s), 5.37 (1H,d,J=5 Hz), 5.92 (1H,d,J=5 Hz), 6.18 (1H,s), 6.74 (1H,d,J=16 Hz), 6.79 (1H,s), 7.04 (1H,s), 7.27 (1H,s), 7.28 (1H,d,J=16 Hz), 7.3–7.6 (5H,m).

EXAMPLE 32

(6R,7R)-7-[(Z)-2-aminothiazol-4-yl)-2-(1-methyl-1-carboxy)ethoxyiminoacetamido]-3-[2-(5-hydroxy-1-(N,N-dimethylaminocarbonylmethyl)-4-pyridon-2-yl)vinyl]-ceph-3-em-4-carboxylic acid, trans-isomer (a) In 5 ml of acetone is dissolved 0.434 g of p-methoxybenzyl (6R,7R)-7-[(Z)-2-(2-tritylaminothiazol-4-yl)-2-(1-methyl-1-diphenylmethoxycarbonyl)ethoxyimino]acetamido-3-chloromethyl-ceph-3-em-4-carboxylate. To this solution are added 0.116 g of triphenylphosphine and 0.066 g of sodium iodide at room temperature, and the mixture is stirred for 1 hour. The reaction mixture is condensed to dryness under reduced pressure, and the residue is dissolved in 10 ml of dichloromethane. To the solution are added 0.178 g of N,N'-dimethyl-2-(3-diphenylmethoxy-6-formyl-4-pyridon-1-yl)acetamide, 0.124 g of sodium hydrogen carbonate and 10 ml of water, and the stirring is conducted at room temperature for 14 hours. The dichloromethane layer is separated, condensed under reduced pressure and subjected to separation and purification procedures by flash column chromatography on 50 g of Wako-Gel C-300 (manufactured by Wako Pure Chemical Industries, Ltd.) with an eluent of ethyl acetate-benzene (1:1) to give 0.378 g of the trans-isomer of p-methoxybenzyl (6R,7R)-7-[(Z)-2-tritylaminothiazol-4-yl)-2-(1-methyl-1-diphenylmethoxycarbonyl)ethoxyiminoacetamido]-3-[2-(5-(diphenylmethoxy-1-(N,N-dimethylaminocarbonylmethyl)-4-pyridon-2-yl)vinyl]ceph-3-em-4-carboxylate:

NMR CDCl₃) δ: 1.65 (3H,s), 1.67 (3H,s), 2.79 (3H,s), 2.87 (3H,s), 3.37 (2H,broad s), 3.77 (3H,s), 4.37 (2H,broad s), 4.91 (1H,d,J=5 Hz), 5.19 (2H,s), 5.88 (1H,dd,J=5 Hz,8 Hz), 6.31 (1H,d,J=16 Hz), 6.47 (1H,s), 6.58 (1H, s), 6.65 (1H,s), 6.73 (1H,s), 6.75–7.0 (5H,m), 7.0–7.6 (38H,m).

(b) Starting from the trans-isomer (0.357 g) of p-methoxybenzyl (6R,7R)-7-[(Z)-2-tritylaminothiazol-4-yl)- 2-(1-methyl-1-diphenylmethoxycarbonyl)ethoxyiminoacetamido]-3-[2-(5-(diphenylmethoxy - 1- ( N,N-dimethylaminocarbonylmethyl)-4-pyridon-2-yl)vinyl]-ceph-3-em-4-carboxylate, the title compounds (0.146 g) is obtained as a disodium salt in the same manner as in Example 29(b):

NMR (D₂O) δ: 1.65 (6H,s), 3.10 (3H,s), 3.26 (3H,s), 3.82 (2H,broad s), 5.24 (2H,broad s), 5.43 (1H,d,J=5 Hz), 5.98 (1H,d,J=5 Hz), 6.49 (1H,d,J=16 Hz), 6.88 (1H,s), 7.11 (1H,s), 7.30 (1H,d,J=7 Hz), 7.60 (1H,s).

EXAMPLE 33

2-{3-{2-{(6R,7R)-7-[(Z)-2-aminothiazol-4-yl)-2-(1-methyl-1-carboxy)ethoxyiminoacetamido]-4-carboxyceph-3-em-3-yl)vinyl]-5-hydroxy-4-pyridon-1-yl]ethanesulfonic acid, trans-isomer (a) In 10 ml of acetone is dissolved 0.923 g of p-methoxybenzyl (6R,7R)-7-[(Z)-2-(2-tritylaminothiazol-4-yl)-2-(1-methyl-1-t-butoxycarbonyl)ethoxyimino]acetamido-3-chloromethyl-ceph-3-em-4-carboxylate. To this solution are added 0.275 g of triphenylphosphine and 0.157 g of sodium iodide at room temperature, and the mixture is stirred for 1 hour. The reaction mixture is condensed to dryness under reduced pressure, and the residue is dissolved in 20 ml of dichloromethane. To the solution are added 0.871 g of sodium 2-(3-diphenylmethoxy-6-formyl-4-pyridon-1-yl)ethanesulfonate, 0.294 g of sodium hydrogen carbonate, 1.86 g of benzyltriethylammonium chloride and the stirring is conducted at room temperature for 14 hours. The dichloromethane layer is separated, condensed under reduced pressure and subjected to separation and purification procedures by flash column chromatography on 150 g of Wako-Gel C-300 (manufactured by Wako Pure Chemical Industries, Ltd.) with an eluent of chloroform-methanol (10:1) to give 0.507 g of the transisomer of benzyltriethylammonium 2-{3-{3-{(6R,7R)-7-[(Z)-2-tritylaminothiazol-4-yl)-2-(1-methyl-1 -t-butoxycarbonyl)ethoxyiminoacetamido]-4-methoxycarbonyl-ceph- 3-em-3-yl}vinyl}-5-diphenylmethoxy-4-pyridon-1-yl}ethanesulfonate:

NMR CDCl₃) δ: 1.32 (9H,t,J=7 Hz), 1.38 (9H,s), 1.56 (6H,broad), 2.8–3.3 (8H,m), 3.5–3.8 (2H,m), 3.74 (3H,s), 3.9–4.2 (2H,m), 4.36 (2H,s), 4.8–4.95 (1H,broad), 5.17 (2H,broad s), 4.7–4.9 (1H,broad), 6.4–7.7 (41H,m), 8.0–8.2 (1H,broad).

(b) Starting from the trans-isomer (0.488 g) of benzyltriethylammonium 2-{3-{3-{(6R,7R)-7-[(Z)-2-tritylaminothiazol-4-yl)-2-(1-methyl-1-t-butoxycarbonyl)ethoxyiminoacetamido]-4-p-methoxycarbonylceph-3-em-3-yl}vinyl}-5-diphenylmethoxy-4-pyridon- 1-yl}ethanesulfonate, the title compounds (0.132 g) is obtained as a disodium salt in the same manner as in Example 27 (b):

NMR (D₂O) δ: 1.64 (6H,s), 3.49 (2H,t,J=7 Hz), 3.95 (2H,s), 4.61 (2H,t,J=7 Hz), 5.44 (1H,d,J=5 Hz), 5.99 (1H,d,J=7 Hz), 6.85 (1H,s), 6.91 (1H,d,J=16 Hz), 7.13 (1H,s), 7.35 (1H,d,J=16 Hz), 7.71 (1H,s).

EXAMPLE 34

(6R,7R)-7-[(Z)-2-aminothiazol-4-yl)-2-(1-methyl-1-carboxy)ethoxyiminoacetamido]-3-{2-[5-hydroxy-1-(3,4-dihydroxybenzyl)-4-pyridon-1-yl]vinylceph-3-em-4-carboxylic acid, trans-isomer (a) In 6 ml of acetone is dissolved 0.304 g of p-methoxybenzyl (6R,7R)-7-[(Z)-2-(2-tritylaminothiazol-4-yl)-2-(1-methyl-1-t-butoxycarbonyl)ethoxyimino]acetamido-3-chloromethyl-ceph-3-em-4-carboxylate. To this solution are added 0.091 g of triphenylphosphine and 0.052 g of sodium iodide at room temperature, and the mixture is stirred for 1 hour. The reaction mixture is condensed to dryness under reduced pressure, and the residue is dissolved in 6 ml of dichloromethane. To the solution are added 0.220 g of 1-[3,4-bis(p-methoxybenzyloxy)benzyl]-3-diphenylmethoxy-6-formyl-4-pyridon, 0.097 g of sodium hydrogen carbonate and 5 ml of water, and the stirring is conducted at room temperature for 14 hours. The dichloromethane layer is separated, condensed under reduced pressure and subjected to separation and purification procedures by flash column chromatography on 60 g of Wako-Gel C-300 (manufactured by Wako Pure Chemical Industries, Ltd.) with an eluent of chloroformmethanol (30:1) to give 0.272 g of the trans-isomer of p-methoxybenzyl (6R,7R)-7-[(Z)-2-tritylaminothiazol-4-yl)-2-(1-methyl--1-t-butoxycarbonyl)ethoxyiminoacetamido]-{2-{5-diphenylmethoxy-1-[3,4-bis(p-methoxybenzyloxy)benzyl]-4-pyridon-2-yl}vinyl}ceph-3-em-4-carboxylate:

NMR CDCl$_3$ δ: 1.37 (9H,s), 1.56 (3H,s), 1.60 (3H,s), 3.22 (2H,broad s), 3.71 (3H,s), 3.75 (3H,s), 3.78 (3H,s), 4.66 (2H,broad s), 4.86 (2H,s), 4.95 (1H,d,J=5 Hz), 5.02 (2H,s), 5.20 (2H,broad s), 5.92 (1H,dd,J=5 Hz,8 Hz), 5.95 (1H,d,J=16 Hz), 6.15–6.35 (3H,m), 6.52 (1H,s), 6.6–7.0 (12H,m), 7.0–7.5 (30H,m), 8.12 (1H,d,J=8 Hz).

(b) Starting from the trans-isomer (0.262 g) of p-methoxybenzyl (6R,7R)-7-[(Z)-2-tritylaminothiazol-4-yl)-2-(1-methyl-1-t-butoxycarbonyl)ethoxyiminoacetamido]-{2-{5-diphenylmethoxy-1-[3,4-bis(p-methoxybenzyloxy)benzyl]-4-pyridon-2-yl]-vinyl]ceph-3-em-4-carboxylate, the title compounds (0.122 g) is obtained as a disodium salt in the same manner as in Example 27 (b):

NMR (D$_2$O) δ: 1.63 (6H,s), 3.64 (2H,broad s), 5.24 (2H,broad s), 5.34 (1H,d,J=5 Hz), 5.93 (1H,d,J=5 Hz), 6.47.0 (5H,m), 7.07 (1H,s), 7.23 (1H,d,J=16 Hz), 7.77 (1H,broad s)

Anti-bacterial activity

The objective compound of the formula (I) or a salt thereof according to the present invention is a novel compound, and exhibits high anti-bacterial activities for inhibiting the growth of a wide range of pathogenic microorganisms including both Gram's positives and Gram's negatives. In order to illustrate the utility of the objective compound (I), anti-bacterial activities measured by the agar-dilution method for some of these compounds (I) are shown in table 1.

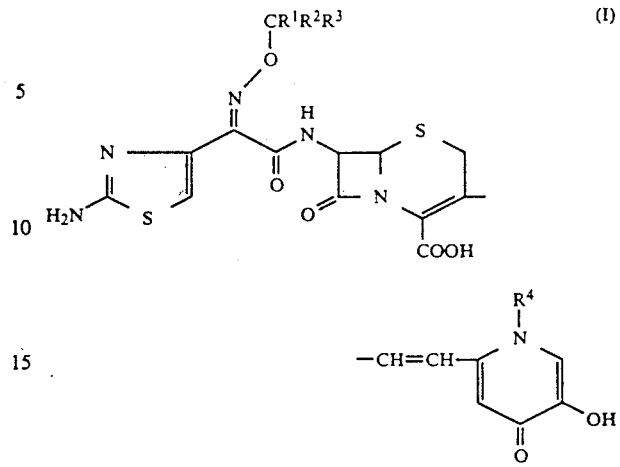

wherein $R^1$ represents a hydrogen atom, a carboxy group or an N-lower alkylcarbamoyl group, $R^2$ and $R^3$ may be the same or different and independently represent a hydrogen atom or a $C_1$–$C_3$ lower alkyl group, $R^4$ represents a hydrogen atom, a hydroxy group, a straight chain or branched $C_1$–$C_4$ lower alkoxy group, a substituted or unsubstituted straight or branched chain $C_1$–$C_4$ lower alkoxy group, a substituted straight or branched chain $C_1$–$C_4$ lower alkoxy group having a substituent selected from the group consisting of a hydroxy group, a lower alkoxy group, an amino group, a mono- or di-lower-alkyl-substituted amino group, an acyl group, a lower alkoxycarbonyl group, a carboxy group, a carbamoyl group, an N-lower alkyl substituted carbamoyl group, an N,N-di lower alkyl substituted carbamoyl group, a cyano group, a halogen atom, a nitro group, a sulfo group, a sulfonamido group, a mercapto group, an alkylthio group, an alkylsulfonyl group and an alkylsulfinyl group, a $C_3$–$C_6$ cycloalkyl group, a $C_2$–$C_4$ alkenyl or alkynyl group, a phenylmethyl group or heterocyclylmethyl group, a substituted phenylmethyl group having a substituent selected from the group consisting of a hydroxy group, a lower alkoxy group and an alkoxy-substituted benzyloxy group, and a heterocyclic ring of the heterocyclylmethyl group being a 2-furyl

TABLE 1

| Microorganism | Minimum Inhibitory Concentration (μg/ml) | | | | | | | |
|---|---|---|---|---|---|---|---|---|
| | Example 2 | Example 7 | Example 10 | Example 5 | Example 12 | Example 21 | Example 23 | Ceftazidime |
| Staphylococcus aureus 209PJC-1 | 25 | 6.25 | 12.5 | >100 | 100 | 100 | >100 | 3.13 |
| Bacillus subtilis ATCC 6633 | 6.25 | 0.78 | 0.78 | 100 | 12.5 | 12.5 | 50 | 3.13 |
| Escherichia coli No. 29 | ≦0.025 | 0.05 | 0.20 | 0.10 | 0.10 | 0.10 | 0.10 | 0.20 |
| Escherichia coli 255 | ≦0.025 | 0.10 | 0.20 | ≦0.025 | 0.05 | 0.10 | 0.10 | 25 |
| Klebsiella pneumoniae GN69 | 0.05 | 0.05 | 0.20 | ≦0.025 | 0.05 | 0.10 | 0.10 | 0.10 |
| Proteus vulgaris 76 | ≦0.025 | ≦0.025 | 0.10 | ≦0.025 | ≦0.025 | 0.05 | 0.05 | 0.05 |
| Cytrobacter freundii GN346 | 0.10 | 1.56 | 25 | 12.5 | 3.13 | 6.25 | 0.39 | 25 |
| Enterobacter cloacae GN7471 | 0.05 | 0.10 | 1.56 | 0.78 | 0.20 | 1.56 | 6.25 | 3.13 |
| Serratia marcescens No. 1 | ≦0.025 | ≦0.025 | 0.20 | 0.05 | 0.10 | 0.10 | 0.10 | ≦0.025 |
| Pseudomonas aeruginosa M-0148 | 0.20 | 12.5 | 12.5 | ≦0.025 | 0.20 | 0.20 | ≦0.025 | 1.56 |
| Pseudomonas aeruginosa E-2 | 0.10 | 1.56 | 0.78 | ≦0.025 | 0.05 | 0.05 | ≦0.025 | 0.39 |
| Pseudomonas aeruginosa IMA-1007 | 0.10 | 1.56 | 0.78 | ≦0.025 | ≦0.025 | ≦0.025 | ≦0.025 | 0.78 |
| Pseudomonas cepacia M-0527 | ≦0.025 | ≦0.025 | 12.5 | ≦0.025 | ≦0.025 | ≦0.025 | ≦0.025 | 0.039 |

What is claimed is:

1. A cephem compound which is either one of a cis- or trans-isomer or a mixture of the cis- and transisomers, represented by the following formula (I):

group, 4-pyridyl group, 1-methyl-4-pyridinyl group, 2-thienyl group, 1H-tetrazol-5-yl group, 1-methyl 1H-tetrazol-5-yl group, 4-methylthiazol-5-yl group, triazolyl group, thadiazolyl group, imidazol-1 group or oxazolyl group, and a pharmacologically acceptable salt thereof.

2. An antibacterial pharmaceutical composition comprising an antibacterially effective amount of a cephalosporin compound of the formula I as defined in claim 1, or a pharmaceutically acceptable salt thereof, and a pharmaceutically acceptable carrier of diluent.

* * * * *